US008674094B2

(12) United States Patent
Cook et al.

(10) Patent No.: US 8,674,094 B2
(45) Date of Patent: Mar. 18, 2014

(54) STABILIZED NUCLEIC ACID DARK QUENCHER-FLUOROPHORE PROBES

(75) Inventors: Ronald M. Cook, Novato, CA (US); Matt Lyttle, Fairfax, CA (US)

(73) Assignee: Biosearch Technologies, Inc., Petaluma, CA (US)

( * ) Notice: Subject to any disclaimer, the term of this patent is extended or adjusted under 35 U.S.C. 154(b) by 0 days.

(21) Appl. No.: 13/193,517

(22) Filed: Jul. 28, 2011

(65) Prior Publication Data
US 2011/0282041 A1 Nov. 17, 2011

Related U.S. Application Data

(63) Continuation of application No. 12/416,901, filed on Apr. 1, 2009, now Pat. No. 8,466,266.

(60) Provisional application No. 61/041,515, filed on Apr. 1, 2008.

(51) Int. Cl.
C07F 9/6512 (2006.01)
C07F 9/655 (2006.01)

(52) U.S. Cl.
USPC ............................. 544/243; 544/244; 549/222

(58) Field of Classification Search
None
See application file for complete search history.

(56) References Cited

U.S. PATENT DOCUMENTS

| | | | |
|---|---|---|---|
| 2,554,443 | A | 5/1951 | Hayden |
| 2,653,109 | A | 9/1953 | Switzer et al. |
| 2,830,943 | A | 4/1958 | Mackenzie |
| 2,945,849 | A | 7/1960 | Kruckenberg et al. |
| 3,369,013 | A | 2/1968 | Weaver et al. |
| 3,445,452 | A | 5/1969 | Wallace et al. |
| 3,523,936 | A | 8/1970 | Toji et al. |
| 3,709,870 | A | 1/1973 | Wolfrum |
| 4,069,012 | A | 1/1978 | Heinrich et al. |
| 4,313,872 | A * | 2/1982 | Heinrich et al. ............ 534/581 |
| 4,482,490 | A | 11/1984 | Imahori et al. |
| 4,588,517 | A | 5/1986 | Kaneko et al. |
| 4,623,716 | A | 11/1986 | Stevenson et al. |
| 4,687,728 | A | 8/1987 | Folkard et al. |
| 4,888,385 | A | 12/1989 | Hudson |
| 4,965,349 | A | 10/1990 | Woo et al. |
| 5,047,519 | A * | 9/1991 | Hobbs et al. ............ 536/27.14 |
| 5,231,191 | A | 7/1993 | Woo et al. |
| 5,312,738 | A | 5/1994 | Hamill et al. |
| 5,384,411 | A | 1/1995 | Robotti et al. |
| 5,401,847 | A | 3/1995 | Glazer et al. |
| 5,484,908 | A | 1/1996 | Froehler et al. |
| 5,612,221 | A | 3/1997 | Simons et al. |
| 5,723,591 | A | 3/1998 | Livak et al. |
| 5,736,626 | A | 4/1998 | Mullah et al. |
| 5,874,587 | A | 2/1999 | Donovan et al. |
| 5,925,517 | A | 7/1999 | Tyagi et al. |
| 6,008,379 | A | 12/1999 | Benson et al. |
| 6,037,130 | A | 3/2000 | Tyagi et al. |
| 6,046,049 | A | 4/2000 | Monia et al. |
| 6,103,476 | A | 8/2000 | Tyagi et al. |
| 6,117,986 | A | 9/2000 | Nardone et al. |
| 6,150,097 | A | 11/2000 | Tyagi et al. |
| 6,288,221 | B1 * | 9/2001 | Grinstaff et al. ............ 536/25.3 |
| 6,291,203 | B1 | 9/2001 | Poot et al. |
| 6,461,817 | B1 | 10/2002 | Alland et al. |
| 6,531,581 | B1 * | 3/2003 | Nardone et al. ............ 534/560 |
| 6,653,473 | B2 | 11/2003 | Reed et al. |
| 6,727,356 | B1 * | 4/2004 | Reed et al. ............ 536/26.6 |
| 6,790,945 | B2 | 9/2004 | Lukhtanov et al. |
| 6,818,420 | B2 | 11/2004 | Chou et al. |
| 7,019,129 | B1 | 3/2006 | Cook et al. |
| 7,109,312 | B2 | 9/2006 | Cook et al. |
| 7,160,996 | B1 | 1/2007 | Cook |
| 7,160,997 | B2 | 1/2007 | Chou et al. |
| 7,205,105 | B2 | 4/2007 | Afonina et al. |
| 7,309,573 | B2 * | 12/2007 | Sorge ............ 435/6.1 |
| 7,385,043 | B1 | 6/2008 | Kramer |
| 7,476,735 | B2 | 1/2009 | Laikhter et al. |
| 7,485,442 | B2 | 2/2009 | Afonina et al. |
| 7,582,432 | B2 * | 9/2009 | Cook et al. ............ 536/23.1 |
| 7,605,243 | B2 | 10/2009 | Laikhter et al. |

(Continued)

FOREIGN PATENT DOCUMENTS

EP 0008029 A1 2/1980
EP 0009191 A1 4/1980

(Continued)

OTHER PUBLICATIONS

Chou et al., "Use of Dark-Quenched Fret Probes in Real-Time PCR", (American Biotechnology Laboratory, 19(8), 34, 2001.*
McKeen et al., "Synthesis of Fluorophore and Quencher Monomers for Use in Scorpion Primers and Nucleic Acid Structural Probes", Organic & Bimolecular Chemistry, 1(13), 2267-2275, 2003.*
May et al., "Synthesis and Evaluation of a New NOn-Fluorescent Quencher in Fluorogenic Oligonucleotide Probes for Real-Time PCR", Organic & Bimolecular Chemistry, 3( ), 2534-2542, 2005.*
Chou et al., "Use of dark-quenched FRET probes in real-time PCR," American Biotechnology Laboratory 2001, 19(8), 34.

(Continued)

Primary Examiner — Michael Barker
(74) Attorney, Agent, or Firm — Morgan, Lewis & Bockius LLP; Jeffry S. Mann

(57) ABSTRACT

The present invention provides a new class of solids supports for synthesis of modified oligomers of nucleic acids, and nucleic acid probes that have a format expediently synthesized on the new supports. Exemplary solid supports include at least one quencher bound through a linker to the solid support. Various exemplary embodiments include a moiety that stabilizes a duplex, triplex or higher order aggregation (e.g., hybridization) of nucleic acids of which the oligomer of the invention is a component. Other components of the solid support include moieties that stabilize aggregations of nucleic acids, e.g., intercalators, minor groove binding moieties, bases modified with a stabilizing moiety (e.g., alkynyl moieties, and fluoroalkyl moieties), and conformational stabilizing moieties, such as those described in commonly owned U.S. Patent Application Publication No. 2007/0059752.

52 Claims, 2 Drawing Sheets

(56) References Cited

U.S. PATENT DOCUMENTS

| | | | |
|---|---|---|---|
| 7,645,872 B2 | 1/2010 | Laikhter et al. | |
| 7,662,550 B1 | 2/2010 | Tyagi et al. | |
| 7,662,942 B2 | 2/2010 | Reed et al. | |
| 7,759,473 B2* | 7/2010 | Fujihara et al. | 536/23.1 |
| 7,803,936 B2 | 9/2010 | Laikhter et al. | |
| 7,879,986 B2* | 2/2011 | Berry et al. | 534/752 |
| 7,897,736 B2 | 3/2011 | Reed et al. | |
| 8,192,961 B2* | 6/2012 | Williams | 435/91.2 |
| 8,410,255 B2 | 4/2013 | Cook et al. | |
| 8,440,399 B2 | 5/2013 | Cook et al. | |
| 8,466,266 B2 | 6/2013 | Cook et al. | |
| 2002/0177695 A1* | 11/2002 | Grinstaff et al. | 536/23.1 |
| 2003/0165920 A1* | 9/2003 | Chou et al. | 435/6 |
| 2004/0005607 A1 | 1/2004 | Ewing et al. | |
| 2005/0227254 A1 | 10/2005 | Lomholt et al. | |
| 2005/0272088 A1 | 12/2005 | Cook et al. | |
| 2006/0035262 A1 | 2/2006 | Cook et al. | |
| 2006/0177857 A1 | 8/2006 | Berry et al. | |
| 2006/0292589 A1* | 12/2006 | Reed et al. | 435/6 |
| 2007/0059752 A1 | 3/2007 | Cook | |
| 2007/0154898 A1 | 7/2007 | Cook et al. | |
| 2009/0259030 A1 | 10/2009 | Cook et al. | |
| 2010/0021922 A1 | 1/2010 | Cook et al. | |
| 2010/0087634 A1* | 4/2010 | Berry et al. | 534/727 |
| 2010/0298554 A1 | 11/2010 | Laikhter et al. | |
| 2011/0092679 A1 | 4/2011 | Cook et al. | |
| 2011/0178280 A1 | 7/2011 | Cook et al. | |

FOREIGN PATENT DOCUMENTS

| | | |
|---|---|---|
| EP | 0486477 A2 | 5/1992 |
| EP | 0601889 A2 | 6/1994 |
| EP | 0909823 A2 | 4/1999 |
| EP | 0876430 B1 | 8/2001 |
| FR | 1544951 | 11/1968 |
| FR | 2243438 A1 | 4/1975 |
| JP | H05-142600 A | 6/1993 |
| JP | H06-258676 A | 9/1994 |
| WO | WO 90/03446 A1 | 4/1990 |
| WO | WO 92/06102 A1 | 4/1992 |
| WO | WO 95/02848 A1 | 1/1995 |
| WO | WO 97/39008 A1 | 10/1997 |
| WO | WO 98/10096 A1 | 3/1998 |
| WO | WO 99/64431 A2 | 12/1999 |
| WO | WO 00/05411 A1 | 2/2000 |
| WO | WO 00/06778 A1 | 2/2000 |
| WO | WO 00/36152 * | 6/2000 |
| WO | WO 01/42505 A2 | 6/2001 |
| WO | WO 01/86001 A1 | 11/2001 |
| WO | WO 03/019145 A2 | 3/2003 |
| WO | WO 03/072051 A2 | 9/2003 |
| WO | WO 2006/002167 A2 | 1/2006 |
| WO | WO 2006/049297 A1 | 5/2006 |

OTHER PUBLICATIONS

Database CA [online], Chemical Abstracts Service, Columbus, Ohio, US; Blus, Kazimierz: "Synthesis and properties of disazo acid dyes"; retrieved from STN, Database accession No. 131:287725. [Source: Dyes and Pigments (1999), 43(3), 183-188.].

Database CA [online], Chemical Abstracts Service, Columbus, Ohio, US; Bumelis, V. et al: "Spectrophotometric study of the protonation of some azine dyes"; retrieved from STN, Database accession No. 85:125772. [Source: Nauchn. Konf. Khim.-Anal. Pribalt. Resp. B. SSR, [Tezisy Dokl.], 1st (1974), 62-8. Editor(s): Ramanauskas. E. Publisher: Vil'nyus. Gos. Univ., Vilnius, USSR.].

Database CA [online], Chemical Abstracts Service, Columbus, Ohio, US; Gonzalez-Gomez, C. et al: "Analytical method for determining color intensities based on Cherenkov radiation color quenching"; retrieved from STN, Database accession No. 98:209380. [Source: Journal of Radioanalytical Chemistry (1983), 77(1), 7-17.].

Database CA [online], Chemical Abstracts Service, Columbus, Ohio, US; Juarranz, A. et al: "Prediction of in situ fluorescence of histochemical reagents using a structure-staining correlation procedure"; retrieved from STN, Database accession No. 105:38550. [Source: Histochemistry (1986), 84(4-6), 426-31.].

Database CA [online], Chemical Abstracts Service, Columbus, Ohio, US; Po, Riccardo et al: "Synthesis and characterization of thermoplastic copolyesters containing copolymerized azoic dyes"; retrieved from STN, Database accession No. 122:215261. [Source: Polymers for Advanced Technologies (1995), 6(2), 63-8.].

Database CA [online], Chemical Abstracts Service, Columbus, Ohio, US; Szadowski, Jerzy et al: "Effect of dye solubility in polyglycol on its suitability for 'Cellestren' printing"; retrieved from STN, Database accession No. 110:136859. [Source: Przeglad Wlokienniczy (1988), 42(10), 436-9.].

De Clercq et al., "Nucleic Acid Related Compounds. 40. Synthesis and Biological Activities of 5-Alkynyluracil Nucleosides," J. Med. Chem. 1983, 26(5), 661-666.

Ediss et al., "A Broad Spectrum Colour Quencher for Liquid Scintillation Counting," Int. J. Appl. Radiat. Isot. 1982, 33(4), 296-297.

Endo et al., "Antitumor activity of phenazine derivatives against S 180 and C 63 in mice. I.," Chemical Abstracts 1966, 64, 1228e.

Froehler et al., "Oligodeoxynucleotides Containing C-5 Propyne Analogs of 2'-Deoxyuridine and 2'-Deoxycytidine," Tetrahedron Lett. 1992, 33(37), 5307-5310.

Goodchild et al., "Structural Requirements of Olefinic 5-Substituted Deoxyuridines for Antiherpes Activity," J. Med. Chem. 1983, 26(9), 1252-1257.

Hodgkiss et al., "Fluorescent markers for hypoxic cells. A study of novel heterocyclic compounds that undergo bio-reductive binding," Biochem. Pharmacol. 1991, 41(4), 533-541.

Jäger et al., "A Versatile Toolbox for Variable DNA Functionalization at High Density," J. Am. Chem. Soc. 2005, 127(43), 15071-15082.

Johansson et al., "Intramolecular Dimers: A New Strategy to Fluorescence Quenching in Dual-Labeled Oligonucleotide Probes," J. Am. Chem. Soc. 2002, 124(24), 6950-6956.

Juarranz et al., "Prediction of in situ fluorescence of histochemical reagents using a structure-staining correlation procedure," Histochemistry 1986, 84(4-6), 426-431.

Lukhtanov et al., "Novel DNA probes with low background and high hybridization-triggered fluorescence," Nucl. Acids Res. 2007, 35(5), e30 (pp. 1-14).

Marras et al., "Efficiencies of fluorescence resonance energy transfer and contact-mediated quenching in oligonucleotide probes," Nucleic Acids Res. 2002, 30(21), e122 (pp. 1-8).

Marshall et al., "A technique for distinguishing between methylene violet and methylene vio let Bernthsen," Stain Technol. 1975, 50(1), 51-53.

Marshall, P. N., "The composition of stains produced by the oxidation of Methylene Blue," Histochem. J. 1976, 8(4), 431-442.

Medina et al., "Improved thin-layer chromatographic detection of diethylstilbestrol and zeranol in plasma and tissues isolated with alumina and ion-exchange membrane columns in tandem," J. Chromatogr. 1993, 614(2), 315-323.

Medina et al., "Thin-layer chromatographic detection of zeranol and estradiol in fortified plasma and tissue extracts with Fast Corinth V," J. Chromatogr. 1992, 581(1), 119-128.

Moreira et al., "Effects of fluorescent dyes, quenchers, and dangling ends on DNA duplex stability," Biochem. Biophys. Res. Commun. 2005, 327(2), 473-484.

Nadeau et al., "Real-Time, Sequence-Specific Detection of Nucleic Acids during Strand Displacement Amplification," Anal. Biochem. 1999, 276(2), 177-187.

Pelander et al., "Preparation of N-demethylated drug metabolites for analytical purposes using 1-chloroethyl chloroformate," Forensic Sci. Int. 1997, 85(3), 193-198.

Pelander et al., "Screening for cyanobacterial toxins in bloom and strain samples by thin layer chromatography," Water Research 1996, 30(6), 1464-1470.

Rahim et al., "5-Alkynyl Pyrimidine Nucleosides as Potent Selective Inhibitors of Varicella-Zoster Virus," Antivir. Chem. Chemother. 1992, 3(5), 293-297.

Sahlin et al., "Differentiation between attached and ingested immune complexes by a fluorescence quenching cytofluorometric assay," J. Immunol. Methods 1983, 60(1-2), 115-124.

(56) References Cited

OTHER PUBLICATIONS

Tsuda et al., "The comet assay in eight mouse organs: results with 24 azo compounds," Mutat. Res. 2000, 465(1-2), 11-26.
Tyagi et al., "Molecular beacons: Probes that Fluoresce upon Hybridization," Nat. Biotechnol. 1996, 14(3), 303-308.
Uzdensky, De la Cellule au Cerveau: le Cytosquelette, Communication Intra- et Inter-Cellulaire, le Systeme Nerveux Central, Les Houches, [Ecole d'Ete de Physique Theorique], 65th, Les Houches, Fr., Meeting Dates Jul. 8-26, 1996.
Valkó et al., "Application of Chromatographic Retention Data in an Investigation of a Quantitative Structure—Nucleotide Incorporation Rate Relationship," J. Chromatogr. 1990, 506, 35-44.
Valkó et al., "Correlation of Nucleotide Incorporation Rate and HPLC Retention Parameters of Substituted Nucleosides," J. Liq. Chromatogr. 1989, 12(11), 2103-2116.
Venkataraman, K., ed., The Chemistry of Synthetic Dyes, vol. I and II, Academic Press, New York, NY, 1952; pp. 658-667, 790-795.
Vennerstrom et al., "Antimalarial Dyes Revised: Xanthenes, Azines, Oxazines and Thiazines," Antimicrob. Agents Chemother. 1995, 39(12), 2671-2677.
Walton et al., "Evaluation of New Linkers and Synthetic Methods for Internal Modified Oligonucleotides," Bioconjugate Chem. 2002, 13(5), 1155-1158.
Xie et al., "Synthesis and non-linear optical properties of four polyurethanes containing different chromophore groups," Eur. Polym. J. 2001, 37(3), 497-505.
Zollinger, H., Chapter 4 "Di- and Triarylmethine Dyes and their Aza Analogs" in Color Chemistry: Syntheses, Properties and Applications of Organic Dyes and Pigments, 2nd ed.; VCH Publishers: New York, NY, 1991; pp. 71-86.
Cardullo et al., "Detection of nucleic acid hybridization by nonradiative fluorescence resonance energy transfer," Proc. Natl. Acad. Sci. USA 1988, 85(23), 8790-8794.
Colour Index International, 3rd ed. (4th rev.); The Society of Dyers and Colourists: Bradford, West Yorkshire, England, 1992; p. v, Contents and p. viii.
Endo et al., "Studies on Antitumor Activity of Phenazine Derivatives Against S 180 and C 63 in Mice (I)," Sci. Rep. Res. Inst. Tohoku Univ. C 1965, 12(1), 53-57.
Glen Research, "Catalog No. 10-5931-xx. Description: 5'-BHQ-1 Phosphoramidite," http://www.glenres.com/ProductFiles/10-5931.html, Nov. 4, 2011.
Glen Research, "Catalog No. 10-5941-xx. Description: BHQ-1-dT," http://www.glenres.com/ProductFiles/10-5941.html, Nov. 4, 2011.
Nazarenko et al., "A closed tube format for amplification and detection of DNA based on energy transfer," Nucleic Acids Res. 1997, 25(12), 2516-2521.
Sawicki, E., "Physical Properties of the Aminoazobenzene Dyes. IX. Absorption Spectra in Alcohol and Acid Solution of Disazobenzene Dyes," J. Org. Chem. 1958, 23(4), 532-535.
Wang, S.-S., "p-Alkoxybenzyl Alcohol Resin and p-Alkoxybenzyloxycarbonylhydrazide Resin for Solid Phase Synthesis of Protected Peptide Fragments," J. Am. Chem. Soc. 1973, 95(4), 1328-1333.
Wikipedia, "Phenazine," retrieved Mar. 21, 2012 from http://en.wikipedia.org/w/index.php?title=Phenazine&oldid=476096214.
Yang et al., "Evaluation of tetramethylrhodamine and black hole quencher 1 labeled probes and five commercial amplification mixes in TaqMan real-time RT-PCR assays for respiratory pathogens," J. Virol. Methods 2009, 162(1-2), 288-290.
Examination Report dated Sep. 10, 2013, received in European Application No. 10184585.7, which is related by priority to U.S. Appl. No. 09/567,863, 3 pages (Cook).
Examination Report dated Sep. 9, 2013, received in European Application No. 10184701.0, which is related by priority to U.S. Appl. No. 09/567,863, 5 pages (Cook).
Notice of Allowance dated Sep. 17, 2013, received in U.S. Appl. No. 12/765,844, 6 pages (Cook).
Examination Report dated Apr. 15, 2013, received in European Application No. 01935256.6, which is related by priority to U.S. Appl. No. 09/567,863, 3 pages (Cook).
Communication about intention to grant a European patent dated Jun. 17, 2013, received in European Application No. 09726629.0, which is related by priority to U.S. Appl. No. 12/416,901, 90 pages (Cook).
Office Action dated Apr. 29, 2013, received in U.S. Appl. No. 11/226,852, 6 pages (Cook).
Notice of Intent to Issue a Reexam Certificate dated May 14, 2013, received in U.S. Reexamination No. 95/001,710, 4 pages (Cook).
Reexamination Certificate dated May 31, 2013, received in U.S. Reexamination No. 95/001,710, 2 pages (Cook).
Notice of Intent to Issue a Reexam Certificate dated Apr. 9, 2013, received in U.S. Reexamination No. 95/001,711, 4 pages (Cook).
Reexamination Certificate dated May 10, 2013, received in U.S. Reexamination No. 95/001,711, 2 pages (Cook).
Examination Report dated Nov. 19, 2013, in European Application No. 01935256.6, which is related by priority to U.S. Appl. No. 09/567,863, 3 pages. (Cook).

* cited by examiner

Scheme 1

Scheme 2

```
SEQUENCE LISTING

<160> NUMBER OF SEQ ID NOS: 1

<210> SEQ ID NO 1
<211> LENGTH: 10
<212> TYPE: DNA
<213> ORGANISM: Artificial Sequence
<220> FEATURE:
<223> OTHER INFORMATION: probe

<400> SEQUENCE: 1
tttttttttt                                                           10
```

STABILIZED NUCLEIC ACID DARK QUENCHER-FLUOROPHORE PROBES

CROSS-REFERENCE TO RELATED APPLICATIONS

This application is a continuation of U.S. patent application Ser. No. 12/416,901, filed Apr. 1, 2009, which claims priority under 35 U.S.C. 119(e) to U.S. Provisional Patent Application No. 61/041,515, filed Apr. 1, 2008, the disclosures of which are incorporated herein by reference in their entirety for all purposes.

TECHNICAL FIELD

The invention relates generally to novel materials (e.g., solid supports and phosphoramidited) for nucleic acid synthesis. Exemplary materials include a solid support and a phosphoramidite functionalized with a stabilizing moiety. Various materials are functionalized with both a stabilizing moiety and a quencher. The invention also provides nucleic acid monomers and oligomers, including fluorescent-labeled probes synthesized using these materials. Also provided are methods of oligomer-based analyses and diagnosis utilizing oligomer probes of the invention binding to nucleic acid target sequences.

BACKGROUND OF THE INVENTION

Fluorescent oligonucleotide probes are important tools for genetic analysis, in both genomic research and development, and in clinical medicine. One particularly useful class of fluorescent probes is self quenching probes, also known as fluorescence energy transfer probes, or FET probes. Although the design of different probes using this motif may vary in detail, FET probes contain both a fluorophore and quencher tethered to an oligonucleotide. The fluorophore and the quencher are configured to produce a signal only as a result of hybridization to an intended target. Despite the limited availability of FET probes, techniques incorporating their use are rapidly displacing competitive methods.

Probes containing a fluorophore-quencher pair have been developed for hybridization assays where the probe forms a hairpin structure, i.e., where the probe hybridizes to itself to form a loop such that the quencher molecule is brought into proximity with the reporter molecule in the absence of a complementary nucleic acid sequence to prevent the formation of the hairpin structure (see, for example, WO 90/03446; European Patent Application No. 0 601 889 A2). When a complementary target sequence is present, hybridization of the probe to the complementary target sequence disrupts the hairpin structure and causes the probe to adopt a conformation where the quencher molecule is no longer close enough to the reporter molecule to quench the reporter molecule. As a result, the probes provide an increased fluorescent signal when hybridized to a target sequence than when they are unhybridized. Probes including a hairpin structure can be difficult to design and may interfere with the hybridization of the probe to the target sequence.

Assays have also been developed for identifying the presence of a hairpin structure using two separate probes, one containing a reporter molecule and the other a quencher molecule (see, Meringue, et al., *Nucleic Acids Research,* 22: 920-928 (1994)). In these assays, the fluorescence signal of the reporter molecule decreases when hybridized to the target sequence due to the quencher molecule being brought into proximity with the reporter molecule.

One particularly important application for probes including a reporter-quencher molecule pair is their use in nucleic acid amplification reactions, such as polymerase chain reactions (PCR), to detect the presence and amplification of a target nucleic acid sequence. In general, nucleic acid amplification techniques have opened broad new approaches to genetic testing and DNA analysis (see, for example, Arnheim et al. *Ann. Rev. Biochem.,* 61: 131-156 (1992)). PCR, in particular, has become a research tool of major importance with applications in, for example, cloning, analysis of genetic expression, DNA sequencing, genetic mapping and drug discovery (see, Arnheim et al., supra; Gilliland et al., *Proc. Natl. Acad. Sci. USA* 87: 2725-2729 (1990); Bevan et al., *PCR Methods and Applications,* 1: 222-228 (1992); Green et al., *PCR Methods and Applications,* 1: 77-90 (1991); Blackwell et al., *Science,* 250: 1104-1110 (1990)).

Commonly used methods for detecting nucleic acid amplification products require that the amplified product be separated from unreacted primers. This is typically achieved either through the use of gel electrophoresis, which separates the amplification product from the primers on the basis of a size differential, or through the immobilization of the product, allowing free primer to be washed away. However, three methods for monitoring the amplification process without prior separation of primer have been described. All of them are based on FRET, and none of them detect the amplified product directly. Instead, all three methods detect some event related to amplification. For that reason, they are accompanied by problems of high background, and are not quantitative, as discussed below.

One method, described in Wang et al. (U.S. Pat. No. 5,348,853; Wang et al., *Anal. Chem.,* 67: 1197-1203 (1995)), uses an energy transfer system in which energy transfer occurs between two fluorophores on the probe. In this method, detection of the amplified molecule takes place in the amplification reaction vessel, without the need for a separation step. This method, however, does not detect the amplified product, but instead detects the dissociation of primer from the "energy-sink" oligonucleotide. Thus, this method is dependent on detection of a decrease in emissions; a significant portion of labeled primer must be utilized in order to achieve a reliable difference between the signals before and after the reaction.

A second method detecting an amplification product without prior separation of primer and product is the 5'-nuclease PCR assay (also referred to as the TaqMan™ assay) (Holland et al., *Proc. Natl. Acad. Sci. USA,* 88: 7276-7280 (1991); Lee et al., *Nucleic Acids Res.,* 21: 3761-3766 (1993)). This assay detects the accumulation of a specific PCR product by hybridization and cleavage of a doubly labeled fluorogenic probe (the "TaqMan" probe) during the amplification reaction. The fluorogenic probe consists of an oligonucleotide labeled with both a fluorescent reporter dye and a quencher dye. During PCR, this probe is cleaved by the 5'-exonuclease activity of DNA polymerase if, and only if, it hybridizes to the segment being amplified. Cleavage of the probe generates an increase in the fluorescence intensity of the reporter dye.

In the TaqMan assay, the donor and quencher are preferably located on the 3'- and 5'-ends of the probe, because the requirement that 5'-3 hydrolysis be performed between the fluorophore and quencher may be met only when these two moieties are not too close to each other (Lyamichev et al., *Science,* 260:778-783 (1993). This requirement is a serious drawback of the assay as the efficiency of energy transfer decreases with the inverse sixth power of the distance between the reporter and quencher. Thus, if the quencher is not close enough to the reporter to achieve the most efficient quenching the background emissions from unhybridized probe can be quite high.

Yet another method of detecting amplification products that relies on the use of energy transfer is the "beacon probe" method described by Tyagi et al. (*Nature Biotech.*, 14:303-309 (1996)) which is also the subject of U.S. Pat. Nos. 5,119,801 and 5,312,728 to Lizardi et al. This method employs oligonucleotide hybridization probes that can form hairpin structures. On one end of the hybridization probe (either the 5'- or 3'-end) there is a donor fluorophore, and on the other end, an acceptor moiety. In this method, the acceptor moiety is a quencher, absorbing energy from the donor. Thus when the beacon is in the open conformation, the fluorescence of the donor fluorophore is detectable, whereas when the beacon is in hairpin (closed) conformation, the fluorescence of the donor fluorophore is quenched. When employed in PCR, the molecular beacon probe, which hybridizes to one of the strands of the PCR product, is in "open conformation," and fluorescence is detected, while those that remain unhybridized will not fluoresce. As a result, the amount of fluorescence will increase as the amount of PCR product increases, and thus can be used as a measure of the progress of the PCR.

Because this method is based on hybridization of the probe to a template region between the primer sequences, it has a number or problems associated with it. For example, it is unlikely that the beacon probes will hybridize quantitatively to one strand of double-stranded PCR product, especially when the amplification product is much longer than the beacon probe.

Additional limitations have also impeded the application and use of FET probes. First, currently available probe designs have a higher fluorescent noise background than is desirable. In some cases this is due to the difficulty of purifying the probe which must be rigorously purged of any spurious fluorescent byproducts. As a result probes must undergo at least 2 levels of purification before they are acceptable. This labor factor results in very high probe cost, approximately $300-$600 per probe. A second fundamental limitation is the inherent noise of the probe itself which is a result of the physical geometry of the probe which places constraints on the fluorophore and quencher interaction.

More recently, oligonucleotides have been shown to bind in a sequence-specific manner to duplex DNA to form triplexes. Single-stranded nucleic acid, primarily RNA, is the target molecule for oligonucleotides that are used to inhibit gene expression by an "antisense" mechanism (Uhlmann, E., et al., Chem Reviews (1990) 90:543-584; van der Krol, A. R., et al., Biotechniques (1988) 6:958-976). Antisense oligonucleotides are postulated to exert an effect on target gene expression by hybridizing with a complementary RNA sequence. In this model, the hybrid RNA-oligonucleotide duplex interferes with one or more aspects of RNA metabolism including processing, translation and metabolic turnover. Chemically modified oligonucleotides have been used to enhance their nuclease stability.

Duplex DNA can be specifically recognized by oligormers based on a recognizable nucleomonomer sequence. Exemplary recognition rules are outlined by Maher III, L. J., et al., *Science* (1989) 245:725-730; Moser, H. E., et al., *Science* (1987) 238:645-650; Beal, P. A., et al., *Science* (1992) 251:1360-1363; Cooney, M., et al., *Science* (1988) 241:456-459; and Hogan, M. E., et al., EP Publication 375408.

Sequence-specific targeting of both single-stranded and duplex target sequences has applications in diagnosis, analysis, and therapy. Under some circumstances wherein such binding is to be effected, it is advantageous to stabilize the resulting duplex or triplex over long time periods.

The use of triple helix (or triplex) complexes as a means for inhibition of the expression of target gene expression was previously adduced (International Application No. PCT/US89/05769). Triple helix structures have been shown to interfere with target gene expression (International Application No. PCT/US91/09321; Young, S. L., et al., *Proc. Natl. Acad. Sci.* (1991) 88:10023-10026), demonstrating the feasibility of this approach.

European Patent Application No. 92103712.3, Rahim, S. G., et al (*Antiviral Chem. Chemother.* (1992) 3:293-297), and International Application No. PCT/SE91/00653 describe pyrimidine nucleomonomers having an unsaturated group in the 5-position. 5-Propynyl and 5-ethynyl groups are among the described derivatives.

Synthesis of nucleomonomers having unsaturated alkyl groups at the 5-position of uracil has been described (DeClercq, E., et al., *J. Med. Chem.* (1983) 26:661-666; Goodchild, J., et al., *J. Med. Chem.* (1983) 26:1252-1257). Oligomers containing 5-propynyl modified pyrimidines have been described (Froehler, B. C., et al., *Tetrahedron Letters* (1992) 33:5307-5310).

Conversion of 5-propynyl-2'-deoxyuridine, 5-butynyl-2'-deoxyuridine and related compounds to the 5'-triphosphate followed by incorporation of the monomer into oligomers by *E. coli* polymerase has been described (Valko, K., et al., *J. Liquid Chromatog.* (1989) 12:2103-2116; Valko, K. et al., *J. Chromatog.* (1990) 506:35-44). These studies were conducted as a structure to activity analysis of nucleotide analogs having a series of substitutions at the 5-position of uracil. The activity of the nucleotide analogs as substrates for *E. coli* polymerase was examined and correlated with characteristics such as the hydrophobicity of the monomer. No information was presented regarding the properties of oligomers containing the analogs.

Oligomers having enhanced affinity for complementary target nucleic acid sequences would have improved properties for diagnostic applications, therapeutic applications and research reagents. Moreover, there exists in the art a need for improved probes for detecting nucleic acids (e.g., amplification products) rapidly, sensitively, reliably and quantitatively. Ideal probes would give rise to minimal background signal and be easily and inexpensively prepared. Quite surprisingly, the present invention provides such probes. Oligomeric FET and FRET probes of the present invention have improved binding affinity for double stranded and/or single stranded target sequences.

SUMMARY OF THE INVENTION

Figure 1:
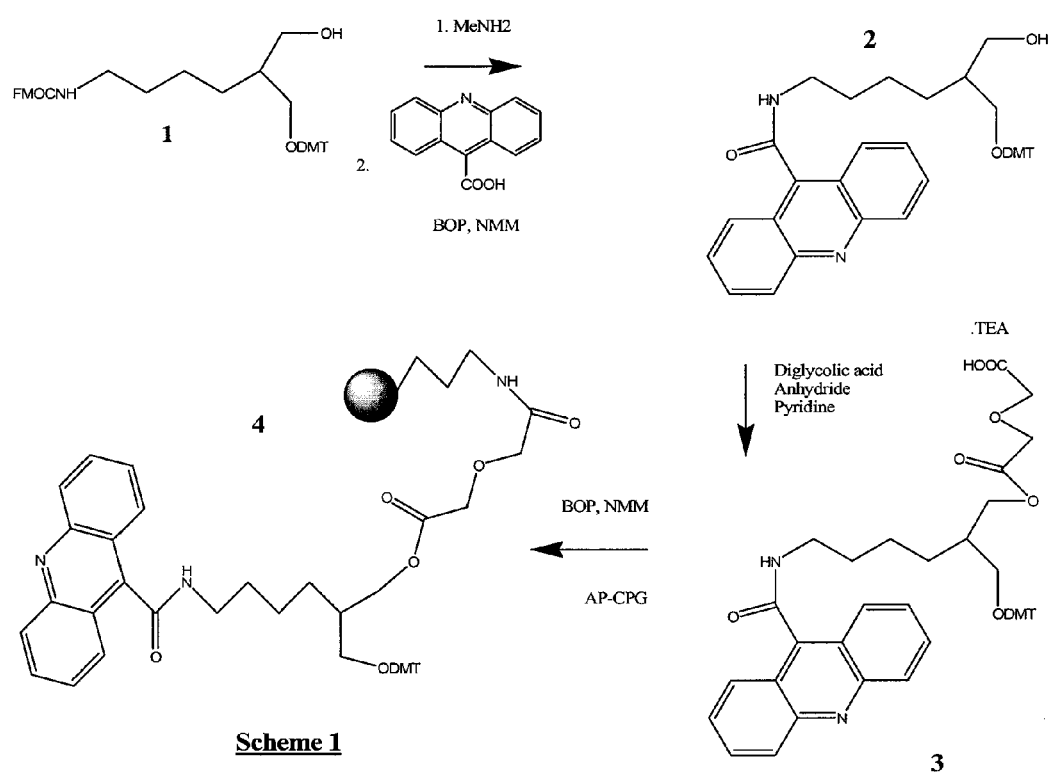
FIG. 1 is a scheme showing an exemplary preparation of a solid support of the invention functionalized with a stabilizing moiety.

The present invention provides a new class of phosphoramidites and solid supports for synthesis of modified nucleic acid oligomers, and nucleic acid probes (e.g., oligomers, e.g., oligonucleotides) of a format expediently synthesized using the phosphoramidites or on the new supports. Exemplary solid supports include at least one quencher bound through a linker to the solid support. Various exemplary embodiments provide a solid support or a phosphoramidite functionalized a moiety that stabilizes a duplex, triplex or higher order aggregation (e.g., hybridization) of the oligomer of the invention with a target nucleic acid. Exemplary components of the solid support (and the oligomers) include moieties that stabilize hybridization of nucleic acids, e.g., intercalators, minor groove binding moieties, bases modified with a stabilizing moiety (e.g., alkynyl moieties, and fluoroalkyl moieties), and conformational stabilizing moieties, such as those described in commonly owned U.S. Patent Application Publication No. 2007/0059752. Exemplary oligomers synthesized on the solid supports of the invention, or using the phosphoramidites of the invention include a quencher and a stabilizing moiety. Various oligomers also include a fluorophore and, optionally, one or more additional detectable moiety, stabilizing or quencher moiety.

In an exemplary embodiment, the quencher linked to the solid support, phosphoramidite or oligomer of the invention is a member of a class of quenchers in which a first substituted or unsubstituted aryl or first substituted or unsubstituted heteroaryl moiety is linked to a second substituted or unsubstituted aryl or second substituted or unsubstituted heteroaryl moiety through an exocyclic diazo bond. In an exemplary embodiment, the quenchers are essentially non-fluorescent ("dark quenchers"), and are optionally members of a class of compounds termed "Black Hole Quenchers™" ("BHQs"), which are disclosed in commonly owned U.S. Pat. No. 7,109, 312. The solid supports, phosphoramidites and oligomers functionalized with these quenchers can also be bound to one or more conjugated components, generally covalently conjugated to the base or sugar of the nucleic acid phosphoramidite, solid support or oligomer through a linker. An exemplary conjugated component is a minor groove binder, an intercalator, a fluorocarbon hybridization stabilizing moiety, an alkynyl hybridization stabilizing moiety (collectively, "stabilizing moieties"), a fluorophore and a quencher of fluorescent energy.

In exemplary embodiments, the present invention provides solid supports and phosphoramidites appropriate for synthesizing oligomeric nucleic acid probes including a stabilizing moiety, a quencher and/or a fluorophore. Also provided are probes of a format expediently manufactured on such a solid support or using such a phosphoramidite. Exemplary oligomeric nucleic acid probes of the invention are characterized by interaction between a quencher and a fluorophore, each conjugated to the oligomer in order to minimize the fluorescence of the probe in the absence of its interaction with a target (e.g., hybridization to a nucleic acid at least partially complementary to the target sequence).

In many dual-labeled nucleic acid probes, the interaction between the fluorophore and the quencher is brought about by using a nucleic acid probe sequence that forms a secondary structure (e.g., hairpin, loop, etc.). Requiring that a probe adopt a secondary structure significantly complicates the design of the probe and greatly restricts the nucleic acid sequences that can be used as components of the probes. In contrast, exemplary oligomeric nucleic acid probes of the invention facilitate the interaction between the quencher and the fluorophore without requiring concomitant formation of nucleic acid secondary structure, thereby allowing a much greater diversity of nucleic acid sequences to be used as components of fluorescent probes. In various embodiments, these probes include one or more Dark Quencher (e.g., Black Hole Quencher) as defined herein.

Moreover, by varying the number and identity of the members of the conjugated diazo-(hetero)aryl system of the quenchers used in the present invention the spectral properties (e.g., absorbance) of the quencher can be "tuned" to match the spectral characteristics (e.g., emission) of one or more fluorophores. This characteristic provides oligomeric probes of the invention selectable to have a broad range of absorbance maxima. Accordingly the oligomeric probes of the invention are well-suited for use in multiplexing applications. Furthermore, the invention provides solid supports and probes useful in multiplexing applications using one or more distinct fluorophore in combination with one or more quencher, thereby expanding the choices of donor-acceptor pairs that can be incorporated into the oligomeric probes. Accordingly, in various embodiments, the invention provides at least 2, at least 3, at or least 4 oligomeric probes each of which is functionalized with a quencher having a spectral property differentiatable from the same property of the quencher in the other probes (e.g., emission wavelength).

In an exemplary embodiment, the invention provides a compound having a structure according to Formula I:

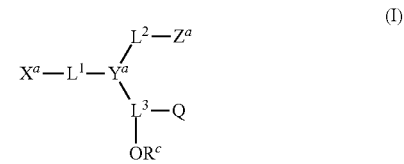

wherein $X^a$ is a stabilizing moiety selected from fluoroalkyl, substituted or unsubstituted aryl and substituted or unsubstituted heteroaryl. In various embodiments, $X^a$ is a minor groove binder or an intercalating agent.

The symbols $L^1$, $L^2$, $L^3$ and $L^4$ represent linkers. The linkers are independently selected from a single covalent bond, substituted or unsubstituted alkyl and substituted or unsubstituted heteroalkyl moieties. $Y^a$ is a member selected from $CR^a$, and N in which $R^a$ is a member selected from H, substituted or unsubstituted alkyl and substituted or unsubstituted heteroalkyl. $R^a$ is optionally a linker to a functional component.

The symbol $Z^a$ represents a solid support, $OR^b$ or $NR^bR^{b'}$ in which $R^b$ and $R^{b'}$ are members independently selected from H, substituted or unsubstituted alkyl and substituted or unsubstituted heteroalkyl. The symbol $R^c$ represents a member selected from H, substituted or unsubstituted alkyl, substituted or unsubstituted heteroalkyl, substituted or unsubstituted aryl, substituted or unsubstituted heteroaryl and a phosphorus-containing linker covalently bound to a nucleic acid. In an exemplary embodiment, $R^c$ is a nucleic acid protecting group, e.g., dimethoxytrityl ("DMT"). In another embodiment, $R^c$ is a phosphodiester linker to another nucleic acid moiety, which is optionally derivatized with one or more functional component.

The compounds of the invention include a quencher of fluorescence energy. The quencher is represented by the symbol Q and, in exemplary embodiments, includes one or more of the following structural features:

(a) at least three residues, each independently selected from substituted or unsubstituted aryl, and substituted or unsubstituted heteroaryl, wherein the first residue is covalently linked to the second residue via a first exocyclic diazo bond. The first or the second residue is covalently linked to a third residue through a second diazo bond; and (b) at least two residues, each independently selected from substituted or unsubstituted aryl, and substituted or unsubstituted heteroaryl. The first residue is covalently linked to the second residue via an exocyclic diazo bond, and at least one the residues is a member selected from substituted or unsubstituted polycyclic aryl and substituted or unsubstituted polycyclic heteroaryl groups.

The quenchers are linked to the remainder of the compound of the invention via a linker. The quencher and the linker are coupled by reaction of a reactive functional group on a precursor quencher and a reactive functional group on the linker. The two reactive functional groups are of complementary reactivity and upon reaction form a linkage fragment as defined herein.

Other objects, advantages and aspects of the present invention will be apparent from the detailed description below.

DETAILED DESCRIPTION OF THE INVENTION

Abbreviations

"BHQ," as used herein, refers generally to dark quenchers including one or more diazo bond and specifically to "Black Hole Quenchers™." Exemplary BHQ's of use in the present invention are described in U.S. Pat. No. 7,109,312. "FET," as used herein, refers to "Fluorescence Energy Transfer." "FRET," as used herein, refers to "Fluorescence Resonance Energy Transfer." These terms are used herein to refer to both radiative and non-radiative energy transfer processes. For example, processes in which a photon is emitted and those involving long range electron transfer are included within these terms. Throughout this specification, both of these phenomena are subsumed under the general term "donor-acceptor energy transfer." "SNP" refers to "Single Nucleotide Polymorphism."

Definitions

The following definitions are broadly applicable to each of the embodiments of the present invention set forth hereinbelow. Unless defined otherwise, all technical and scientific terms used herein generally have the same meaning as commonly understood by one of ordinary skill in the art to which this invention belongs. Generally, the nomenclature used herein and the laboratory procedures in cell culture, molecular genetics, organic chemistry and nucleic acid chemistry and hybridization described below are those well known and commonly employed in the art. Standard techniques are used for nucleic acid and peptide synthesis. Molecular biological techniques and procedures are generally performed according to conventional methods in the art and various general references (see generally, Sambrook et al. MOLECULAR CLONING: A LABORATORY MANUAL, 2d ed. (1989) Cold Spring Harbor Laboratory Press, Cold Spring Harbor, N.Y., which is incorporated herein by reference). The nomenclature used herein and the laboratory procedures in analytical chemistry, and organic synthesis are those well known and commonly employed in the art. Standard techniques, or modifications thereof, are used for chemical syntheses and chemical analyses.

The term "alkyl," by itself or as part of another substituent, means, unless otherwise stated, a straight- or branched-chain, or cyclic hydrocarbon radical, or combination thereof, which may be fully saturated, mono- or polyunsaturated and can include mono-, di-, tri- and tetra-valent radicals, having the number of carbon atoms designated (i.e. $C_1$-$C_{10}$ means one to ten carbons). Examples of saturated hydrocarbon radicals include, but are not limited to, groups such as methyl, ethyl, n-propyl, isopropyl, n-butyl, t-butyl, isobutyl, sec-butyl, cyclohexyl, (cyclohexyl)methyl, cyclopropylmethyl, homologs and isomers of, for example, n-pentyl, n-hexyl, n-heptyl, n-octyl, and the like. An unsaturated alkyl group is one having one or more double bonds or triple bonds. Examples of unsaturated alkyl groups include, but are not limited to, vinyl, 2-propenyl, crotyl, 2-isopentenyl, 2-(butadienyl), 2,4-pentadienyl, 3-(1,4-pentadienyl), ethynyl, 1- and 3-propynyl, 3-butynyl, and the higher homologs and isomers. The term "alkyl," unless otherwise noted, also optionally include those derivatives of alkyl defined in more detail below, such as "heteroalkyl." Alkyl groups that are limited to hydrocarbon groups are termed "homoalkyl". The term "alkyl", as used herein refers to alkenyl and alkynyl moieties, each of which can be mono-, di- or polyvalent species as appropriate to satisfy valence requirements. Alkyl groups are optionally substituted, e.g., with one or more groups referred to herein as an "alkyl group substituent."

The term "alkylene" by itself or as part of another substituent means a divalent radical derived from an alkyl moiety, as exemplified, but not limited, by —$CH_2CH_2CH_2CH_2$—, and further includes those groups described below as "heteroalkylene." Typically, an alkyl (or alkylene) group will have from 1 to 24 carbon atoms, with those groups having 10 or fewer carbon atoms being preferred in the present invention. For alkylene and heteroalkylene linker groups, it is optional that no orientation of the linker group is implied by the direction in which the formula of the linker group is written. For example, the formula —$C(O)_2R'$— represents —$C(O)_2R'$— and, optionally, —$R'C(O)_2$—. A "lower alkyl" or "lower alkylene" is a shorter chain alkyl or alkylene group, generally having eight, seven, six, five or fewer carbon atoms.

The terms "alkoxy," "alkylamino" and "alkylthio" (or thioalkoxy) are used in their conventional sense, and refer to those alkyl groups attached to the remainder of the molecule via an oxygen atom, an amino group, or a sulfur atom, respectively.

The term "heteroalkyl," by itself or in combination with another term, means, unless otherwise stated, a stable straight- or branched-chain, or cyclic alkyl radical consisting of the stated number of carbon atoms and at least one heteroatom selected from the group consisting of B, O, N, Si and S, wherein the heteroatom may optionally be oxidized and the nitrogen atom may optionally be quaternized. The heteroatom(s) may be placed at any internal position of the heteroalkyl group or at a terminus of the chain, e.g., the position through which the alkyl group is attached to the remainder of the molecule. Examples of "heteroalkyl" groups include, but are not limited to, —$CH_2$—$CH_2$—O—$CH_3$, —$CH_2$—$CH_2$—NH—$CH_3$, —$CH_2$—$CH_2$—N($CH_3$)—$CH_3$, —$CH_2$—S—$CH_2$—$CH_3$, —$CH_2$—$CH_2$, —S(O)—$CH_3$, —$CH_2$—$CH_2$—S(O)$_2$—$CH_3$, —CH=CH—O—$CH_3$, —Si($CH_3$)$_3$, —$CH_2$—CH=N—$OCH_3$, and —CH=CH—N($CH_3$)—$CH_3$. Two or more heteroatoms may be consecutive, such as, for example, —$CH_2$—NH—$OCH_3$ and —$CH_2$—O—Si($CH_3$)$_3$. Similarly, the term "heteroalkylene" by itself or as part of another substituent refers to a substituted or unsubstituted divalent heteroalkyl radical, as exemplified, but not limited by, —$CH_2$—$CH_2$—S—$CH_2$—$CH_2$— and —$CH_2$—S—$CH_2$—$CH_2$—NH—$CH_2$—. For heteroalkylene groups, heteroatoms can also occupy either or both of the chain termini (e.g., alkyleneoxy, alkylenedioxy, alkyleneamino, alkylenediamino, and the like).

The terms "cycloalkyl" and "heterocycloalkyl", by themselves or in a combination with other terms, represent, unless otherwise stated, cyclic versions of "alkyl" and "heteroalkyl", respectively. Additionally, for heterocycloalkyl, a heteroatom can occupy the position at which the heterocycle is attached to the remainder of the molecule. Examples of cycloalkyl include, but are not limited to, cyclopentyl, cyclohexyl, 1-cyclohexenyl, 3-cyclohexenyl, cycloheptyl, and the like. Examples of heterocycloalkyl include, but are not limited to, 1-(1,2,5,6-tetrahydropyridyl), 1-piperidinyl, 2-piperidinyl, 3-piperidinyl, 4-morpholinyl, 3-morpholinyl, tetrahydrofuran-2-yl, tetrahydrofuran-3-yl, tetrahydrothien-2-yl, tetrahydrothien-3-yl, 1-piperazinyl, 2-piperazinyl, and the like.

The terms "halo" or "halogen," by themselves or as part of another substituent, mean, unless otherwise stated, a fluorine, chlorine, bromine, or iodine atom. Additionally, terms such as "haloalkyl," are meant to include monohaloalkyl and polyhaloalkyl. For example, the term "halo($C_1$-$C_4$)alkyl" is meant to include, but not be limited to, trifluoromethyl, 2,2,2-trifluoroethyl, 4-chlorobutyl, 3-bromopropyl, and the like.

The term "aryl" means, unless otherwise stated, a polyunsaturated, aromatic, substituent that can be a single ring or multiple rings (preferably from 1 to 3 rings, one or more of which is optionally a cycloalkyl or heterocycloalkyl), which are fused together or linked covalently. The term "heteroaryl" refers to aryl groups (or rings) that contain from one to four heteroatoms selected from N, O, and S, wherein the nitrogen and sulfur atoms are optionally oxidized, and the nitrogen atom(s) are optionally quaternized. A heteroaryl group can be attached to the remainder of the molecule through a heteroatom. Non-limiting examples of aryl and heteroaryl groups include phenyl, 1-naphthyl, 2-naphthyl, 4-biphenyl, 1-pyrrolyl, 2-pyrrolyl, 3-pyrrolyl, 3-pyrazolyl, 2-imidazolyl, 4-imidazolyl, pyrazinyl, 2-oxazolyl, 4-oxazolyl, 2-phenyl-4-oxazolyl, 5-oxazolyl, 3-isoxazolyl, 4-isoxazolyl, 5-isoxazolyl, 2-thiazolyl, 4-thiazolyl, 5-thiazolyl, 2-furyl, 3-furyl, 2-thienyl, 3-thienyl, 2-pyridyl, 3-pyridyl, 4-pyridyl, 2-pyrimidyl, 4-pyrimidyl, 5-benzothiazolyl, purinyl, 2-benzimidazolyl, 5-indolyl, 1-isoquinolyl, 5-isoquinolyl, 2-quinoxalinyl, 5-quinoxalinyl, 3-quinolyl, and 6-quinolyl. Substituents for each of the above noted aryl and heteroaryl ring systems are selected from the group of "aryl group substituents" described below.

For brevity, the term "aryl" when used in combination with other terms (e.g., aryloxy, arylthioxy, arylalkyl) optionally includes both homoaryl and heteroaryl rings as defined above. Thus, the term "arylalkyl" optionally includes those radicals in which an aryl group is attached to an alkyl group (e.g., benzyl, phenethyl, pyridylmethyl and the like) including those alkyl groups in which a carbon atom (e.g., a methylene group) has been replaced by, for example, an oxygen atom (e.g., phenoxymethyl, 2-pyridyloxymethyl, 3-(1-naphthyloxy)propyl, and the like).

Substituents for the alkyl and heteroalkyl radicals (including those groups often referred to as alkylene, alkenyl, heteroalkylene, heteroalkenyl, alkynyl, cycloalkyl, heterocycloalkyl, cycloalkenyl, and heterocycloalkenyl) are generically referred to as "alkyl group substituents," and they can be one or more of a variety of groups selected from, but not limited to: —OR', =O, =NR', =N—OR', —NR'R", —SR', -halogen, —SiR'R"R''', —OC(O)R', —C(O)R', —CO$_2$R', —CONR'R", —OC(O)NR'R", —NR"C(O)R', —NR'—C(O)NR"R''', —NR"C(O)$_2$R', —NR—C(NR'R"R''')=NR'''', —NR—C(NR'R")=NR''', —S(O)R', —S(O)$_2$R', —S(O)$_2$NR'R", —NRSO$_2$R', —CN and —NO$_2$ in a number ranging from zero to (2 m'+1), where m' is the total number of carbon atoms in such radical. R', R", R''' and R'''' each preferably independently refer to hydrogen, substituted or unsubstituted heteroalkyl, substituted or unsubstituted aryl, e.g., aryl substituted with 1-3 halogens, substituted or unsubstituted alkyl, alkoxy or thioalkoxy groups, or arylalkyl groups. When a compound of the invention includes more than one R group, for example, each of the R groups is independently selected as are each R', R", R''' and R'''' groups when more than one of these groups is present. When R' and R" are attached to the same nitrogen atom, they can be combined with the nitrogen atom to form a 5-, 6-, or 7-membered ring. For example, —NR'R" is meant to include, but not be limited to, 1-pyrrolidinyl and 4-morpholinyl. From the above discussion of substituents, one of skill in the art will understand that the term "alkyl" includes groups with carbon atoms bound to groups other than hydrogen, such as haloalkyl (e.g., —CF$_3$ and —CH$_2$CF$_3$) and acyl (e.g., —C(O)CH$_3$, —C(O)CF$_3$, —C(O)CH$_2$OCH$_3$, and the like). Exemplary alkyl group substituents include those groups referred to herein as "reactive functional groups" and "linkage fragments." In various embodiments, the alkyl group substituent is a phosphorus-containing moiety, e.g., a phosphodiester or a phosphodiester modification such as those described herein.

Similar to the substituents described for the alkyl radical, substituents for the aryl and heteroaryl groups are generically referred to as "aryl group substituents." Exemplary substituents are selected from the list of alkyl group substituents and others, for example: halogen, —OR', =O, =NR', =N—NR', —NR'R", —SR', —SiR'R"R''', —OC(O)R', —C(O)R', —CO$_2$R', —CONR'R", —OC(O)NR'R", —NR"C(O)R', —NR'—C(O)NR"R''', —NR"C(O)$_2$R', —NR—C(NR'R"R''')=NR'''', —NR—C(NR'R")=NR''', —S(O)R', —S(O)$_2$R', —S(O)$_2$NR'R", —NRSO$_2$R', —CN and —NO$_2$, —R', —N$_3$, —CH(Ph)$_2$, fluoro($C_1$-$C_4$)alkoxy, and fluoro($C_1$-$C_4$)alkyl, in a number ranging from zero to the total number of open valences on the aromatic ring system; and where R', R", R''' and R'''' are preferably independently selected from hydrogen, substituted or unsubstituted alkyl, substituted or unsubstituted heteroalkyl, substituted or unsubstituted aryl and substituted or unsubstituted heteroaryl. When a compound of the invention includes more than one R group, for example, each of the R groups is independently selected as are each R', R", R''' and R'''' groups when more than one of these groups is present.

Two of the substituents on adjacent atoms of the aryl or heteroaryl ring may optionally be replaced with a substituent of the formula -T-C(O)—(CRR')$_q$—U—, wherein T and U are independently —NR—, —O—, —CRR'— or a single bond, and q is an integer from 0 to 3. Alternatively, two of the substituents on adjacent atoms of the aryl or heteroaryl ring may optionally be replaced with a substituent of the formula -A-(CH$_2$)$_r$—B—, wherein A and B are independently —CRR'—, —O—, —NR—, —S—, —S(O)—, —S(O)$_2$—, —S(O)$_2$NR'— or a single bond, and r is an integer of from 1 to 4. One of the single bonds of the new ring so formed may optionally be replaced with a double bond. Alternatively, two of the substituents on adjacent atoms of the aryl or heteroaryl ring may optionally be replaced with a substituent of the formula —(CRR')$_s$—X—(CR"R''')$_d$—, where s and d are independently integers of from 0 to 3, and X is —O—, —NR'—, —S—, —S(O)—, —S(O)$_2$—, or —S(O)$_2$NR'—. The substituents R, R', R" and R''' are preferably independently selected from hydrogen or substituted or unsubstituted ($C_1$-$C_{16}$)alkyl. Exemplary aryl group substituents include those groups referred to herein as "reactive functional groups" and "linkage fragments."

As used herein, the term "heteroatom" includes oxygen (O), nitrogen (N), sulfur (S) and silicon (Si).

The symbol "R" is a general abbreviation that represents a substituent group that is selected from H, substituted or unsubstituted alkyl, substituted or unsubstituted heteroalkyl, substituted or unsubstituted aryl, substituted or unsubstituted heteroaryl, and substituted or unsubstituted heterocyclyl groups. R can also refer to alkyl group substituents and aryl group substituents.

The term "salt(s)" includes salts of the compounds which are prepared with relatively nontoxic acids or bases, depending on the particular substituents found on the compounds described herein. When compounds of the present invention contain relatively acidic functionalities, base addition salts can be obtained by contacting the neutral form of such compounds with a sufficient amount of the desired base, either neat or in a suitable inert solvent. Examples of base addition salts include sodium, potassium, calcium, ammonium, organic amino, or magnesium salt, or a similar salt. When compounds of the present invention contain relatively basic functionalities, acid addition salts can be obtained by contacting the neutral form of such compounds with a sufficient amount of the desired acid, either neat or in a suitable inert solvent. Examples of acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids, and the like, as well as the salts derived from relatively nontoxic organic acids like acetic, propionic, isobutyric, butyric, maleic, malic, malonic, benzoic, succinic, suberic, fumaric, lactic, mandelic, phthalic, benzenesulfonic, p-tolylsulfonic, citric, tartaric, methanesulfonic, and the like. Also included are salts of amino acids such as arginate, and the like, and salts of organic acids like glucuronic or galactunoric acids and the like (see, for example, Berge et al., *Journal of Pharmaceutical Science*, 66: 1-19 (1977)). Certain specific compounds of the present invention contain both basic and acidic functionalities that allow the compounds to be converted into either base or acid addition salts. Hydrates of the salts are also included.

As used herein, "nucleic acid" means nucleosides, nucleotides and oligonucleotides, e.g., DNA, RNA, whether single-stranded, double-stranded, or in more highly aggregated hybridization motifs, and any chemical modifications thereof. Modifications include, but are not limited to, those providing chemical groups that incorporate additional charge, polarizability, hydrogen bonding, electrostatic interaction, and fluxionality to the nucleic acid ligand bases or to the nucleic acid ligand as a whole. Such modifications include, but are not limited to, peptide nucleic acids (PNAs), phosphodiester group modifications (e.g., phosphorothioates, methylphosphonates), sugar modifications, 5-position pyrimidine modifications, 8-position purine modifications, modifications at exocyclic amines, substitution of 4-thiouridine, substitution of 5-bromo or 5-iodo-uracil; backbone modifications, methylations (e.g., 5' and/or 3'), unusual base-pairing combinations such as the isobases, isocytidine and isoguanidine and the like. Nucleic acids can also include non-natural bases. A "nucleomonomer" refers to a single nucleic acid unit, which can be a nucleoside, nucleotide or a modification thereof.

"Base" as used herein includes those moieties which contain not only the known purine and pyrimidine heterocycles and the invention pyrimidines, but also heterocycle analogs and tautomers thereof. Purines include adenine, guanine and xanthine and exemplary purine analogs include 8-oxo-$N^6$-methyladenine and 7-deazaxanthine. Pyrimidines include uracil and cytosine and their analogs such as 5-methylcytosine, 5-methyluracil and 4,4-ethanocytosine. This term also encompasses non-natural bases. Representative non-natural bases include 5-fluorouracil, 5-bromouracil, 5-chlorouracil, 5-iodouracil, hypoxanthine, xanthine, 4-acetylcytosine, 5-(carboxyhydroxylmethyl)uracil, 5-carboxymethylaminomethyl-2-thiouridine, 5-carboxymethylaminomethyluracil, dihydrouracil, beta-D-galactosylqueosine, inosine, $N^6$-isopentenyladenine, 1-methylguanine, 1-methylinosine, 2,2-dimethylguanine, 2-methyladenine, 2-methylguanine, 3-methylcytosine, 5-methylcytosine, $N^6$-adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-$N^6$-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methyl ester, uracil-5-oxyacetic acid (v), 5-methyl-2-thiouracil, 3-(3-amino-3-N-2-carboxypropyl) uracil, (acp3)w, nitroindole, and 2,6-diaminopurine.

In various embodiments, the inventive compounds include pyrimidines derivatized at the 5-position. The derivatives are 1-alkenyl-, 1-alkynyl-, heteroaromatic- and 1-alkynyl-heteroaromatic modifications. "1-Alkenyl" means an olefinically-unsaturated (double bond containing) acyclic group. "1-Alkynyl" means an acetylenically-unsaturated (triple bond containing) acylic group As used herein, "nucleoside" means a subset of nucleic acid in which a base is covalently attached to a sugar or sugar analog and which optionally includes a phosphite, phosphoramidite or phosphine. The term nucleoside includes ribonucleosides, deoxyribonucleosides, or any other nucleoside which is an N-glycoside or C-glycoside of a base. The stereochemistry of the sugar carbons can be other than that of D-ribose. Nucleosides also include those species which contain modifications of the sugar moiety, for example, wherein one or more of the hydroxyl groups are replaced with a halogen, a heteroatom, an aliphatic groups, or are functionalized as ethers, amines, thiols, and the like. The pentose moiety can be replaced by a hexose or an alternate structure such as a cyclopentane ring, a 6-member morpholino ring and the like. Nucleosides as defined herein also include a base linked to an amino acid and/or an amino acid analog having a free carboxyl group and/or a free amino group and/or protected forms thereof. Nucleosides also optionally include one or more base modification, e.g., modified with a fluorocarbyl, alkenyl or alkynyl moiety. A nucleoside including a phosphodiester or phosphodiester modification, is referred to herein as a nucleotide.

"Sugar modification," as used herein, means any pentose or hexose moiety other than 2'-deoxyribose. Modified sugars include, for example, D-ribose, 2'-O-alkyl, 2'-amino, 2'-halo functionalized pentoses, hexoses and the like. Exemplary sugar modifications include those sugars in which one or more of the hydroxyl groups is replaced with a halogen, a heteroatom, an alkyl moiety, or are functionalized as ethers, esters, and the like. The pentose moiety can be replaced by a hexose or an alternate structure such as a cyclopentane ring, a 6-member morpholino ring and the like. Nucleosides as defined herein are also intended to include a base linked to an amino acid and/or an amino acid analog having a free carboxyl group and/or a free amino group and/or protected forms thereof. Sugars having a stereochemistry other than that of a D-ribose are also included.

"Phosphodiester group modification" means any analog of the native phosphodiester group that covalently couples adjacent nucleomonomers. Substitute linkages include phosphodiester analogs, e.g. such as phosphorothioate and methylphosphonate, and nonphosphorus containing linkages, e.g. such as acetals and amides.

Nucleic acid modification also include 3' and 5' modifications such as capping with a quencher (e.g., a BHQ), a fluorophore, intercalator, minor groove binder, a fluorocarbon, a conformationally assisted stabilizing group or another moiety. In various embodiments, the capping group is covalently conjugated to the oligomer through a linker group.

Oligomers are defined herein as two or more nucleomonomers covalently coupled to each other by a phosphodiester or modified phosphodiester moiety. Thus, an oligomer can have as few as two nucleomonomers (a dimer), and have essentially no upper limit of nucleomonomers. Oligomers can be binding competent and, thus, can base pair with cognate single-stranded or double-stranded (or higher order aggregation) nucleic acid sequences. Oligomers are also useful as synthons for longer oligomers as described herein. Oligomers can also contain abasic sites and pseudonucleotides. In various embodiments, the oligomers of the invention are functionalized. The moieties functionalizing the oligomers are discussed below. In describing certain embodiments the term "oligomer" is used interchangeably to refer to the nucleic acid sequence of the oligomer, the modified nucleic acid sequence providing a probe or the modified nucleic acid sequence provident a solid support of the invention "Peptide" refers to an oligomer in which the monomers are amino acids and are joined together through amide bonds, alternatively referred to as a polypeptide. When the amino acids are α-amino acids, either the L-optical isomer or the D-optical isomer can be used. Additionally, unnatural amino acids, for example, β-alanine, phenylglycine and homoarginine are also included. Commonly encountered amino acids that are not gene-encoded may also be used in the present invention. All of the amino acids used in the present invention may be either the D- or L-isomer. The L-isomers are generally preferred. In addition, other peptidomimetics are also useful in the present invention. For a general review, see, Spatola, A. F., in CHEMISTRY AND BIOCHEMISTRY OF AMINO ACIDS, PEPTIDES AND PROTEINS, B. Weinstein, eds., Marcel Dekker, New York, p. 267 (1983).

A "solid support" is a solid material having a surface for attachment of molecules, compounds, cells, or other entities, or to which surface such species are attached. The surface of a solid support can be flat or otherwise configured. A solid support can be porous or non-porous. A solid support can be a chip or array that comprises a surface, and that may comprise glass, silicon, nylon, polymers, plastics, ceramics, or metals. A solid support can also be a membrane, such as a nylon, nitrocellulose, or polymeric membrane, or a plate or dish and can be comprised of glass, ceramics, metals, or plastics, such as, for example, a 96-well plate made of, for example, polystyrene, polypropylene, polycarbonate, or polyallomer. A solid support can also be a bead or particle of any shape, and is preferably spherical or nearly spherical, and preferably a bead or particle has a diameter or maximum width of 1 millimeter or less, more preferably of between 0.1 to 100 microns. Such particles or beads can be comprised of any suitable material, e.g., glass or ceramics, and/or one or more polymers, such as, for example, nylon, polytetrafluoroethylene, TEFLON™, polystyrene, polyacrylamide, sepaharose, agarose, cellulose, cellulose derivatives, or dextran, and/or can comprise metals, particularly paramagnetic metals, such as iron.

Supports for solid phase synthesis are known in the art and include, but are not limited to, high cross-linker polystyrene (McCollum, et al., *Tetrahedron Lett.* 32: 4069-4072 (1991), polystyrene/PEG copolymer (Gao, et al., *Tetrahedron Lett.* 32: 5477-5480 (1991), silica gel (Chow, et al., *Nucl. Acids Res.* 9: 2807-2817 (1981)), polyamide bonded silica gel (Gait, et al. *Nucl Acids Res.* 10: 6243-6254 (1982)), cellulose (Crea, et al., *Nucl. Acids Res.* 8: 2331-2348 (1980)), (and controlled pore glass (CPG) (Koster, et al., *Tetrahedron Lett.* 24: 747-750 (1983). An exemplary solid support is CPG beads. CPG beads can be derivatized for the attachment of a nucleomonor or oligomer in a variety of ways. For example, CPG beads can be treated with 3-aminopropyltriethoxysilane to add an amino propyl linker handle for the attachment of oligonucleotide analogue monomers or dimers (Koster, et al., *Tetrahedron Lett.* 24: 747-750 (1983), or, preferably, a long-chain alkylamine group, most preferably including a terminal nucleoside, can be attached to CPG (Adams, et al., *J. Am. Chem. Soc.* 105: 661-663 (1983)). Supports for oligonucleotide synthesis or peptide synthesis, for example dT-LCAA-CPG (Applied Biosystems), are commercially available.

An "intercalator" refers to a planar aromatic or heteroaromatic moiety that is capable of partial insertion and stacking between adjacent nucleobases. These moieties may be small molecules or part of a larger entity, such as a protein. Non-limiting examples of intercalators include acridines, anthracenes, anthracyclines, anthracyclinone, methylene blue, indole, anthraquinone, quinoline, isoquinoline, dihydroquinones, tetracyclines, psoralens, coumarins, ethidium halides, ethidium homodimers, homodimeric oxazole yellow (YOYO), thiazole orange (TOTO), dynemicins, 1,10-phenanthroline-copper, calicheamicin, porphyrins, distamycins, netropcins, and viologens.

A "minor groove binder" refers to a moiety typically having a molecular weight of approximately 150 to approximately 2000 Daltons. The moiety binds in a non-intercalating manner into the minor groove of double stranded (or higher order aggregation) DNA, RNA or hybrids thereof, preferably, with an association constant greater than approximately $10^3$ $M^{-1}$. Minor groove binding compounds have widely varying chemical structures, however, exemplary minor groove binders have a crescent shape three dimensional structure. Exemplar include certain naturally occurring compounds such as netropsin, distamycin and lexitropsin, mithramycin, chromomycin $A_3$, olivomycin, anthramycin, sibiromycin, as well as further related antibiotics and synthetic derivatives. Certain bisquarternary ammonium heterocyclic compounds, diarylamidines such as pentamidine, stilbamidine and berenil, CC-1065 and related pyrroloindole and indole polypeptides, Hoechst 33258, 4'-6-diamidino-2-phenylindole (DAPI) as well as a number of oligopeptides consisting of naturally occurring or synthetic amino acids are minor groove binder compounds. Exemplary minor groove binders are described in U.S. Pat. No. 6,084,102. This type of binding can be detected by well established spectrophotometric methods, such as ultraviolet (u.v.) and nuclear magnetic resonance (nmr) spectroscopy and also by gel electrophoresis. Shifts in u.v. spectra upon binding of a minor groove binder molecule, and nmr spectroscopy utilizing the "Nuclear Overhauser" (NOSEY) effect are particularly well known and useful techniques for this purpose. Gel electrophoresis detects binding of a minor groove binder to double stranded DNA or fragment thereof, because upon such binding the mobility of the double stranded DNA changes.

The minor groove binder is typically attached to the oligomer or solid support through a linker comprising a chain about 20, about 15 atoms, about 10 or about 5 atoms.

Intercalating moieties or agents are readily distinguished from minor groove binders on the basis that the intercalating agents are flat aromatic (preferably polycyclic) molecules versus the "crescent shape" or analogous geometry of the minor groove binders. An experimental distinction can also be made by nmr spectroscopy utilizing the Nuclear Overhauser effect.

The term "linker" or "L", as used herein, refers to a single covalent bond ("zero-order") or a series of stable covalent bonds incorporating 1-30 nonhydrogen atoms selected from the group consisting of C, N, O, S, Si and P that covalently link together the components of the compounds of the invention, e.g., linking a solid support to a stabilizing agent, a quencher, a nucleomonor or oligomer of the invention; or linking a quencher or stabilizing moiety to a base in an amidite of the invention. Exemplary linkers include 1, 2, 3, 4, 5, 6, 7, 8, 9, 10, 11, 12, 13, 14, 15, 16, 17, 18, 19, 20, 21, 22, 23, 24, 25, 26, 27, 28, 29 or non-hydrogen atoms. Unless otherwise specified, "linking," "linked," "linkage," "conjugating," "conjugated" and analogous terms relating to attachment refer to techniques utilizing and species incorporating linkers. Exemplary linkers include a linkage fragment as defined herein. Moreover, a linker is of use to attach an oligomer or nascent oligomer (during oligomer synthesis) to the solid support of the invention. Thus, the invention also provides an oligomer of the invention covalently attached to a solid support (e.g., a solid support of the invention) through a linker. The solid supports and oligomers of the invention optionally include a cleavable linker between two components of the solid support and oligomer (e.g., between the oligomer and the solid support, between the fluorophore and oligomer, between the quencher and oligomer, between the fluorophore and quencher, etc.). In various embodiments, the linker joining the solid support to the oligomer is a cleavable linker.

A "cleavable linker" is a linker that has one or more cleavable groups that may be broken by the result of a reaction or condition. An exemplary cleavable linker is located within $L^2$ of Formula I, serving to allow for the expedient separation of a synthesized oligomer of the invention from the solid support upon which it was synthesized. The term "cleavable group" refers to a moiety that allows for release of a component of the solid support or oligomer of the invention by cleaving a bond linker the released moiety to the remainder of the conjugate. Exemplary cleavage mechanisms of use both in preparing and using the oligomers and solid supports of the invention are enzymatically or otherwise chemically mediated.

In addition to enzymatically cleavable groups, it is within the scope of the present invention to include one or more sites that are cleaved by the action of an agent other than an enzyme. Exemplary non-enzymatic cleavage agents include, but are not limited to, acids, bases, light (e.g., nitrobenzyl derivatives, phenacyl groups, ortho-hydroxycinnamate esters, benzoin esters), and heat. Many cleaveable groups are known in the art. See, for example, Jung et al., Biochem. Biophys. Acta, 761: 152-162 (1983); Joshi et al., J. Biol. Chem., 265: 14518-14525 (1990); Zarling et al., J. Immunol., 124: 913-920 (1980); Bouizar et al., Eur. J. Biochem., 155: 141-147 (1986); Park et al., J. Biol. Chem., 261: 205-210 (1986); Browning et al., J. Immunol., 143: 1859-1867 (1989). Moreover a broad range of cleavable, bifunctional (both homo- and hetero-bifunctional) spacer arms are commercially available.

An exemplary cleavable group is cleavable by a reagent, e.g. sodium hydroxide, ammonia or other amine. In various embodiments the cleavable linker is readily cleaved at room temperature or under microwave conditions. In one embodiment, the cleavable linker is $L^2$ and it is cleaved by treatment with an amine, e.g., ammonia or an essentially anhydrous amine in an organic solvent.

A "linkage fragment," is a moiety that links two or more components (e.g., functional component, solid support or linker). This term refers to a covalent bond that is formed by reaction of complementary reaction partners, each of which has a reactive functional group of reactivity complementary to the reactivity of its partner. Linkage fragments in the solid support and oligomers of the invention are independently selected. Exemplary linkage fragments include, but are not limited to S, SC(O)NH, HNC(O)S, SC(O)O, O, NH, NHC(O), (O)CNH and NHC(O)O, and OC(O)NH, $CH_2S$, $CH_2O$, $CH_2CH_2O$, $CH_2CH_2S$, $(CH_2)_oO$, $(CH_2)_oS$ or $(CH_2)_oY^x$-PEG wherein, $Y^x$ is S, NH, NHC(O), C(O)NH, NHC(O)O, OC(O)NH, or O and o is an integer from 1 to 50. In each of these exemplary linkage fragments, NH can be $NR^r$, in which $R^r$ is substituted or unsubstituted alkyl or substituted or unsubstituted heteroalkyl. A linkage fragment can also be a phosphodiester or phosphodiester modification. In various embodiments, the linkage fragment is between a linker and a fluorophore, a linker and a quencher, a linker and a stabilizing moiety or a linker and a solid support. In an exemplary embodiment of the solid support and oligomers of the invention, each linkage fragment is a different linkage fragment.

The term "fluorophore" as used herein refers to a moiety that is inherently fluorescent or demonstrates a change in fluorescence upon binding to a biological compound or metal ion, or metabolism by an enzyme, i.e., fluorogenic. Fluorophores may be substituted to alter the solubility, spectral properties or physical properties of the fluorophore. Numerous fluorophores are known to those skilled in the art and include, but are not limited to coumarins, acridines, furans, dansyls, cyanines, pyrenes, naphthalenes, benzofurans, quinolines, quinazolinones, indoles, benzazoles, borapolyazaindacene, oxazines and xanthenes, with the latter including fluoresceins, rhodamines, rosamines and rhodols. These and other fluorophores of use in the invention are described in Haugland, MOLECULAR PROBES HANDBOOK OF FLUORESCENT PROBES AND RESEARCH CHEMICALS. Further useful fluorophores are described in commonly owned U.S. Patent Application Publication No. 2005/0214833 and 2005/0170363 and herein below.

As used herein, "quencher" refers to any fluorescence-modifying moiety of the invention that can attenuate at least partly the light emitted by a fluorophore. This attenuation is referred to herein as "quenching". Hence, in various embodiments, excitation of the fluorophore in the presence of the quenching group leads to an emission signal that is less intense than expected, or even completely absent. Quenching typically occurs through energy transfer between the excited fluorophore and the quenching group.

The fluorophore or quencher may include substituents enhancing a desirable property, e.g., solubility in water, cell permeability and spectral absorption and emission, relative to the "parent" compound in the absence of such substituent. As such the fluorophore or quencher of use in the invention include substituents that enhance a desirable property relative to an identical parent compound in the absence of the improving substituent.

A "functional component" is a generic term for a moiety in a compound of the invention having a structure selected from a quencher, a fluorophore and a stabilizing moiety (including, but not limited to, intercalators, minor groove binding moieties, bases modified with a stabilizing moiety (e.g., alkynyl moieties, and fluoroalkyl moieties), and conformational stabilizing moieties, such as those described in commonly owned U.S. Patent Application Publication No. 2007/0059752).

The expression "amplification of polynucleotides" includes but is not limited to methods such as polymerase chain reaction (PCR), ligation amplification (or ligase chain reaction, LCR) and amplification methods based on the use of Q-beta replicase. These methods are well known and widely practiced in the art. See, e.g., U.S. Pat. Nos. 4,683,195 and 4,683,202 and Innis et al., 1990 (for PCR); and Wu et al., 1989a (for LCR). Reagents and hardware for conducting PCR are commercially available. Primers useful to amplify sequences from a particular gene region are preferably complementary to, and hybridize specifically to sequences in the target region or in its flanking regions. Nucleic acid sequences generated by amplification may be sequenced directly. Alternatively the amplified sequence(s) may be cloned prior to sequence analysis. A method for the direct cloning and sequence analysis of enzymatically amplified genomic segments has been described by Scharf (1986). The present invention provides oligomeric primers of use in amplification processes. Moreover, there is provided a solid support of use in synthesizing such primers. In addition to primers, the invention provides probes, and methods of using such probes, to detect, characterize and/or quantify the products of amplification: also provided are solid supports of use to synthesize these oligomeric probes.

The term "base-stacking perturbations" refers to any event that causes a perturbation in base-stacking such as, for example, a base-pair mismatch, a protein binding to its recognition site, or any other entities that form oligonucleotide adducts. Various probes of the invention are capable of detecting, characterizing and/or quantifying such base-stacking perturbations. Moreover, the invention provides solid supports of use in synthesizing probes capable of detecting, characterizing and/or quantifying such base-stacking perturbations.

The term "hybridized" refers to two nucleic acid strands associated with each other which may or may not be fully base-paired: generally, this term refers to an association including an oligomer of the invention whether bound to a solid support or in solution.

The term "denaturing" refers to the process by which strands of nucleic acid duplexes (or higher aggregation) are no longer base-paired by hydrogen bonding and are separated into single-stranded molecules. Methods of denaturation are well known to those skilled in the art and include thermal denaturation and alkaline denaturation. This term generally refers to the dissociation of a probe of the invention from its target nucleic acid.

The term "mismatches" refers to nucleic acid bases within hybridized nucleic acid duplexes (or higher aggregation) which are not 100% complementary. A mismatch includes any incorrect pairing between the bases of two bases located on complementary strands of nucleic acid that are not the Watson-Crick base-pairs, e.g., A:T or G:C. The lack of total homology may be due to deletions, insertions, inversions, substitutions or frameshift mutations. In various embodiments, the oligomer of the invention includes a mismatch relative to its target nucleic acid, preferably allowing detection and/or characterization and/or quantification of the corresponding mismatch in its target. In certain embodiments, the mismatch is a single nucleotide mismatch.

As used herein, the term "polymorphism" refers to a sequence variation in a gene, and "mutation" refers to a sequence variation in a gene that is associated or believed to be associated with a phenotype. The term "gene" refers to a segment of the genome coding for a functional product protein control region. Polymorphic markers used in accordance with the present invention for subject identification may be located in coding or non-coding regions of the genome, and various probes of the invention are designed to hybridize to nucleic acid regions including these markers. The term "subject," as used herein refers to a subject providing a test sample from which target nucleic acids are obtained for the purpose of genetic testing. The oligomers of the invention are of use in detecting and/or characterizing and/or quantifying polymorphisms and mutations. Moreover, the solid supports of the invention are of use in synthesizing oligomers of use to detect and/or characterize and/or quantitate polymorphisms and mutations.

The term "probe" as used herein refers to nucleic acid oligomers prepared using a solid support or amidite of the invention. In various embodiments, the probes produce a detectable response upon interaction with a binding partner. The probes include at least one detectable moiety, or a pair of moieties that form an energy transfer pair detectable upon some change of state of the probe in response to its interaction with a binding partner. The present invention provides probes and amidites and solid supports of use to synthesize probes. Exemplary probes of the invention are of use to detect a polymorphism. In various embodiments, the polymorphism is a single nucleic acid polymorphism (SNP).

The term "detectable response" as used herein refers to a change in or an occurrence of, a signal that is directly or indirectly detectable either by observation or by instrumentation and the presence of or, preferably, the magnitude of which is a function of the presence of a target binding partner for a probe in the test sample. Typically, the detectable response is an optical response from a fluorophore resulting in a change in the wavelength distribution patterns or intensity of absorbance or fluorescence or a change in light scatter, fluorescence quantum yield, fluorescence lifetime, fluorescence polarization, a shift in excitation or emission wavelength or a combination of the above parameters. The detectable change in a given spectral property is generally an increase or a decrease. However, spectral changes that result in an enhancement of fluorescence intensity and/or a shift in the wavelength of fluorescence emission or excitation are also useful. The change in fluorescence on ion binding is usually due to conformational or electronic changes in the indicator that may occur in either the excited or ground state of the fluorophore, due to changes in electron density at the ion binding site, due to quenching of fluorescence by the bound target metal ion, or due to any combination of these or other effects. Alternatively, the detectable response is an occurrence of a signal wherein the fluorophore is inherently fluorescent and does not produce a change in signal upon binding to a metal ion or biological compound. The present invention provides probes providing a detectable response and solid supports of use to synthesize such probes.

Introduction

The present invention provides phosphoramidites, solid supports and oligomers of a format readily prepared on these solid supports. Exemplary oligomers are stabilized with respect to their ability to hybridize to target nucleic acid sequences, forming duplexes or triplexes. Various oligomers of the invention are suitable for binding to DNA duplex target sequences via either CT or GT triple helix binding motif.

In various embodiments, the oligomers of the invention are resistant to nuclease degradation relative to an oligodeoxynucleotide having no modifications. Nuclease resistant oligomers of the invention are advantageously used under conditions where nucleases are present. For certain applications, such as modulation of gene expression by via an antisense mechanism, nuclease stability by oligomers of the invention is an important functional aspect of the oligomer.

An additional aspect of the invention includes methods of detecting the presence, absence or amount of a particular single-stranded DNA or RNA or a particular target duplex in a biological (or other) sample using the oligomers of the invention, to detect selected nucleic acid sequences. Such sequences can be associated with the presence of neoplastic growth, viruses or disease conditions.

Exemplary oligomers of the invention have enhanced binding properties with respect to complementary single-stranded and double-stranded nucleic acid sequences as compared to unmodified oligomers not having the stabilizing moiety component of the oligomers of the invention. In various embodiments, triple helix structures can be formed at physiological pH levels of 7.0 and higher. Improved duplex formation is also provided, in exemplary embodiments.

The invention provides oligomers useful for, in exemplary embodiments, (1) modulating gene expression in cells in vitro including cells grown in tissue culture (e.g., to treat a condition, e.g., cancer, infection, etc.), and (2) detecting and/or quantitating target nucleic acid sequences.

The invention is also directed to reagents and kits comprising the phosphoramidites, solid supports and/or oligomers of the invention.

The Embodiments

In an exemplary embodiment, the invention provides a compound having a structure according to Formula I:

$$X^a-L^1-Y^a\begin{matrix}L^2-Z^a\\ \\L^3-Q\\|\\OR^c\end{matrix} \quad (I)$$

wherein $X^a$ is a stabilizing moiety selected from fluoroalkyl, substituted or unsubstituted aryl and substituted or unsubstituted heteroaryl. In various embodiments, $X^a$ is a minor groove binder or an intercalating agent.

The symbols $L^1$, $L^2$, $L^3$ and $L^4$ represent linkers. The linkers are independently selected from a single covalent bond, substituted or unsubstituted alkyl and substituted or unsubstituted heteroalkyl moieties. $Y^a$ is a member selected from $CR^a$, and N in which $R^a$ is a member selected from H, substituted or unsubstituted alkyl and substituted or unsubstituted heteroalkyl. $R^a$ is optionally a linker to a functional component.

The symbol $Z^a$ represents a solid support, $OR^b$ or $NR^bR^{b'}$ in which $R^b$ and $R^{b'}$ are members independently selected from H, substituted or unsubstituted alkyl and substituted or unsubstituted heteroalkyl. The symbol $R^c$ represents a member selected from H, substituted or unsubstituted alkyl, substituted or unsubstituted heteroalkyl, substituted or unsubstituted aryl, substituted or unsubstituted heteroaryl and a phosphorus-containing linker covalently bound to a nucleic acid. In an exemplary embodiment, $R^c$ is a nucleic acid protecting group, e.g., dimethoxytrityl ("DMT"). In another embodiment, $R^c$ is a phosphodiester linker to another nucleic acid moiety, which is optionally derivatized with one or more functional component.

The compounds of the invention include a quencher of fluorescence energy. The quencher is represented by the symbol Q and, in exemplary embodiments, includes one or more of the following structural features:
  (a) at least three residues, each independently selected from substituted or unsubstituted aryl, and substituted or unsubstituted heteroaryl, wherein the first residue is covalently linked to the second residue via a first exocyclic diazo bond. The first or the second residue is covalently linked to a third residue through a second diazo bond; and
  (b) at least two residues, each independently selected from substituted or unsubstituted aryl, and substituted or unsubstituted heteroaryl. The first residue is covalently linked to the second residue via an exocyclic diazo bond, and at least one the residues is a member selected from substituted or unsubstituted polycyclic aryl and substituted or unsubstituted polycyclic heteroaryl groups.

The quenchers are linked to the remainder of the compound of the invention via a linker. The quencher and the linker are coupled by reaction of a reactive functional group on a precursor quencher and a reactive functional group on the linker. The two reactive functional groups are of complementary reactivity and upon reaction form a linkage fragment as defined herein.

Exemplary linkers in Formula I include:
For $L^1$, for example in which z is an integer from 1 to 20, such as 1, 2, 3, 4, 5, 6, 7, 8, 9, 10, 11, 12, 13, 14, 15, 16, 17, 18, 19 or 20.

For $L^2$, for example in which y, w and u are independently selected integers from 1 to 20, such as 1, 2, 3, 4, 5, 6, 7, 8, 9, 10, 11, 12, 13, 14, 15, 16, 17, 18, 19 or 20.

For $L^3$, for example in which v, t and s are independently selected integers from 1 to 20, such as 1, 2, 3, 4, 5, 6, 7, 8, 9, 10, 11, 12, 13, 14, 15, 16, 17, 18, 19 or 20. The symbol $X^b$ represents a member selected from O and S. $X^c$ is a member selected from $OR^8$, $SR^8$ and $NR^8R^{8a}$, in which $R^8$ and $R^{8a}$ are members independently selected from H, and substituted or unsubstituted alkyl, or the compound is a salt and $OR^8$ and $SR^8$ are selected from $O^-M^+$ and $S^-M^+$. $M+$ is any cation capable of forming a salt with the negatively charged ion, including a metal ion or an ammonium ion. $R^9$ is a member selected from H, substituted or unsubstituted alkyl, substituted or unsubstituted heteroalkyl, substituted or unsubstituted aryl and substituted or unsubstituted heteroaryl and a nucleic acid optionally connected through a phosphorus-containing linker.

For $L^1$-$Y^a$-$L^3$,

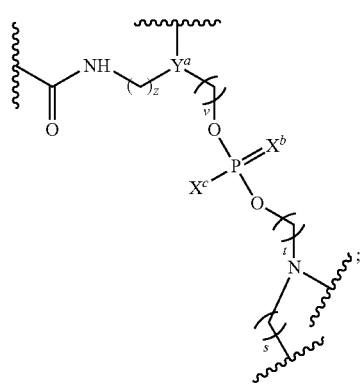

for example

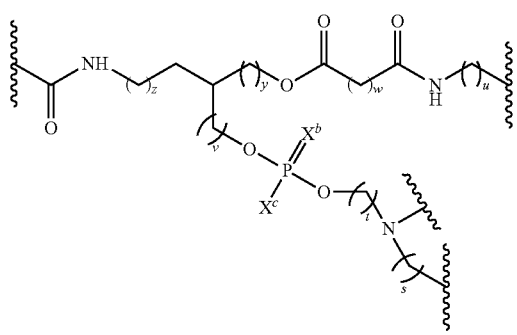

in which the indeces and variable radicals are as set forth above.

For $L^1$-$Y^a$-$L^2$,

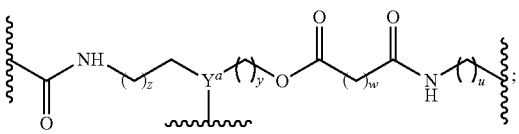

for example

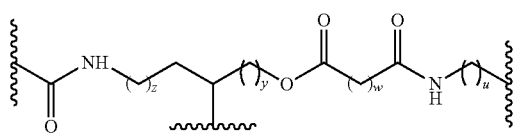

in which the indeces and variable radicals are as set forth above.

For $L^1$-$Y^a$-$L^3$,

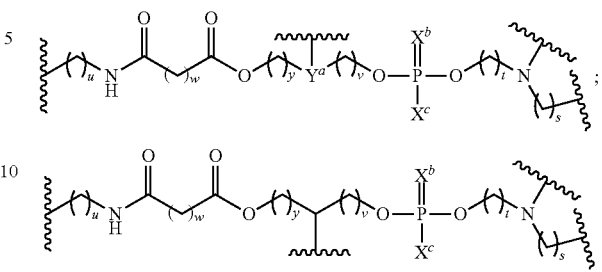

for example in which the indeces and variable radicals are as set forth above.

In exemplary embodiments, the invention provides a compound having a structure according to Formula VII:

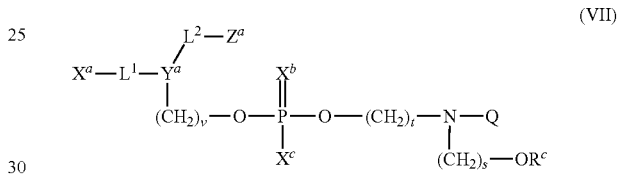

(VII)

in which the indices and variable radicals are as set forth above.

In selected embodiments, the invention includes a compound having a structure according to Formula VIII:

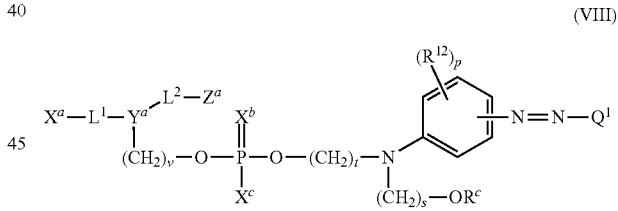

(VIII)

in which $Q^1$ is a fragment of the quencher. The fragment comprises a member selected from:

(a) two moieties selected from substituted or unsubstituted aryl and substituted or unsubstituted heteroaryl, said two moieties being linked through an exocyclic diazo bond; and (b) a moiety selected from substituted or unsubstituted polycyclic aryl and substituted or unsubstituted polycyclic heteroaryl groups.

Each $R^{12}$ is a member independently selected from the group of aryl substituents as defined herein: and the integer p is 0, 1, 2, 3, or 4. The remaining indeces and radicals are as set forth above.

With respect to linkers of use in the compounds of the present invention, an exemplary embodiment is provided in which $Z^a$ is a solid support and $L^2$-$Z^a$ comprises a structure according to Formula IX:

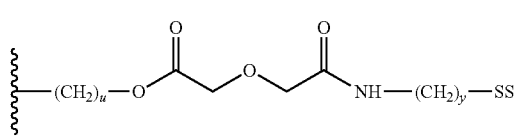

in which the indeces are as set forth above; and SS is the solid support.

In certain embodiments of the invention there is included on the solid support or a phosphoramidite or on an oligomer synthesized on the solid support a stabilizing moiety. An exemplary compound of the invention according to any of the above-described embodiments is one in which $X^a$ is selected from intercalating agents and minor groove binders.

In various embodiments, the solid support or phosphoramidite or oligomer of the invention includes a base having a formula selected from:

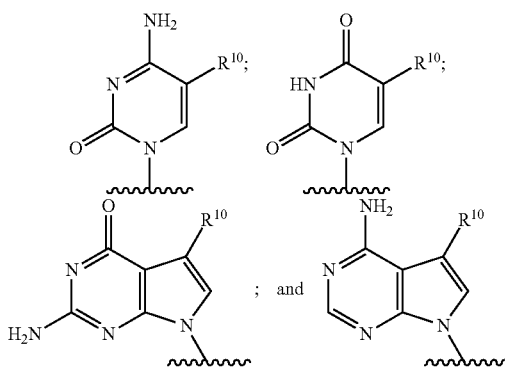

in which $R^{10}$ is a member selected from an alkynyl and a fluoroalkyl moiety.

By "alkynyl" is meant an acetylenically-unsaturated acylic group, such as ethynyl, 1-propynyl, 1-butynyl, 1-pentynyl, 1,3-pentadiynyl, phenylethynyl, phenylethynyl, pyridine-ethynyl, pyrimidine-ethynyl, triazine-ethynyl, thiophene-ethynyl, thiazole-ethynyl and imidazole-ethynyl. Exemplary substituted groups include substituted or unsubstituted $C_1$-$C_{10}$ alkynyl groups, e.g., $C_1$, $C_2$, $C_3$, $C_4$, $C_5$, $C_6$, $C_7$, $C_8$, $C_9$, or $C_{10}$ alkynyl, substituted with 2-, 3-, and 4-pyridinyl (e.g., 2-, 3- and 4-pyrimidine-ethynyl), triazine (e.g., triazinyl-ethynyl), 2-, 4- and 5-pyrimidinyl, 2-, 4- and 5-thiazolyl, 1-methyl-2-imidazolyl, 2- and 4-imidazolyl, 2-, 4- and 5-oxazolyl, 3-pyridinyl, 4-pyridinyl, 2-pyridinyl, 2- and 3-furanyl-ethynyl, 2- and 3-thienyl-ethynyl, 2- and 4-imidazolyl-ethynyl, 2-, 4- and 5-thiazoyl-ethynyl, 2-, 4- and 5-oxazolyl-ethynyl, 2- and 3-pyrrolyl-ethynyl, 2- and 3-thienyl, 2- and 3-furanyl, 2- and 3-pyrrolyl, propenyl (—CH═CH—CH$_3$), vinyl and —C≡C—Z' where Z' is hydrogen (H) or $C_1$-$C_{10}$ alkyl, haloalkyl ($C_1$-$C_{10}$ with 1 to 6 halogen atoms or heteroalkyl ($C_1$-$C_{10}$ with 1 to 3 heteroatoms selected from the group consisting of O, N and S). The alkynyl moiety can also be the component of a linker or a linkage fragment.

Exemplary fluoroalkyl groups include linear (e.g., $C_1$-$C_{20}$, $C_2$-$C_{16}$, $C_3$-$C_{10}$, $C_4$-$C_8$) and cycloalkyl (e.g., $C_3$-$C_8$) moieties substituted with one or more fluoro moiety. Exemplary fluoroalkyl groups include 1, 2, 3, 4, 5, 6, 7, 8, 9, 10, 11, 12, 13, 14, 15, 16, 17, 18, 19, or 20 carbon atoms. Perfluoro compounds are of use in the compounds of the invention.

Monomers

In various embodiments, the invention provides monomeric nucleic acids of use in synthesizing oligormers. In a representative embodiment, the monomeric nucleic acid is a phosphoramidite bearing a stabilizing moiety. An exemplary monomeric nucleic acid according to this embodiment has the formula:

In various embodiments, the stabilizing moiety is an alkyne residue, providing a monomeric nucleic acid having the formula:

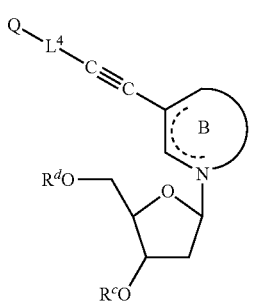

in which Q is a quencher, and $L^4$ is a linker. Exemplary linkers include zero-order and substituted or unsubstituted alkyl and substituted or unsubstituted heteroalkyl. $R^d$ is H, substituted or unsubstituted alkyl, or substituted or unsubstituted heteroalkyl. In an exemplary embodiment, $R^d$ is a nucleic acid protecting group, e.g., DMT. $R^c$ is H or is a component of a phosphoramidite, e.g., —OPN(i-Pr)$_2$(OCNE). The ring labeled B represents a base as defined herein. Exemplary bases include:

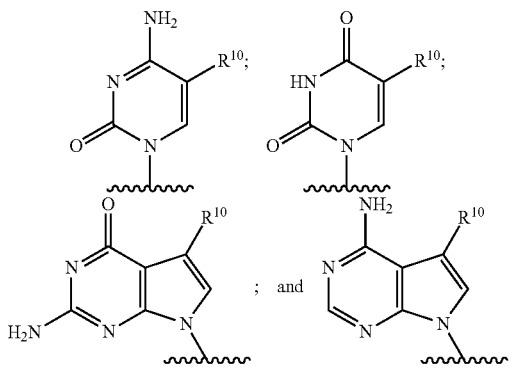

in which $R^{10}$ represents $L^4$-Q.

In various embodiments, Q-$L^4$ has the formula:

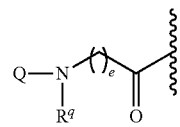

in which $R^q$ is H, substituted or unsubstituted alkyl or substituted or unsubstituted heteroalkyl and the index e represents an integer from 1 to 20, i.e., 1, 2, 3, 4, 5, 6, 7, 8, 9, 10, 11, 12, 13, 14, 15, 16, 17, 18, 19, 20.

Also provided is a nucleic acid oligomer, e.g., a probe, prepared using a monomer of the invention and including the components of the monomer from which it is synthesized.

Oligomers

Exemplary oligomers include oligonucleotides, oligonucleosides, oligodeoxyribonucleotides (containing 2'-deoxy-D-ribose or modified forms thereof), i.e., DNA, oligoribonucleotides (containing D-ribose or modified forms thereof), i.e., RNA, and any other type of polynucleotide which is an N-glycoside or C-glycoside of a purine or pyrimidine base, or modified purine or pyrimidine base. Oligomer as used herein also includes compounds where adjacent nucleomonomers are linked via amide linkages as previously described (Nielsen et al., *Science* (1991) 254:1497-1500). The enhanced competence of binding by oligomers containing the bases of the present invention is believed to be primarily a function of the base alone. Because of this, elements ordinarily found in oligomers, such as the furanose ring and/or the phosphodiester linkage can be replaced with any suitable functionally equivalent element. "Oligomer" is thus intended to include any structure that serves as a scaffold or support for the bases wherein the scaffold permits binding to target nucleic acids in a sequence-dependent manner.

Exemplary groups linking nucleomonomers in an oligomer of the invention include (i) phosphodiester and phosphodiester modifications (phosphorothioate, methylphosphonate, etc), (ii) substitute linkages that contain a non-phosphorous isostere (formacetal, riboacetal, carbamate, etc), (iii) morpholino residues, carbocyclic residues or other furanose sugars, such as arabinose, or a hexose in place of ribose or deoxyribose and (iv) nucleomonomers linked via amide bonds or acyclic nucleomonomers linked via any suitable substitute linkage.

The oligomers of the invention can be formed using modified and conventional nucleomonomers and synthesized using standard solid phase (or solution phase) oligomer synthesis techniques, which are now commercially available. In general, the oligomers can be synthesized by a method comprising the steps of: synthesizing a nucleomonomer or oligomer synthon having a protecting group and a base and a coupling group capable of coupling to a nucleomonomer or oligomer; coupling the nucleomonomer or oligomer synthon to an acceptor nucleomonomer or an acceptor oligomer; removing the protecting group; and repeating the cycle as needed until the desired oligomer is synthesized.

The oligomers of the present invention can be of any length including those of greater than 40, 50 or 100 nucleomonomers. In various embodiments, oligomers contain 2-30 nucleomonomers. Lengths of greater than or equal to about 8 to 20 nucleomonomers are useful for therapeutic or diagnostic applications. Short oligomers containing 2, 3, 4 or 5 nucleomonomers are specifically included in the present invention and are useful, e.g., as synthons.

Oligomers having a randomized sequence and containing fewer than 20, fewer than 15 or fewer than 10 nucleomonomers are useful for primers, e.g., in cloning or amplification protocols that use random sequence primers, provided that the oligomer contains residues that can serve as a primer for polymerases or reverse transcriptases.

Oligomers can contain conventional phosphodiester linkages or can contain phosphodiester modification such as phosphoramidate linkages. These substitute linkages include, but are not limited to, embodiments wherein a moiety of the formula —O—P(O)(S)—O— ("phosphorothioate"), —O—P(S)(S)—O— ("phosphorodithioate"), —O—P(O)(NR$^o$$_2$)—X—, —O—P(O)(R$^o$)—O—O—P(S)(R$^o$)—O— ("thionoalkylphosphonate"), —P(O)(OR$^p$)—X—, —O—C(O)—X—, or —O—C(O)(NR$^p$$_2$)—X—, wherein R$^o$ is H (or a salt) or alkyl (1-12C) and R$^p$ is alkyl (1-9C) and the linkage is joined to adjacent nucleomonomers through an —O— or —S— bonded to a carbon of the nucleomonomer. In various embodiments, the substitute linkages for use in the oligomers of the present invention include phosphodiester, phosphorothioate, methylphosphonate and thionomethylphosphonate linkages. Phosphorothioate and methylphosphonate linkages confer added stability to the oligomer in physiological environments. While not all such linkages in the same oligomer need be identical, particularly preferred oligomers of the invention contain uniformly phosphorothioate linkages or uniformly methylphosphonate linkages.

Oligomers or the segments thereof are conventionally synthesized, and can be prepared using a solid support and/or phosphoramidite of the invention. The synthetic methods known in the art and described herein can be used to synthesize oligomers containing bases of the invention, as well as other bases known in the art, using appropriately protected nucleomonomers. Methods for the synthesis of oligomers are found, for example, in Froehler, B., et al., *Nucleic Acids Res.* (1986) 14:5399-5467; *Nucleic Acids Res.* (1988) 16:4831-4839; *Nucleosides and Nucleotides* (1987) 6:287-291; Froehler, B., *Tetrahedron Lett.* (1986) 27:5575-5578; Caruthers, M. H. in Oligodeoxynucleotides-Antisense Inhibitions of Gene Expression (1989), J. S. Cohen, editor, CRC Press, Boca Raton, p 7-24; Reese, C. B. et al., *Tetrahedron Lett.* (1985) 26:2245-2248. Synthesis of the methylphosphonate linked oligomers via methyl phosphonamidite chemistry has also been described (Agrawal, S. et al., *Tetrahedron Lett.* (1987) 28:3539-3542; Klein, R. E., et al., International Publication Number WO 92/07864).

As disclosed herein, the invention provides "conjugates" of oligomers. For instance, the oligomers can be covalently linked to various functional components such as, stabilizing moieties ($X^a$), fluorophores, quenchers, intercalators, and substances which interact specifically with the minor groove of the DNA double helix (minor groove binders, "MGB"). Other chosen conjugate moieties, can be labels such as radioactive, fluorescent, enzyme, or moieties which facilitate cell association using cleavage linkers and the like. Suitable radiolabels include $^{32}$P, $^{35}$S, $^3$H and $^{14}$C; and suitable fluorescent labels include fluorescein, resorufin, rhodamine, BODIPY (Molecular Probes) and texas red; suitable enzymes include alkaline phosphatase and horseradish peroxidase. Additional fluorophores are set forth herein and are generally recognized in the art. Other covalently linked moieties include biotin, antibodies or antibody fragments, and proteins, e.g., transferrin and the HIV Tat protein.

As discussed herein and recognized in the art, the oligomers can be derivatized through any convenient linkage. For example, minor groove binders, fluorophores, quenchers and intercalators, such as acridine or psoralen can be linked to the oligomers of the invention through any available —OH or —SH, e.g., at the terminal 5'-position of the oligomer, the 2'-positions of RNA, or an OH, NH$_2$, COOH or SH incorporated into the 5-position of pyrimidines. A derivatized form which contains, for example, —CH$_2$CH$_2$NH$_2$, —CH$_2$CH$_2$CH$_2$OH or —CH$_2$CH$_2$CH$_2$SH in the 5-position is of use in the present invention. Conjugates including polylysine or lysine can be synthesized as described and can further enhance the binding affinity of an oligomer to its target nucleic acid sequence (Lemaitre, M. et al., Proc Natl Acad Sci (1987) 84:648-652; Lemaitre, M. et al., *Nucleosides and Nucleotides* (1987) 6:311-315).

A wide variety of substituents can be attached, including those bound through linkages or substitute linkages. The —OH moieties in the phosphodiester linkages of the oligomers can be replaced by phosphate groups, protected by standard protecting groups, or coupling groups to prepare additional linkages to other nucleomonomers, or can be bound to the conjugated substituent. The 5'-terminal OH can be phosphorylated; the 2'-OH or OH substituents at the 3'-terminus can also be phosphorylated. The hydroxyls can also be derivatized to standard protecting groups.

Oligomers of the invention can be covalently derivatized to moieties that facilitate cell association using cleavable linkers. Linkers used for such conjugates can include disulfide linkages that are reduced after the oligomer-transport agent conjugate has entered a cell. Disulfide-containing linkers of this type have a controllable half life. Such linkers are stable under extracellular conditions relative to intracellular conditions due to the redox potential of the disulfide linkage.

Donor and Acceptor Moieties

Quenchers

Exemplary solid supports and oligomers of the invention include a quencher covalently attached thereto, optionally through a linker. In various embodiments, the quencher is a moiety having a structure according to Formula (II)

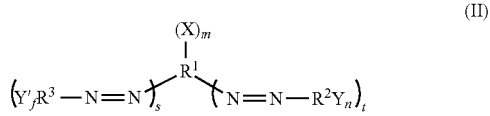

(II)

in which $R^1$, $R^2$ and $R^3$ are members independently selected from substituted or unsubstituted aryl, and substituted or unsubstituted heteroaryl. The symbols X, Y and Y' are members independently selected from reactive functional groups and linkage fragments covalently binding said quencher to $L^3$. The index f is a number selected from 0 to 4 (i.e., 0, 1, 2, 3, or 4), inclusive, such that when (f×s) is greater than 1, the Y' groups are the same or different. The index m is a number selected from 0 to 5 (i.e., 0, 1, 2, 3, 4, or 5), inclusive, such that when m is greater than 1, the X groups are the same or different. The index n is a number from 0 to 6 (i.e., 0, 1, 2, 3, 4, 5 or 6), inclusive, such that when (n×t) is greater than 1, the Y groups are the same or different. The index s is a number from 0 to 6 (i.e., 0, 1, 2, 3, 4, 5 or 6), inclusive, such that when s is greater than 1 the $R^3$ groups are the same or different the index t is a number from 1 to 6 (i.e., 1, 2, 3, 4, 5 or 6), inclusive, such that when t is greater than 1 the $R^2$ groups are the same or different, and when t is 1 and s is 0, a member selected from $R^1$, $R^2$ and combinations thereof is a member selected from substituted or unsubstituted polycyclic aryl and substituted or unsubstituted polycyclic heteroaryl groups.

In various embodiments, the quencher has a structure according to Formula (III):

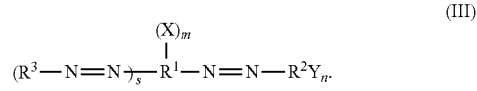

(III)

The solid support and oligomers of the invention also can include quencher according to Formula III in which a member selected from $R^1$, $R^2$ and $R^3$ includes a structure according to Formula IV:

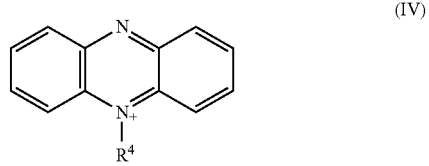

(IV)

in which $R^4$ is a member selected from alkyl, substituted alkyl, aryl, substituted aryl, heteroaryl and substituted heteroaryl.

Quenchers of use in various embodiments have a structure according to Formula V:

(V)

in which v is an integer from 1 to 10 (i.e., 1, 2, 3, 4, 5, 6, 7, 8, 9, 10).

In exemplary embodiments, the quencher has a structure according to Formula VI:

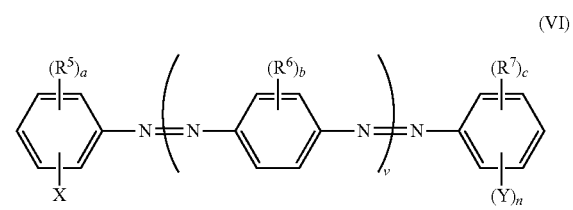

(VI)

in which the symbols $R^5$, $R^6$ and $R^7$ are members independently selected from —NR'R", substituted or unsubstituted aryl, nitro, substituted or unsubstituted $C_1$-$C_6$ alkyl, and substituted or unsubstituted $C_1$-$C_6$ alkoxy. R' and R" are independently selected from H and substituted or unsubstituted $C_1$-$C_6$ alkyl. The index n is an integer from 0 to 1. The index a is an integer from 0 to 4 (i.e., 0, 1, 2, 3, or 4), such that when a is greater than 1, the $R^5$ groups are the same or different. The index b is an integer from 0 to 4 (i.e., 0, 1, 2, 3, or 4), such that when (v×b) is greater than 1, the $R^6$ groups are the same or different. The index c is an integer from 0 to 5 (i.e., 0, 1, 2, 3, 4, or 5), such that when c is greater than 1, the $R^7$ groups are the same or different; and v is an integer from 1 to 10 (i.e., 1, 2, 3, 3, 4, 5, 6, 7, 8, 9, 10), such that when v is greater than 1, the value of b on each of the b phenyl rings is the same or different.

Various embodiments utilize a quencher having a structure according to Formula VII:

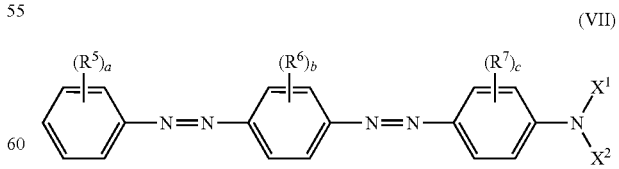

(VII)

in which $R^5$, $R^6$ and $R^7$ are members independently selected from amine, alkyl amine, substituted or unsubstituted aryl, nitro, substituted or unsubstituted $C_1$-$C_6$ alkyl, substituted or unsubstituted $C_1$-$C_6$ alkoxy. The symbols $X^1$ and $X^2$ represent members independently selected from $C_1$-$C_6$ alkyl or $C_1$-$C_6$ substituted alkyl, —OH, —COOH, —NR'R", —SH, —OP(OX³)(NR'R") and a linkage fragment covalently binding said quencher to $L^3$. R' and R" are members independently selected from the group consisting of H, and substituted or unsubstituted alkyl and substituted or unsubstituted heteroalkyl.

In certain embodiments, the compounds of the invention utilize a quencher having a structure which is a member selected from:

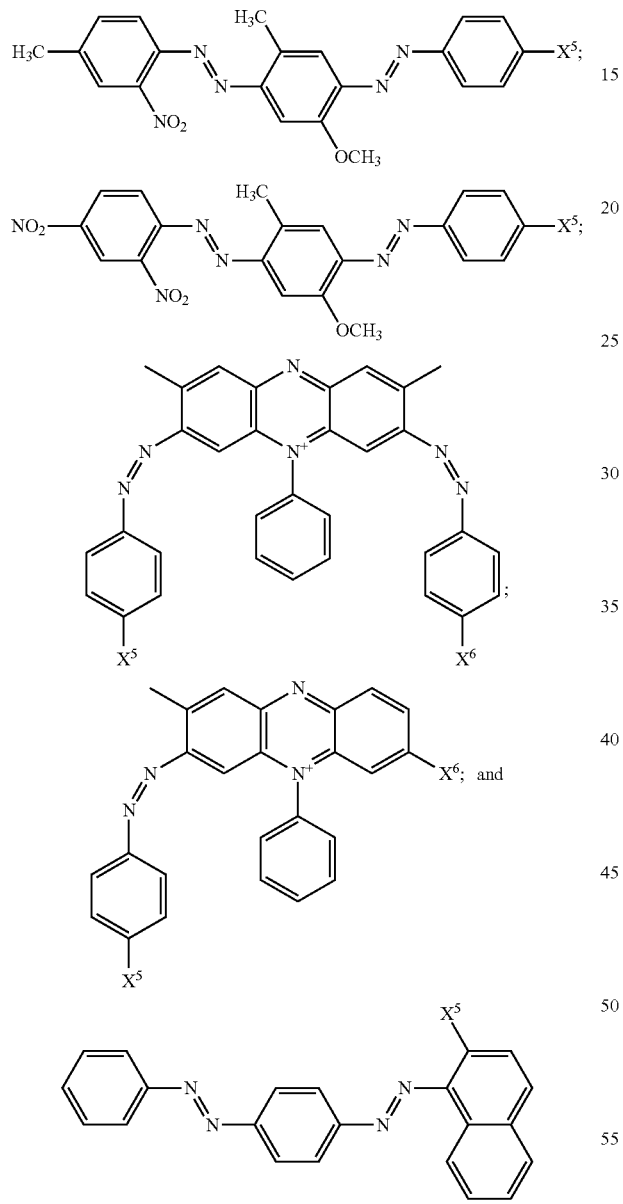

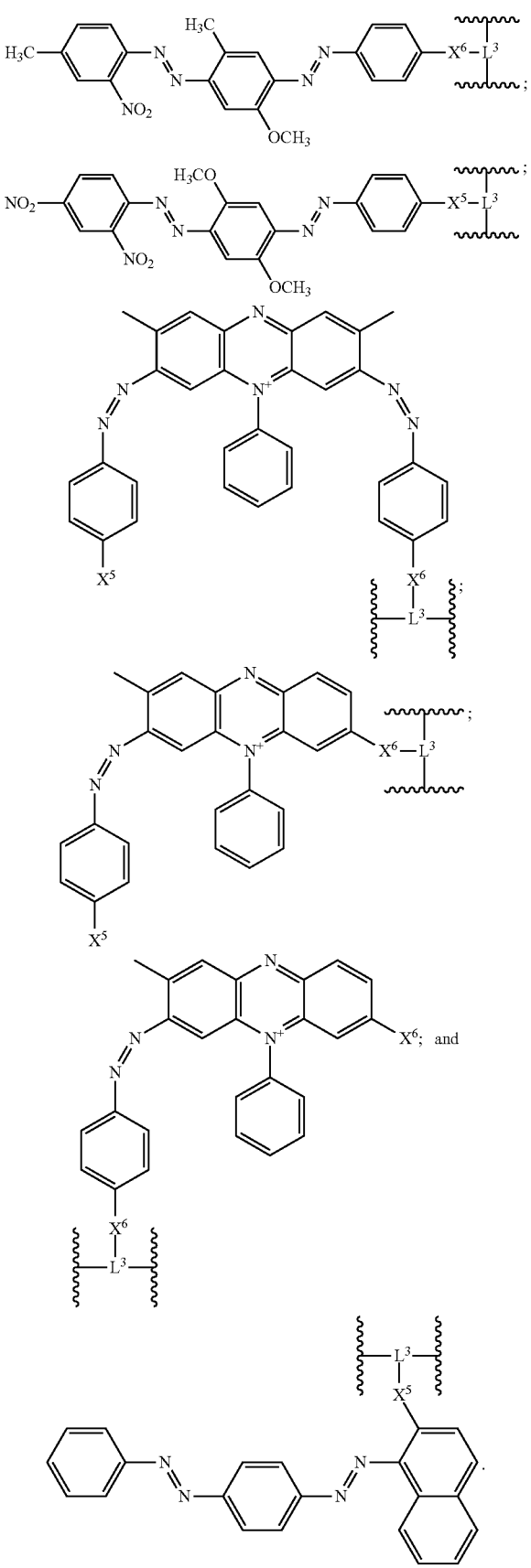

in which $X^5$ and $X^6$ are members independently selected from H, a reactive functional group and a linkage fragment covalently binding said quencher (Q) to $L^3$, with the proviso that at least one of $X^5$ and $X^6$ is such a linkage fragment.

Thus, the invention provides compounds according to Formula I, including the component a component selected from:

As one of skill will appreciate, $L^3$ in the above structures can be replaced with $L^4$ and its attachment to a propyne-modified base.

One of the advantages of the compounds of the invention is that a wide range of energy donor molecules can be used in conjunction with the quencher-functionalized solid supports and oligomers. A vast array of fluorophores is known to those of skill in the art. See, for example, Cardullo et al., *Proc. Natl. Acad. Sci. USA* 85: 8790-8794 (1988); Dexter, D. L., *J. of Chemical Physics* 21: 836-850 (1953); Hochstrasser et al., *Biophysical Chemistry* 45: 133-141 (1992); Selvin, P., *Methods in Enzymology* 246: 300-334 (1995); Steinberg, I. *Ann. Rev. Biochem.*, 40: 83-114 (1971); Stryer, L. *Ann. Rev. Biochem.*, 47: 819-846 (1978); Wang et al., *Tetrahedron Letters* 31: 6493-6496 (1990); Wang et al., *Anal. Chem.* 67: 1197-1203 (1995).

A non-limiting list of exemplary donors that can be used in conjunction with the quenchers of the invention is provided in Table 1.

TABLE 1

Suitable moieties that can be selected as donors or acceptors in donor-acceptor energy transfer pairs 4-acetamido-4'-isothiocyanatostilbene-2,2'disulfonic acid
acridine and derivatives:
    acridine
    acridine isothiocyanate
5-(2'-aminoethyl)aminonaphthalene-1-sulfonic acid (EDANS)
4-amino-N-[3-vinylsulfonyl)phenyl]naphthalimide-3,5 disulfonate
N-(4-anilino-1-naphthyl)maleimide
anthranilamide
BODIPY
Brilliant Yellow
coumarin and derivatives:
coumarin
    7-amino-4-methylcoumarin (AMC, Coumarin 120)
    7-amino-4-trifluoromethylcouluarin (Coumaran 151)
cyanine dyes
cyanosine
4',6-diaminidino-2-phenylindole (DAPI)
5', 5''-dibromopyrogallol-sulfonaphthalein (Bromopyrogallol Red)
7-diethylamino-3-(4'-isothiocyanatophenyl)-4-methylcoumarin
diethylenetriamine pentaacetate
4,4'-diisothiocyanatodihydro-stilbene-2,2'-disulfonic acid
4,4'-diisothiocyanatostilbene-2,2'-disulfonic acid
5-[dimethylamino]naphthalene-1-sulfonyl chloride (DNS, dansylchloride)
4-(4'-dimethylaminophenylazo)benzoic acid (DABCYL)
4-dimethylaminophenylazophenyl-4'-isothiocyanate (DABITC)
eosin and derivatives:
    eosin
    eosin isothiocyanate
erythrosin and derivatives:
    erythrosin B
    erythrosin isothiocyanate
ethidium
fluorescein and derivatives:
    5-carboxyfluorescein (FAM)
    5-(4,6-dichlorotriazin-2-yl)aminofluorescein (DTAF)
    2',7'-dimethoxy-4'5'-dichloro-6-carboxyfluoresccin (JOE)
    fluorescein
    fluorescein isothiocyanate
    QFITC (XRITC)
fluorescamine
IR144
IR1446
Malachite Green isothiocyanate
4-methylumbelliferone
ortho cresolphthalein
nitrotyrosine
pararosaniline
Phenol Red
B-phycoerythrin
o-phthaldialdehyde TABLE 1-continued Suitable moieties that can be selected as donors or acceptors in donor-acceptor energy transfer pairs pyrene and derivatives:
    pyrene
    pyrene butyrate
    succinimidyl 1-pyrene butyrate
quantum dots
Reactive Red 4 (Cibacron ™ Brilliant Red 3B-A)
rhodamine and derivatives:
    6-carboxy-X-rhodamine (ROX)
    6-carboxyrhodamine (R6G)
    lissamine rhodamine B sulfonyl chloride rhodamine (Rhod)
    rhodamine B
    rhodamine 123
    rhodamine X isothiocyanate
    sulforhodamine B
    sulforhodamine 101
sulfonyl chloride derivative of sulforhodamine 101 (Texas Red)
N,N,N',N'-tetramethyl-6-carboxyrhodamine (TAMRA)
tetramethyl rhodamine
    tetramethyl rhodamine isothiocyanate (TRITC)
riboflavin
rosolic acid
metal chelates, e.g., lanthanide chelates (e.g., europium terbium chelates), ruthenium chelates There is a great deal of practical guidance available in the literature for selecting appropriate donor-acceptor pairs for particular probes, as exemplified by the following references: Pesce et al., Eds., FLUORESCENCE SPECTROSCOPY (Marcel Dekker, New York, 1971); White et al., FLUORESCENCE ANALYSIS: A PRACTICAL APPROACH (Marcel Dekker, New York, 1970); and the like. The literature also includes references providing exhaustive lists of fluorescent and chromogenic molecules and their relevant optical properties for choosing reporter-quencher pairs (see, for example, Berlman, HANDBOOK OF FLUORESCENCE SPECTRA OF AROMATIC MOLECULES, 2nd Edition (Academic Press, New York, 1971); Griffiths, COLOUR AND CONSTITUTION OF ORGANIC MOLECULES (Academic Press, New York, 1976); Bishop, Ed., INDICATORS (Pergamon Press, Oxford, 1972); Haugland, HANDBOOK OF FLUORESCENT PROBES AND RESEARCH CHEMICALS (Molecular Probes, Eugene, 1992) Pringsheim, FLUORESCENCE AND PHOSPHORESCENCE (Interscience Publishers, New York, 1949); and the like. Further, there is extensive guidance in the literature for derivatizing reporter and quencher molecules for covalent attachment via common reactive groups that can be added to a nucleic acid, as exemplified by the following references: Haugland (supra); Ullman et al., U.S. Pat. No. 3,996,345; Khanna et al., U.S. Pat. No. 4,351,760. Thus, it is well within the abilities of those of skill in the art to choose an energy exchange pair for a particular application and to conjugate the members of this pair to a probe molecule, such as, for example, a nucleic acid, peptide or other polymer.

Generally, it is preferred that an absorbance band of the BHQ substantially overlap the fluorescence emission band of the donor. When the donor (fluorophore) is a component of a probe that utilizes donor-acceptor energy transfer, the donor fluorescent moiety and the quencher (acceptor) of the invention are preferably selected so that the donor and acceptor moieties exhibit donor-acceptor energy transfer when the donor moiety is excited. One factor to be considered in choosing the fluorophore-quencher pair is the efficiency of donor-acceptor energy transfer between them. Preferably, the efficiency of FRET between the donor and acceptor moieties is at least 10%, more preferably at least 50% and even more preferably at least 80%. The efficiency of FRET can easily be empirically tested using the methods both described herein and known in the art.

The efficiency of energy transfer between the donor-acceptor pair can also be adjusted by changing the ability of the donor and acceptor groups to dimerize or closely associate. If the donor and acceptor moieties are known or determined to closely associate, an increase or decrease in association can be promoted by adjusting the length of a linker moiety, or of the probe itself, between the donor and acceptor. The ability of donor-acceptor pair to associate can be increased or decreased by tuning the hydrophobic or ionic interactions, or the steric repulsions in the probe construct. Thus, intramolecular interactions responsible for the association of the donor-acceptor pair can be enhanced or attenuated. Thus, for example, the association between the donor-acceptor pair can be increased by, for example, utilizing a donor bearing an overall negative charge and an acceptor with an overall positive charge.

In addition to fluorophores that are attached directly to a probe, the fluorophores can also be attached by indirect means. In this embodiment, a ligand molecule (e.g., biotin) is generally covalently bound to the probe species. The ligand then binds to another molecules (e.g., streptavidin) molecule, which is either inherently detectable or covalently bound to a signal system, such as a fluorescent compound, or an enzyme that produces a fluorescent compound by conversion of a non-fluorescent compound. Useful enzymes of interest as labels include, for example, hydrolases, particularly phosphatases, esterases and glycosidases, hydrolases, peptidases or oxidases, particularly peroxidases, and. Fluorescent compounds include fluorescein and its derivatives, rhodamine and its derivatives, dansyl, umbelliferone, etc., as discussed above. For a review of various labeling or signal producing systems that can be used, see, U.S. Pat. No. 4,391,904.

Presently preferred donors of use in conjunction with BHQ, include, for example, xanthene dyes, including fluoresceins, cyanine dyes and rhodamine dyes. Many suitable forms of these compounds are widely available commercially with substituents on their phenyl moieties, which can be used as the site for bonding or as the bonding functionality for attachment to an nucleic acid. Another group of preferred fluorescent compounds are the naphthylamines, having an amino group in the alpha or beta position. Included among such naphthylamino compounds are 1-dimethylaminonaphthyl-5-sulfonate, 1-anilino-8-naphthalene sulfonate and 2-p-touidinyl-6-naphthalene sulfonate. Other donors include 3-phenyl-7-isocyanatocoumarin, acridines, such as 9-isothiocyanatoacridine and acridine orange; N-(p-(2-benzoxazolyl)phenyl)maleimide; benzoxadiazoles, stilbenes, pyrenes, and the like.

For clarity of illustration, the discussion below focuses on attaching BHQs and fluorophores to nucleic acids. The focus on nucleic acid probes is not intended to limit the scope of probe molecules to which BHQs can be attached. Those of skill in the art will appreciate that BHQs can also be attached to small molecules, proteins, peptides, synthetic polymers, solid supports and the like using standard synthetic chemistry.

In a presently preferred embodiment, in which the probe is a nucleic acid probe, the reporter molecule is a fluorescein dye (FAM). The fluorescein moiety is preferably attached to either the 3'- or the 5'-terminus of the nucleic acid, although internal sites are also accessible and have utility for selected purposes. Whichever terminus the FAM derivative is attached to, the BHQ will generally be attached to its antipode, or at a position internal to the nucleic acid chain. The FAM donor is preferably introduced using a 6-FAM amidite. Different donor groups are also preferably introduced using an amidite derivative of the donor. Alternatively, donor groups comprising reactive functional groups (e.g., isothiocyanates, active esters, etc.) can be introduced via reaction with a reactive functional group on a tether or linker arm attached to the nucleic acid (e.g., hexyl amine).

In yet another preferred embodiment, the donor moiety can be attached at the 3'-terminus of a nucleic acid by the use of a derivatized synthesis support. For example, TAMRA (tetramethylrhodamine carboxylic acid) is attached to a nucleic acid 3'-terminus using a solid support that is derivatized with an analogue of this fluorophore (Biosearch Technologies, Inc.)

In view of the well-developed body of literature concerning the conjugation of small molecules to nucleic acids, many other methods of attaching donor/acceptor pairs to nucleic acids will be apparent to those of skill in the art. For example, rhodamine and fluorescein dyes are conveniently attached to the 5'-hydroxyl of an nucleic acid at the conclusion of solid phase synthesis by way of dyes derivatized with a phosphoramidite moiety (see, for example, Woo et al., U.S. Pat. No. 5,231,191; and Hobbs, Jr., U.S. Pat. No. 4,997,928).

More specifically, there are many linker moieties and methodologies for attaching groups to the 5'- or 3'-termini of nucleic acids, as exemplified by the following references: Eckstein, editor, Nucleic acids and Analogues: A Practical Approach (IRL Press, Oxford, 1991); Zuckerman et al., *Nucleic Acids Research,* 15: 5305-5321 (1987) (3'-thiol group on nucleic acid); Sharma et al., *Nucleic Acids Research,* 19: 3019 (1991) (3'-sulfhydryl); Giusti et al., *PCR Methods and Applications,* 2: 223-227 (1993) and Fung et al., U.S. Pat. No. 4,757,141 (5'-phosphoamino group via Aminolink TM II available from P.E. Biosystems, CA.) Stabinsky, U.S. Pat. No. 4,739,044 (3-aminoalkylphosphoryl group); Agrawal et al., *Tetrahedron Letters,* 31: 1543-1546 (1990) (attachment via phosphoramidate linkages); Sproat et al. *Nucleic Acids Research,* 15: 4837 (1987) (5-mercapto group); Nelson et al., *Nucleic Acids Research,* 17: 7187-7194 (1989) (3'-amino group), and the like.

Means of detecting fluorescent labels are well known to those of skill in the art. Thus, for example, fluorescent labels can be detected by exciting the fluorophore with the appropriate wavelength of light and detecting the resulting fluorescence. The fluorescence can be detected visually, by means of photographic film, by the use of electronic detectors such as charge coupled devices (CCDs) or photomultipliers and the like. Similarly, enzymatic labels may be detected by providing the appropriate substrates for the enzyme and detecting the resulting reaction product.

Reactive Functional Groups

The components of the solid supports and oligomers of the invention (e.g., linkers, fluorophore, quenchers, stabilizing moiety are linked through linkage fragments formed by reaction of a first and a second reactive functional group. The reactive functional groups are of complementary reactivity, and they react to form a covalent link between two components of the oligomers referred to herein as a linkage fragment. With reference to the solid support of Formula I, the reactive functional group is found on precursors of $L^1$, $L^2$ and $L^3$, as well as on precursors of Q, $Z^a$ and $X^a$. In various examples, $X^a$ and $L^1$ are covalently joined through a linkage fragment; $L^2$ and $Z^a$ are joined by a linkage fragment; $L^3$ and Q are joined by a linkage fragment, each linkage fragment formed by reaction of reactive functional groups on the precursors of the named components of the oligomers of the invention. Linkage fragments are present in similar groups of the oligomers of Formulae VII and VIII.

With respect to the precursors of the components of solid supports, phosphoramidites and oligomers of the invention, reactive functional groups can be located at any position on these precursors, e.g., an alkyl or heteroalkyl an aryl or heteroaryl nucleus or a substituent on an aryl or heteroaryl nucleus. Similarly, a reactive functional group is located at any position of an alkyl or heteroalkyl chain. In various embodiments, when the reactive group is attached to an alkyl (or heteroalkyl), or substituted alkyl (or heteroalkyl) chain, the reactive group is preferably located at a terminal position of the chain.

Reactive groups and classes of reactions useful in practicing the present invention are generally those that are well known in the art of bioconjugate chemistry. Currently favored classes of reactions available with reactive precursors of the oligomers of the invention are those which proceed under relatively mild conditions. These include, but are not limited to nucleophilic substitutions (e.g., reactions of amines and alcohols with acyl halides, active esters), electrophilic substitutions (e.g., enamine reactions) and additions to carbon-carbon and carbon-heteroatom multiple bonds (e.g., Michael reaction, Diels-Alder addition). These and other useful reactions are discussed in, for example, March, ADVANCED ORGANIC CHEMISTRY, 3rd Ed., John Wiley & Sons, New York, 1985; Hermanson, BIOCONJUGATE TECHNIQUES, Academic Press, San Diego, 1996; and Feeney et al., MODIFICATION OF PROEINS; Advances in Chemistry Series, Vol. 198, American Chemical Society, Washington, D.C., 1982.

By way of example, reactive functional groups of use in the present invention include, but are not limited to olefins, acetylenes, alcohols, phenols, ethers, oxides, halides, aldehydes, ketones, carboxylic acids, esters, amides, cyanates, isocyanates, thiocyanates, isothiocyanates, amines, hydrazines, hydrazones, hydrazides, diazo, diazonium, nitro, nitriles, mercaptans, sulfides, disulfides, sulfoxides, sulfones, sulfonic acids, sulfinic acids, acetals, ketals, anhydrides, sulfates, sulfenic acids isonitriles, amidines, imides, imidates, nitrones, hydroxylamines, oximes, hydroxamic acids thiohydroxamic acids, allenes, ortho esters, sulfites, enamines, ynamines, ureas, pseudoureas, semicarbazides, carbodiimides, carbamates, imines, azides, azo compounds, azoxy compounds, and nitroso compounds. Reactive functional groups also include those used to prepare bioconjugates, e.g., N-hydroxysuccinimide esters, maleimides and the like. Methods to prepare each of these functional groups are well known in the art and their application to or modification for a particular purpose is within the ability of one of skill in the art (see, for example, Sandler and Karo, eds. ORGANIC FUNCTIONAL GROUP PREPARATIONS, Academic Press, San Diego, 1989).

Useful reactive functional group conversions include, for example:

(a) carboxyl groups which are readily converted to various derivatives including, but not limited to, active esters (e.g., N-hydroxysuccinimide esters. N-hydroxybenztriazole esters, thioesters, p-nitrophenyl esters), acid halides, acyl imidazoles, alkyl, alkenyl, alkynyl and aromatic esters;

(b) hydroxyl groups, which can be converted to esters, ethers, halides, aldehydes, etc.

(c) haloalkyl groups, wherein the halide can be later displaced with a nucleophilic group such as, for example, an amine, a carboxylate anion, thiol anion, carbanion, or an alkoxide ion, thereby resulting in the covalent attachment of a new group at the site of the halogen atom;

(d) dienophile groups, which are capable of participating in Diels-Alder reactions such as, for example, maleimido groups;

(e) aldehyde or ketone groups, such that subsequent derivatization is possible via formation of carbonyl derivatives such as, for example, imines, hydrazones, semicarbazones or oximes, or via such mechanisms as Grignard addition or alkyllithium addition;

(f) sulfonyl halide groups for subsequent reaction with amines, for example, to form sulfonamides;

(g) thiol groups, which can be, for example, converted to disulfides or reacted with acyl halides;

(h) amine or sulfhydryl groups, which can be, for example, acylated, alkylated or oxidized;

(i) alkenes, which can undergo, for example, cycloadditions, acylation, Michael addition, etc;

(j) epoxides, which can react with, for example, amines and hydroxyl compounds; and (k) phosphoramidites and other standard functional groups useful in nucleic acid synthesis.

The reactive functional groups can be chosen such that they do not participate in, or interfere with, the reactions necessary to assemble the oligomer of the invention. Alternatively, a reactive functional group can be protected from participating in the reaction by the presence of a protecting group. Those of skill in the art understand how to protect a particular functional group such that it does not interfere with a chosen set of reaction conditions. For examples of useful protecting groups, see, for example, Greene et al., PROTECTIVE GROUPS IN ORGANIC SYNTHESIS, John Wiley & Sons, New York, 1991.

Covalent Bonding Moiety

Included in some of the oligomers of the invention is a reactive functional group moiety which is capable of effecting at least one covalent bond between the oligomer and a target sequence. Multiple covalent bonds can also be formed by providing a multiplicity of such moieties. The covalent bond is preferably to a base residue in the target strand, but can also be made with other portions of the target, including the sugar or phosphodiester. The reaction nature of the moiety which effects crosslinker determines the nature of the target in the duplex. Preferred crosslinker moieties include acylating and alkylating agents, and, in particular, those positioned relative to the sequence specificity-conferring portion so as to permit reaction with the target location in the strand.

The crosslinker moiety can conveniently be placed as an analogous pyrimidine or purine residue in the sequence of the oligomer. The placement can be at the 5'- and/or 3'-ends, the internal portions of the sequence, or combinations of the above. Placement at the termini to permit enhanced flexibility is preferred. Analogous moieties can also be attached to peptide backbones.

Exemplary of alkylating moieties that are useful in the invention include $N^4,N^4$-ethanocytosine and $N^6,N^6$-ethanoadenine.

It is clear that the base need not be a purine or pyrimidine: indeed the moiety to which the reactive function is attached need not be a base at all and may be a sugar, a linker, a quencher, a stabilizing moiety a fluorophore or some combination of these components of the oligomers of the invention. Any means of attaching the reactive group is satisfactory so long as the positioning is correct.

Synthesis

Solid supports, monomers (e.g., phosphoramidites) and oligomers of the invention or the segments thereof are generally conventionally synthesized. The synthetic methods known in the art and described herein can be used to synthesize oligomers containing bases of the invention, as well as other bases known in the art, using appropriately protected nucleomonomers. Methods for the synthesis of oligomers are found, for example, in Froehler, B., et al., *Nucleic Acids Res.* (1986) 14:5399-5467; *Nucleic Acids Res.* (1988) 16:4831-4839; *Nucleosides and Nucleotides* (1987) 6:287-291; Froehler, B., Tetrahedron Letters (1986) 27:5575-5578; Caruthers, M. H. in Oligodeoxynucleotides-Antisense Inhibitions of Gene Expression (1989), J. S. Cohen, editor, CRC Press, Boca Raton, p 7-24; Reese, C. B. et al., Tetrahedron Letters (1985) 28:2245-2248. Synthesis of the methylphosphonate linked oligomers via methyl phosphonamidite chemistry has also been described (Agrawal, S. et al., *Tetrahedron Letters* (1987) 28:3539-3542; Klem, R. E., et al., International Publication Number WO 92/07864).

Figure 2:
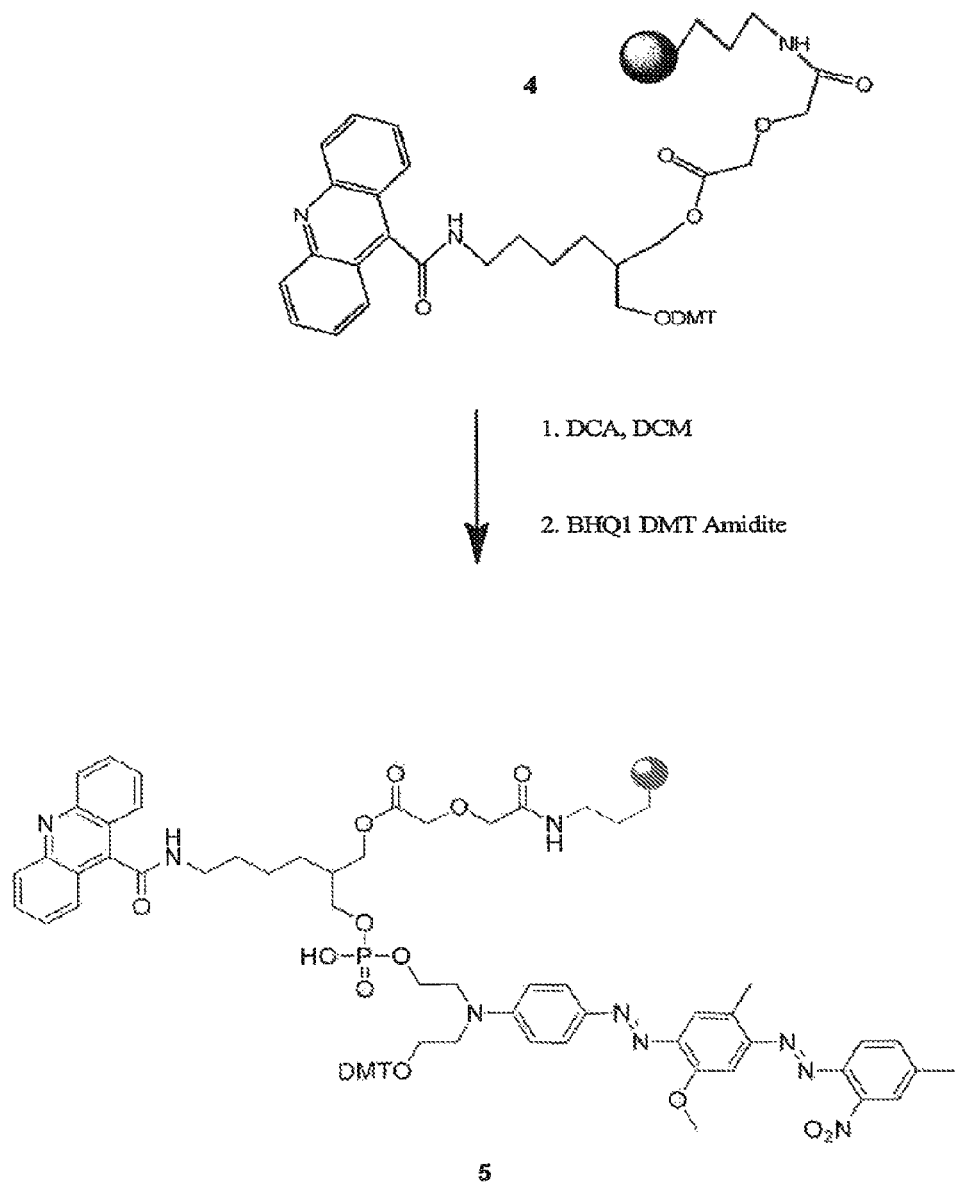
FIG. 2 is a scheme showing an exemplary preparation of a solid support of the invention derivatized with functional moieties.

An exemplary synthesis of a solid support of the invention is set forth in FIG. 1, FIG. 2 and the examples appended hereto.

In an exemplary embodiment, nucleomonomers are directly incorporated into oligomers or a convenient fragment thereof using standard synthesis conditions and reagents. Exemplary linkages made by this method include phosphodiester, phosphorothioate, phosphoroamidate, methylphosphonate, phosphorodithioate, carbonate, morpholino carbamate and sulfonate.

In various embodiments, synthesis involves synthesis of short synthons (dimers, trimers, etc.) starting with an appropriate precursor. This approach is suitable for synthesis of linkages including N-methylhydroxylamine, dimethylhydrazo, sulfamate, carbamate, sulfonate, sulfonamide, formacetal thioformacetal and carbonate.

Oligomers of the invention can be synthesized by any suitable chemistry including amidite, triester or hydrogen phosphonate coupling methods and conditions. The oligomers are preferably synthesized from appropriate starting synthons which are preferably protected at the 5'-position with DMT, MMT, FMOC (9-fluorenylmethoxycarbonyl), PACO (phenoxyacetyl), a silyl ether such as TBDMS (t-butyldiphenylsilyl) or TMS (trimethylsilyl) and activated at the 3'-position is an ester, H-phosphonate, an amidite such as β-cyanoethylphosphoramidite, a silyl ether such as TBDMS or TMS or t-butyldiphenyl. Alternatively, appropriate uridine or cytidine precursors such as blocked 5-iodo-2'-deoxyuridine, 5-iodo-2'-O-alkyluridine, 5-bromo-2'-deoxyuridine, 5-trifluoromethanesulfonate-2'-deoxyuridine, 5-bromo-2'-O-alkyluridine or blocked and protected 5-iodo-2'-deoxycytidine, 5-bromo-2'-deoxycytidine, 5-trifluoromethanesulfonate-2'-deoxycytidine, 5-iodo-2'-O-alkylcytidine, 5-bromo-2-alkylcytidine can be conveniently incorporated into short oligomers such as dimer, trimer, tetramer, pentamer or longer synthons that are subsequently derivatized to yield suitable synthons and longer oligomers.

Exemplary synthesis of oligomers containing about 4 or more nucleomonomer residues are accomplished using synthons such as monomers, dimers or trimers that carry a coupling group suitable for use with amidite, H-phosphonate or triester chemistries. The synthon can be used to link the components of the oligomer via a phosphodiester or phosphorous-containing linkage other than phosphodiester (e.g., phosphorothioate, methylphosphonate, thionomethylphosphonate, phosphoramidate and the like).

Synthesis of other nonphosphorous-containing substituted linkages can be accomplished using appropriate precursors as known in the art.

Once the desired nucleic acid is synthesized, it is preferably cleaved from the solid support on which it was synthesized and treated, by methods known in the art, to remove any protecting groups present (e.g., 60° C., 5 h, concentrated ammonia). In those embodiments in which a base-sensitive group is attached to the nucleic acids (e.g., TAMRA), the deprotection will preferably use milder conditions (e.g., butylamine:water 1:3, 8 hours, 70° C.). Deprotection under these conditions is facilitated by the use of quick deprotect amidites (e.g., dC-acetyl, dG-dmf).

Following cleavage from the support and deprotection, the nucleic acid is purified by any method known in the art, including chromatography, extraction and gel purification. In a preferred embodiment, the nucleic acid is purified using HPLC. The concentration and purity of the isolated nucleic acid is preferably determined by measuring the optical density at 260 nm in a spectrophotometer.

Assays and Oligomeric Probes of the Invention

In various embodiments, the present invention provides an oligomer of use in one or more assay formats. In selected embodiments the oligomer participates in the generation of a detectable signal upon association with or dissociation from its target. The oligomeric probes of the invention are not limited in use to any particular assay format. Accordingly, the following description is intended to illustrate exemplary assays formats in which the oligomers of the invention find use, and is not intended to be limiting of the assay formats in which the oligomers are of use.

Assays

The following discussion is generally relevant to the assays described herein. This discussion is intended to illustrate the invention by reference to certain preferred embodiments and should not be interpreted as limiting the scope of probes and assay types in which the compounds of the invention find use. Other assay formats utilizing the compounds of the invention will be apparent to those of skill in the art.

In general, to determine the concentration of a target molecule, such as, for example, a nucleic acid, it is preferable to first obtain reference data in which constant amounts of probe and nucleic acid ligand are contacted with varying amounts of target. The fluorescence emission of each of the reference mixtures is used to derive a graph or table in which target concentration is compared to fluorescence emission. For example, a probe that: a) hybridizes to a target-free nucleic acid ligand; and b) has a stem-loop architecture with the 5' and 3' termini being the sites of fluorescent group and BHQ labeling, can be used to obtain such reference data. Such a probe gives a characteristic emission profile in which the fluorescence emission decreases as the target concentration increases in the presence of a constant amount of probe and nucleic acid ligand. Then, a test mixture with an unknown amount of target is contacted with the same amount of first nucleic acid ligand and second probe, and the fluorescence emission is determined. The value of the fluorescence emission is then compared with the reference data to obtain the concentration of the target in the test mixture.

Multiplex Analyses

In another embodiment, the solid supports and oligomers of the invention are utilized as a probe or a component of one or more probes used in a multiplex assay for detecting one or more species in a mixture.

Probes based on the solid supports or oligomers of the invention are particularly useful in performing multiplex-type analyses and assays. In a typical multiplex analysis, two or more distinct species (or regions of one or more species) are detected using two or more probes, wherein each of the probes is labeled with a different fluorophore. Preferred species used in multiplex analyses relying on donor-acceptor energy transfer meet at least two criteria: the fluorescent species is bright and spectrally well-resolved; and the energy transfer between the fluorescent species and the quencher is efficient.

The solid supports and oligomers of the invention allow for the design of multiplex assays in which more than one quencher structure is used in the assay. A number of different multiplex assays using the solid supports or oligomers of the invention will be apparent to one of skill in the art. In one exemplary assay, each of the at least two distinct quenchers is used to quench energy derived from one or more identical fluorophore. Alternatively, an assay can be practiced in which each distinct quencher quenches energy derived from a distinct fluorophore to which the quencher is "matched." The fluorophores can be bound to the same molecule as the quencher or to a different molecule. Moreover, similar to the quencher and the fluorophores, the carrier molecules of use in a particular assay system can be the same or different.

In addition to the mixtures described above, the present invention also provides a method for detecting or quantifying a particular molecular species. The method includes: (a) contacting the species with a mixture containing a solid support or oligomer of the invention; and (b) detecting a change in a fluorescent property of one or more component of the resulting mixture, thereby detecting or quantifying the molecular species.

The simultaneous use of two or more probes using donor-acceptor energy transfer is known in the art. For example, multiplex assays using nucleic acid probes with different sequence specificities have been described. Fluorescent probes have been used to determine whether an individual is homozygous wild-type, homozygous mutant or heterozygous for a particular mutation. For example, using one quenched-fluorescein molecular beacon that recognizes the wild-type sequence and another rhodamine-quenched molecular beacon that recognizes a mutant allele, it is possible to genotype individuals for the β-chemokine receptor (Kostrikis et al. *Science* 279:1228-1229 (1998)). The presence of only a fluorescein signal indicates that the individual is wild-type, and the presence of rhodamine signal only indicates that the individual is a homozygous mutant. The presence of both rhodamine and fluorescein signal is diagnostic of a heterozygote. Tyagi et al. *Nature Biotechnology* 16: 49-53 (1998)) have described the simultaneous use of four differently labeled molecular beacons for allele discrimination, and Lee et al., *BioTechniques* 27: 342-349 (1999) have described seven color homogenous detection of six PCR products.

The quenchers of the present invention can be used in multiplex assays designed to detect and/or quantify substantially any species, including, for example, whole cells, viruses, proteins (e.g., enzymes, antibodies, receptors), glycoproteins, lipoproteins, subcellular particles, organisms (e.g., *Salmonella*), nucleic acids (e.g., DNA, RNA, and analogues thereof), polysaccharides, lipopolysaccharides, lipids, fatty acids, non-biological polymers and small molecules (e.g., toxins, drugs, pesticides, metabolites, hormones, alkaloids, steroids).

Nucleic Acid Probes

The solid supports and oligomers of the invention are useful nucleic-acid probes and they can be used as components of detection agents in a variety of DNA amplification/quantification strategies including, for example, 5'-nuclease assay, Strand Displacement Amplification (SDA), Nucleic Acid Sequence-Based Amplification (NASBA), Rolling Circle Amplification (RCA), as well as for direct detection of targets in solution phase or solid phase (e.g., array) assays. Furthermore, the solid supports and oligomers can be used in probes of substantially any format, including, for example, format selected from molecular beacons, Scorpion Probes™, Sunrise Probes™, conformationally assisted probes, light up probes, Invader Detection probes, and TaqMan™ probes. See, for example, Cardullo, R., et al., *Proc. Natl. Acad. Sci. USA*, 85:8790-8794 (1988); Dexter, D. L., *J. Chem. Physics*, 21:836-850 (1953); Hochstrasser, R. A., et al., *Biophysical Chemistry*, 45:133-141 (1992); Selvin, P., *Methods in Enzymology*, 246:300-334 (1995); Steinberg, I., *Ann. Rev. Biochem.*, 40:83-114 (1971); Stryer, L., *Ann. Rev. Biochem.*, 47:819-846 (1978); Wang, G., et al., *Tetrahedron Letters*, 31:6493-6496 (1990); Wang, Y., et al., *Anal. Chem.*, 67:1197-1203 (1995); Debouck, C., et al., in supplement to *nature genetics*, 21:48-50 (1999); Rehman, F. N., et al., *Nucleic Acids Research*, 27:649-655 (1999); Cooper, J. P., et al., *Biochemistry*, 29:9261-9268 (1990); Gibson, E. M., et al., *Genome Methods*, 6:995-1001 (1996); Hochstrasser, R. A., et al., *Biophysical Chemistry*, 45:133-141 (1992); Holland, P. M., et al., *Proc Natl. Acad. Sci. USA*, 88:7276-7289 (1991); Lee, L. G., et al., *Nucleic Acids Rsch.*, 21:3761-3766 (1993); Livak, K. J., et al., *PCR Methods and Applications*, Cold Spring Harbor Press (1995); Vamosi, G. et al. *Biophysical Journal*, 71:972-994 (1996); Wittwer, C. T., et al., *Biotechniques*, 22:176-181 (1997); Wittwer, C. T., et al., *Biotechniques*, 22:130-38 (1997); Giesendorf, B. A. J., et al., *Clinical Chemistry*, 44:482-486 (1998); Kostrikis, L. G., et al. *Science*, 279:1228-1229 (1998); Matsuo, T., *Biochemica et Biophlysica Acta*, 1379:178-184 (1998); Piatek, A. S., et al., *Nature Biotechnology*, 16:359-363 (1998); Schofield, P., et al., *Appl. Environ. Microbiology*, 63:1143-1147 (1997); Tyagi S., et al., *Nature Biotechnology*, 16:49-53 (1998); Tyagi, S., et al., *Nature Biotechnology*, 14:303-308 (1996); Nazarenko, I. A., et al., *Nucleic Acids Research*, 25:2516-2521 (1997); Uehara, H., et al., *Biotechniques*, 26:552-558 (1999); D. Whitcombe, et al., *Nature Biotechnology*, 17:804-807 (1999); Lyamichev, V., et al., *Nature Biotechnology*, 17:292 (1999); Daubendiek, et al., *Nature Biotechnology*, 15:273-277 (1997); Lizardi, P. M., et al., *Nature Genetics*, 19:225-232 (1998); Walker, G., et al., *Nucleic Acids Res.*, 20:1691-1696 (1992); Walker, G. T., et al., *Clinical Chemistry*, 42:9-13 (1996); and Compton, J., *Nature*, 350:91-92 (1991).

Thus, the present invention provides a method for detecting a nucleic acid target sequence. The method includes: (a) contacting the target sequence with a detector nucleic acid (e.g., an oligomer of the invention); (b) hybridizing the target binding sequence to the target sequence, thereby altering the conformation of the detector nucleic acid, causing a change in a fluorescence parameter; and (c) detecting the change in the fluorescence parameter, thereby detecting the nucleic acid target sequence.

In the methods described herein, unless otherwise noted, a preferred detector nucleic acid includes a single-stranded target binding sequence. The binding sequence has linked thereto: i) a fluorophore; and ii) a quencher; and iii) a stabilizing moiety. Moreover, prior to its hybridization to a complementary sequence, the detector nucleic acid is preferably in a conformation that allows donor-acceptor energy transfer between the fluorophore and the quencher when the fluorophore is excited. Furthermore, in each of the methods described in this section, a change in fluorescence is detected as an indication of the presence of the target sequence. The change in fluorescence is preferably detected in-real time.

Presently preferred nucleic acid probes do not require the nucleic acid to adopt a secondary structure for the probe to function. In this method, and unless otherwise noted, the other methods described in this section, the detector nucleic acid can assume substantially any intramolecularly associated secondary structure, but this structure is preferably a member selected from hairpins, stem-loop structures, pseudoknots, triple helices and conformationally assisted structures. Moreover, the intramolecularly base-paired secondary structure preferably comprises a portion of the target binding sequence.

In another aspect, the invention provides a method for detecting amplification of a target sequence. The method includes the use of an amplification reaction including the following steps: (a) hybridizing the target sequence and a detector nucleic acid. The detector nucleic acid includes a single-stranded target binding sequence and an intramolecularly associated secondary structure 5' to the target binding sequence. At least a portion of the detector sequence forms a single stranded tail which is available for hybridization to the target sequence; (b) extending the hybridized detector nucleic acid on the target sequence with a polymerase to produce a detector nucleic acid extension product and separating the detector nucleic acid extension product from the target sequence; (c) hybridizing a primer to the detector nucleic acid extension product and extending the primer with the polymerase, thereby linearizing the intramolecularly associated secondary structure and producing a change in a fluorescence parameter; and (d) detecting the change in the fluorescence parameter, thereby detecting the target sequence.

In yet a further aspect, the invention provides a method of ascertaining whether a first nucleic acid and a second nucleic acid hybridize. In this method, the first nucleic acid is an oligomer (in solution or attached to a solid support) according to the invention. The method includes: (a) contacting the first nucleic acid with the second nucleic acid; (b) detecting an alteration in a fluorescent property of a member selected from the first nucleic acid, the second nucleic acid and a combination thereof, thereby ascertaining whether the hybridization occurs.

In various embodiments, the present invention provides probes and methods of use in detecting polymorphism in nucleic acid target sequences. Polymorphism refers to the occurrence of two or more genetically determined alternative sequences or alleles in a population. A polymorphic marker or site is the locus at which divergence occurs. Preferred markers have at least two alleles, each occurring at frequency of greater than 1%, and more preferably greater than 10% or 20% of a selected population. A polymorphic locus may be as small as one base pair. Polymorphic markers include restriction fragment length polymorphisms, variable number of tandem repeats (VNTR's), hypervariable regions, minisatellites, dinucleotide repeats, trinucleotide repeats, tetranucleotide repeats, simple sequence repeats, and insertion elements such as Alu. The first identified allelic form is arbitrarily designated as the reference form and other allelic forms are designated as alternative or variant alleles. The allelic form occurring most frequently in a selected population is sometimes referred to as the wildtype form. Diploid organisms may be homozygous or heterozygous for allelic forms. A diallelic polymorphism has two forms. A triallelic polymorphism has three forms.

In an exemplary embodiment, a probe of the invention is utilized to detect a single nucleotide polymorphism. A single nucleotide polymorphism occurs at a polymorphic site occupied by a single nucleotide, which is the site of variation between allelic sequences. The site is usually preceded by and followed by highly conserved sequences of the allele (e.g., sequences that vary in less than $1/100$ or $1/1000$ members of the populations). A single nucleotide polymorphism usually arises due to substitution of one nucleotide for another at the polymorphic site. A transition is the replacement of one purine by another purine or one pyrimidine by another pyrimidine. A transversion is the replacement of a purine by a pyrimidine or vice versa. Single nucleotide polymorphisms can also arise from a deletion of a nucleotide or an insertion of a nucleotide relative to a reference allele.

A oligomer of the invention bearing both a quencher and a fluorophore can be used or, alternatively, one or more of the nucleic acids can be singly labeled with a single member of an energy transfer pair (e.g. a quencher or fluorophore). When a nucleic acid singly labeled with a quencher is the probe, the interaction between the first and second nucleic acids can be detected by observing the interaction between the quencher and the nucleic acid or, more preferably, the quenching by the quencher of the fluorescence of a fluorophore attached to the second nucleic acid.

In addition to their general utility in probes designed to investigate nucleic acid amplification, polymorphism and detection and quantification, the present solid supports and oligomers can be used in substantially any nucleic acid probe format now known or later discovered. For example, the solid supports and oligomers of the invention can be incorporated into probe motifs, such as Taqman™ probes (Held et al., *Genome Res.* 6: 986-994 (1996), Holland et al., *Proc. Nat. Acad Sci. USA* 88: 7276-7280 (1991), Lee et al. *Nucleic Acids Res.* 21: 3761-3766 (1993)), molecular beacons (Tyagi et al., *Nature Biotechnology* 14:303-308 (1996), Jayasena et al., U.S. Pat. No. 5,989,823, issued Nov. 23, 1999)) scorpion probes (Whitcomb et al., *Nature Biotechnology* 17: 804-807 (1999)), sunrise probes (Nazarenko et al., *Nucleic Acids Res.* 25: 2516-2521 (1997)), conformationally assisted probes (Cook, R., copending and commonly assigned U.S. patent Application 2007/0059752, filed Jun. 9, 1999), peptide nucleic acid (PNA)-based light up probes (Kubista et al., WO 97/45539, December 1997), double-strand specific DNA dyes (Higuchi et al., *Bio/Technology* 10: 413-417 (1992), Wittwer et al., *BioTechniques* 22: 130-138 (1997)) and the like. These and other probe motifs with which the present quenchers can be used are reviewed in NONISOTOPIC DNA PROBE TECHNIQUES, Academic Press, Inc. 1992.

The oligomers for use in the probes of the invention can be any suitable size, and are preferably in the range of from about 10 to about 100 nucleotides, more preferably from about 10 to about 80 nucleotides and more preferably still, from about 20 to about 40 nucleotides. In the dual labeled (fluorophore-quencher) probes, the donor moiety is preferably separated from the quencher by at least about 6, preferably at least about 8, preferably at least about 10 nucleotides, and more preferably by at least about 15 nucleotides. In various embodiments donor moiety is preferably attached to either the 3'- or 5'-terminal nucleotides of the probe. The quencher moiety is also preferably attached to either the 3'- or 5'-terminal nucleotides of the probe. More preferably, the donor and acceptor moieties are attached to the 3'- and 5'- or 5'- and 3'-terminal nucleotides of the probe, respectively, although internal placement is also useful.

The precise sequence and length of a nucleic acid probe of the invention depends in part on the nature of the target polynucleotide to which it binds. The binding location and length may be varied to achieve appropriate annealing and melting properties for a particular embodiment. Guidance for making such design choices can be found in many art-recognized references.

In some embodiments, the 3'-terminal nucleotide of the nucleic acid probe is blocked or rendered incapable of extension by a nucleic acid polymerase. Such blocking is conveniently carried out by the attachment of a donor or acceptor moiety to the terminal 3'-position of the nucleic acid probe, either directly or by a linker moiety.

The nucleic acid can comprise DNA, RNA or chimeric mixtures or derivatives or modified versions thereof. Both the probe and target nucleic acid can be present as a single strand, duplex, triplex, etc. Moreover, the nucleic acid can be modified at the base moiety, sugar moiety, or phosphate backbone with other groups such as radioactive labels, minor groove binders, intercalating agents, acetylinically unsaturated hydrocarbons, fluoroalkyl groups, donor and/or acceptor moieties and the like.

The oligomers of the invention are useful as primers that are discrete sequences or as primers with a random sequence. Random sequence primers are generally about 6 or 7 nucleomonomers in length. Such primers can be used in various nucleic acid amplification protocols (PCR, ligase chain reaction, etc) or in cloning protocols. The 5-substitutions of the invention generally do not interfere with the capacity of the oligomer to function as a primer. Oligomers of the invention having 2'-modifications at sites other than the 3' terminal residue, other modifications that render the oligomer RNase H incompetent or otherwise nuclease stable can be advantageously used as probes or primers for RNA or DNA sequences in cellular extracts or other solutions that contain nucleases. Thus, the oligomers can be used in protocols for amplifying nucleic acid in a sample by mixing the oligomer with a sample containing target nucleic acid, followed by hybridization of the oligomer with the target nucleic acid and amplifying the target nucleic acid by PCR, LCR or other suitable methods.

The oligomers derivatized with chelating agents such as EDTA, DTPA or analogs of 1,2-diaminocyclohexane acetic acid can be utilized in various in vitro diagnostic assays as described (U.S. Pat. Nos. 4,772,548, 4,707,440 and 4,707,352). Alternatively, oligomers of the invention can be derivatized with crosslinker agents such as 5-(3-iodoacetamidoprop-1-yl)-2'-deoxyuridine or 5-(3-(4-bromobutyramido) prop-1-yl)-2'-deoxyuridine and used in various assay methods or kits as described (International Publication No. WO 90/14353).

In addition to the foregoing uses, the ability of the oligomers to inhibit gene expression can be verified in in vitro systems by measuring the levels of expression in subject cells or in recombinant systems, by any suitable method (Graessmann, M., et al., *Nucleic Acids Res.* (1991) 19:53-59).

Conditions that favor hybridization between oligomer of the present invention and target nucleic acid molecules can be determined empirically by those skilled in the art, and can include optimal incubation temperatures, salt concentrations, length and base compositions of oligonucleotide analogue probes, and concentrations of oligomer and nucleic acid molecules of the sample. Preferably, hybridization is performed in the presence of at least one millimolar magnesium and at a pH that is above 6.0. In some embodiments, it may be necessary or desirable to treat a sample to render nucleic acid molecules in the sample single-stranded prior to hybridization. Examples of such treatments include, but are not limited to, treatment with base (preferably followed by neutralization), incubation at high temperature, or treatment with nucleases.

In addition, because the salt dependence of hybridization to nucleic acids is largely determined by the charge density of the backbone of a hybridizing oligonucleotide analogue, increasing the ratio of pPNA monomers in a HypNA-pPNA oligomer or a SerNA-pPNA oligomer of the present invention can increase the salt dependence of hybridization. This can be used to advantage in the methods of the present invention where it can in some aspects be desirable to be able to increase the stringency of hybridization by changing salt conditions, for example, or release a hybridized nucleic acid by reducing the salt concentration. In yet other aspects of the present invention, it can be desirable to have high-affinity binding of an oligonucleotide analogue of the present invention to a nucleic acid in very low salt. In this case, maintaining a ratio of close to 1:1 of HypNA to pPNA monomers in an oligonucleotide analogue of the present invention is advantageous.

The high degree of specificity of oligomers of the present invention in binding to target nucleic acid molecules allow the practitioner to select hybridization conditions that can favor discrimination between nucleic acid sequences that comprise a stretch of sequence that is completely complementary to at least a portion of one or more oligomer and target nucleic acid molecules that comprise a stretch of sequence that comprises a small number of non-complementary bases within a substantially complementary sequence. For example, hybridization or wash temperatures can be selected that permit stable hybrids between oligomer of the present invention and target nucleic acid molecules that are completely complementary along a stretch of sequence but promote dissociation of hybrids between oligomer of the present invention and target nucleic acid molecules that are not completely complementary, including those that comprise one or two base mismatches along a stretch of complementary sequence. The selection of a temperature for hybridization and washes can be dependent, at least in part, on other conditions, such as the salt concentration, the concentration of oligomer and target nucleic acid molecules, the relative proportions of oligomer to target nucleic acid molecules, the length of the oligomers to be hybridized, the base composition of the oligomer and target nucleic acid molecules, the monomer composition of the oligonucleotide analogue molecules, etc. In addition, when selecting for conditions that favor stable hybrids of completely complementary molecules and disfavor stable hybrids between oligomer and target nucleic acid molecules that are mismatched by one or more bases, additional conditions can be taken into account, and, where desirable, altered, including but not limited to, the length of the oligonucleotide analogue to be hybridized, the length of the stretch of sequence of complementarity between oligomer and target nucleic acid molecules, the number of non-complementary bases within a stretch of sequence of complementarity, the identity of mismatched bases, the identity of bases in the vicinity of the mismatched bases, and the relative position of any mismatched bases along a stretch of complementarity. (See, for example, Examples 20, 27, 28, and 29.) Those skilled in the art of nucleic acid hybridization would be able to determine favorable hybridization and wash conditions in using oligomer of the present invention for hybridization to target nucleic acid molecules, depending on the particular application. "Favorable conditions" can be those favoring stable hybrids between oligomer and target nucleic acid molecules that are, at least in part, substantially complementary, including those that comprise one or more mismatches.

"Favorable conditions" can be those favoring stable hybrids between oligomer and target nucleic acid molecules that are, at least in part, completely complementary and disfavor or destabilized hybrids between molecules that are not completely complementary.

Using methods such as those disclosed herein, the melting temperature of oligomer of the present invention hybridized to target nucleic acid molecules of different sequences can be determined and can be used in determining favorable conditions for a given application. It is also possible to empirically determine favorable hybridization conditions by, for example, hybridizing target nucleic acid molecules to oligomer that are attached to a solid support and detecting hybridized complexes.

Target nucleic acid molecules that are bound to solid supports or oligomeric probes of the present invention can be conveniently and efficiently separated from unbound nucleic acid molecules of the survey population by the direct or indirect attachment of oligomer probes to a solid support. A solid support can be washed at high stringency to remove nucleic acid molecules that are not bound to oligomer probes. However, the attachment of oligomer probes to a solid support is not a requirement of the present invention. For example, in some applications bound and unbound nucleic acid molecules can be separated by centrifugation through a matrix or by phase separation or some by other forms of separation (for example, differential precipitation) that can optionally be aided by chemical groups incorporated into the oligomer probes (see, for example, U.S. Pat. No. 6,060,242 issued May 9, 2000, to Nie et al.).

Nucleic Acid Capture Probes

In one embodiment, an immobilized nucleic acid comprising a quencher and a stabilizing moiety is used as a capture probe. The nucleic acid probe can be attached directly to a solid support, for example by attachment of the 3'- or 5'-terminal nucleotide of the probe to the solid support. More preferably, however, the probe is attached to the solid support by a linker (supra). The linker serves to distance the probe from the solid support. The linker is most preferably from about 5 to about 30 atoms in length, more preferably from about 10 to about 50 atoms in length.

In various embodiments, the solid support is also used as the synthesis support in preparing the oligomer (probe). The length and chemical stability of the linker between the solid support and the first 3'-unit of nucleic acid play an important role in efficient synthesis and hybridization of support bound nucleic acids. The linker arm is preferably sufficiently long so that a high yield (>97%) can be achieved during automated synthesis. The required length of the linker will depend on the particular solid support used. For example, a six atom linker is generally sufficient to achieve a >97% yield during automated synthesis of nucleic acids when high cross-linked polystyrene is used as the solid support. The linker arm is preferably at least 20 atoms long in order to attain a high yield (>97%) during automated synthesis when CPG is used as the solid support.

Hybridization of a probe immobilized on a solid support generally requires that the probe be separated from the solid support by at least 30 atoms, more preferably at least 50 atoms. In order to achieve this separation, the linker generally includes a spacer positioned between the linker and the 3'-terminus. For nucleic acid synthesis, the linker arm is usually attached to the 3'-OH of the 3'-terminus by an ester linkage which can be cleaved with basic reagents to free the nucleic acid from the solid support.

A wide variety of linkers are known in the art, which may be used to attach the nucleic acid probe to the solid support. The linker may be formed of any compound, which does not significantly interfere with the hybridization of the target sequence to the probe attached to the solid support. The linker may be formed of, for example, a homopolymeric nucleic acid, which can be readily added on to the linker by automated synthesis. Alternatively, polymers such as functionalized polyethylene glycol can be used as the linker. Such polymers are presently preferred over homopolymeric nucleic acids because they do not significantly interfere with the hybridization of probe to the target nucleic acid. Polyethylene glycol is particularly preferred because it is commercially available, soluble in both organic and aqueous media, easy to functionalize, and completely stable under nucleic acid synthesis and post-synthesis conditions.

The linkage fragments between the solid support, the linker and the probe are preferably not cleaved during synthesis or removal of base protecting groups under basic conditions at high temperature. These linkages can, however, be selected from groups that are cleavable under a variety of conditions. Examples of presently preferred linkages include carbamate, ester and amide linkages.

Detection of Nucleic Acids in Samples

Solid supports and oligomers of the present invention can be used for detection of nucleic acids. Such detection methods include: providing a sample, contacting at least one oligonucleotide analogue of the present invention with the sample under conditions that allow hybridization of oligomer to nucleic acid molecules, and detecting one or more nucleic acid molecules of the sample that have hybridized to one or more oligomer of the present invention.

A sample can be from any source, and can be a biological sample, such as a sample from an organism or a group of organisms from the same or different species. A biological sample can be a sample of bodily fluid, for example, a blood sample, serum sample, lymph sample, a bone marrow sample, ascites fluid, pleural fluid, pelvic wash fluid, ocular fluid, urine, semen, sputum, or saliva. A biological sample can also be an extract from cutaneous, nasal, throat, or genital swabs, or extracts of fecal material. Biological samples can also be samples of organs or tissues, including tumors. Biological samples can also be samples of cell cultures, including both cell lines and primary cultures of both prokaryotic and eukaryotic cells.

A sample can be from the environment, such as from a body of water or from the soil, or from a food, beverage, or water source, an industrial source, workplace area, public area, or living area. A sample can be an extract, for example a liquid extract of a soil or food sample. A sample can be a solution made from washing or soaking, or suspending a swab from, articles such as tools, articles of clothing, artifacts, or other materials.

A sample can be an unprocessed or a processed sample; processing can involve steps that increase the purity, concentration, or accessibility of components of the sample to facilitate the analysis of the sample. As nonlimiting examples, processing can include steps that reduce the volume of a sample, remove or separate components of a sample, solubilize a sample or one or more sample components, or disrupt, modify, expose, release, or isolate components of a sample. Nonlimiting examples of such procedures are centrifugation, precipitation, filtration, homogenization, cell lysis, binding of antibodies, cell separation, etc. For example, in some preferred embodiments of the present invention, the sample is a blood sample that is at least partially processed, for example, by the removal of red blood cells, by concentration, by selection of one or more cell or virus types (for example, white blood cells or pathogenic cells), or by lysis of cells, etc.

Exemplary samples include a solution of at least partially purified nucleic acid molecules. The nucleic acid molecules can be from a single source or multiple sources, and can comprise DNA, RNA, or both. For example, a solution of nucleic acid molecules can be a sample that was subjected to any of the steps of cell lysis, concentration, extraction, precipitation, nucleic acid selection (such as, for example, polyA RNA selection or selection of DNA sequences comprising Alu elements), or treatment with one or more enzymes. The sample can also be a solution that comprises synthetic nucleic acid molecules.

An oligomer or solid support of the present invention can be any oligomer format disclosed herein, or any oligomer comprising a monomer, dimer or non nucleic acid component (e.g., linker, fluorophore, quencher, stabilizing moiety) disclosed herein. An oligonucleotide analogue used in the methods of the present invention can be of any length and of any base composition, and can comprise one or more nucleic acid moieties, peptides, proteins lipids, carbohydrates, steroids, and other biochemical and chemical moieties. An oligonucleotide analogue of the present invention can be provided in solution or bound to a solid support. In some preferred embodiments of the present invention, the oligomer comprise HypNA and pPNA residues, and can comprise HypNA and pPNA residues in ratios from about 2:1 to about 1:3. More preferably, the oligomer used in the methods of the present invention comprise ratios of HypNA to pPNA residues from about 1:1 to about 1:2.

Detection methods for bound nucleic acids are well known in the art, and can include the use of a detectable label that is attached to or incorporated into nucleic acid molecules of the survey population or that becomes bound to or incorporated into a hybridized target nucleic acid molecule or hybridized target nucleic acid molecule complex. Detectable labels for nucleic acid molecules are well-known in the art, and comprise fluorescent molecules such as fluorophores (including those set forth herein), radioisotopes, mass-altered chemical groups, specific binding members such as biotin that can be detected by signal-generating molecules, and the like. Detectable labels can also be incorporated into or attached to oligomer of the present invention, for example, in cases where sandwich hybridization using a signal oligomer is used for detection, or detection is performed using a specific binding member such as an antibody that recognizes oligomer/target nucleic acid molecule complexes. Solid supports can be scanned, exposed to film, visually inspected, etc. to determine the presence of a detectable label and thereby determine the binding of a target nucleic acid molecule to an oligomer immobilized on a solid support such as those of the invention.

Kits

One aspect of the instant invention is the formulation of kits that facilitate the practice of syntheses using the solid supports of the invention and assays using oligomers of the invention, as described above. The kits of the invention typically comprise a solid support or oligomer of the invention, either present as a chemically reactive species useful for preparing conjugates, or present as a completed oligomer where the oligomer is a specific binding pair member. The kit optionally further comprises one or more buffering agents, typically present as an aqueous solution. The kits of the invention optionally further comprise additional detection reagents, a purification medium for purifying the resulting labeled substance, luminescence standards, enzymes, enzyme inhibitors, organic solvent, or instructions for carrying out an assay of the invention. Other formats for kits will be apparent to those of skill in the art and are within the scope of the present invention.

By way of summary, the in exemplary embodiments, the present invention provides: A compound having a structure according to Formula I:

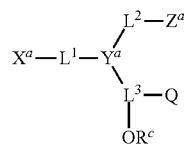
(I)

wherein $X^a$ is a stabilizing moiety which is a member selected from fluoroalkyl, substituted or unsubstituted aryl and substituted or unsubstituted heteroaryl. $L^1$, $L^2$, $L^3$ and $L^4$ are linkers independently selected from substituted or unsubstituted alkyl and substituted or unsubstituted heteroalkyl. $Y^a$ is a member selected from $CR^a$, and N, wherein $R^a$ is a member selected from H, substituted or unsubstituted alkyl and substituted or unsubstituted heteroalkyl. $Z^a$ is a member selected from a solid support, $OR^b$ and $NR^bR^{b'}$, wherein $R^b$ and $R^{b'}$ are independently selected from H, substituted or unsubstituted alkyl and substituted or unsubstituted heteroalkyl. Q is a quencher of fluorescent energy comprising a member selected from:

(a) at least three residues, each independently selected from substituted or unsubstituted aryl, and substituted or unsubstituted heteroaryl wherein a first said residue is covalently linked to a second said residue via a first exocyclic diazo bond and a member selected from said first residue and said second residue is covalently linked to the third residue through a second diazo bond; and (b) at least two residues, each independently selected from substituted or unsubstituted aryl, and substituted or unsubstituted heteroaryl wherein at least two of said residues are covalently linked via an exocyclic diazo bond, with the proviso that at least one said residue is a member selected from substituted or unsubstituted polycyclic aryl and substituted or unsubstituted polycyclic heteroaryl groups;

$R^c$ is a member selected from H, substituted or unsubstituted alkyl, substituted or unsubstituted heteroalkyl, substituted or unsubstituted aryl, substituted or unsubstituted heteroaryl and a phosphorus-containing linker covalently bound to a nucleic acid.

A compound according to the preceding paragraph wherein $R^b$ is fluoroalkyl and $R^c$ is a phosphorus-containing linker covalently bound to a nucleic acid.

A compound according to any preceding paragraph wherein said quencher has a structure according to Formula (II)

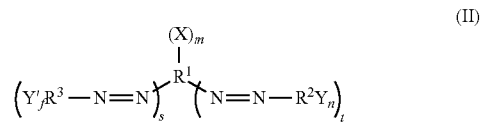
(II)

wherein $R^1$, $R^2$ and $R^3$ are members independently selected from substituted or unsubstituted aryl and substituted or unsubstituted heteroaryl; X, Y and Y' are members independently selected from a reactive functional group and a linkage fragment covalently binding said quencher to $L^3$ is with the proviso that at least one of X, Y and Y' is said linkage fragment; f is an integer from 0 to 4, such that when (f×s) is greater than 1, the Y' groups are the same or different; m is an integer from 0 to 5, such that when m is greater than 1, the X groups are the same or different; n is an integer from 0 to 6, such that when (n×t) is greater than 1, the Y groups are the same or different; s is an integer from 0 to 6, such that when s is greater than 1 the $R^3$ groups are the same or different; and t is an integer from 1 to 6, such that when t is greater than 1 the $R^2$ groups are the same or different, and when t is 1 and s is 0, a member selected from $R^1$, $R^2$ and combinations thereof is a member selected from substituted or unsubstituted polycyclic aryl and substituted or unsubstituted polycyclic heteroaryl groups.

A compound according to any of the preceding paragraphs, wherein said quencher has a structure according to Formula (III):

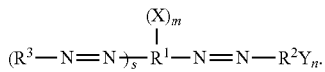

A compound according to any of the preceding paragraphs, wherein a member selected from $R^1$, $R^2$ and $R^3$ includes a structure according to Formula IV:

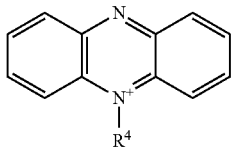

wherein $R^4$ is a member selected from alkyl, substituted alkyl, aryl, substituted aryl, heteroaryl and substituted heteroaryl.

A compound according to any preceding paragraph, wherein said quencher has a structure according to Formula V:

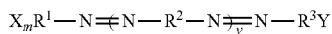

wherein v is an integer from 1 to 10.

A compound according to any preceding paragraph, wherein said quencher has a structure according to Formula VI:

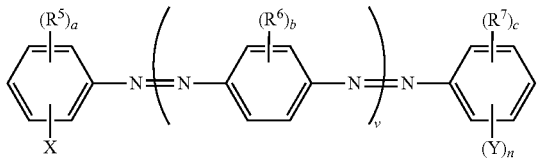

wherein $R^5$, $R^6$ and $R^7$ are members independently selected from —NR'R", substituted or unsubstituted aryl, nitro, substituted or unsubstituted $C_1$-$C_6$ alkyl, and substituted or unsubstituted $C_1$-$C_6$, alkoxy. R' and R" are independently selected from H and substituted or unsubstituted $C_1$-$C_6$ alkyl. The index n is an integer from 0 to 1. The index a is an integer from 0 to 4, such that when a is greater than 1, the $R^5$ groups are the same or different. The index b is an integer from 0 to 4, such that when (v×b) is greater than 1, the $R^6$ groups are the same or different. The index c is an integer from 0 to 5, such that when c is greater than 1, the $R^7$ groups are the same or different; and the index v is an integer from 1 to 10, such that when v is greater than 1, the value of b on each of the b phenyl rings is the same or different.

A compound according to any previous paragraph, wherein said quencher has a structure according to Formula VI:

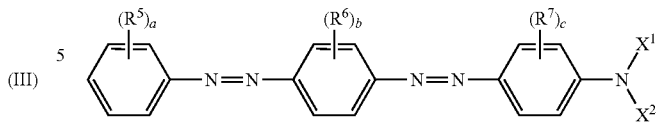

wherein $X^1$ and $X^2$ are members independently selected from $C_1$-$C_6$ alkyl or $C_1$-$C_6$ substituted alkyl, —OH, —COOH, —NR'R", —SH, —OP($OX^3$)($NR^gR^h$) and a linkage fragment covalently binding said quencher to $L^3$, with the proviso that at least one of $R^5$, $R^6$, $X^1$ and $X^2$ comprises said linkage fragment, wherein $R^g$ and $R^h$ are members independently selected from the group consisting of H, and substituted or unsubstituted alkyl and substituted or unsubstituted heteroalkyl.

A compound according to any preceding paragraph, wherein said quencher has a structure which is a member selected from:

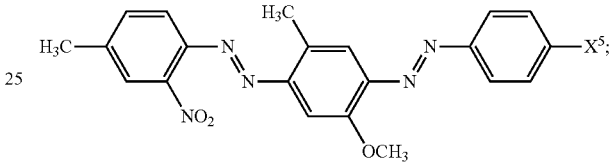

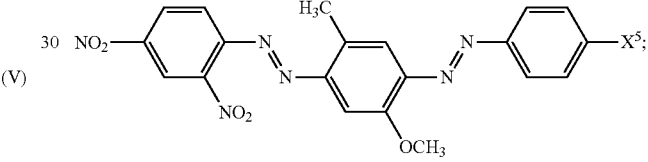

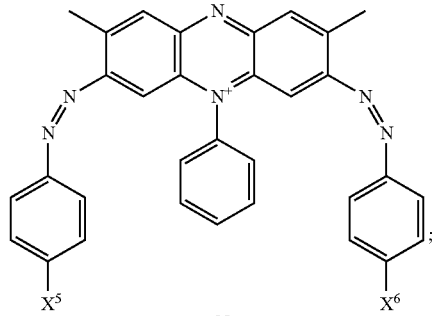

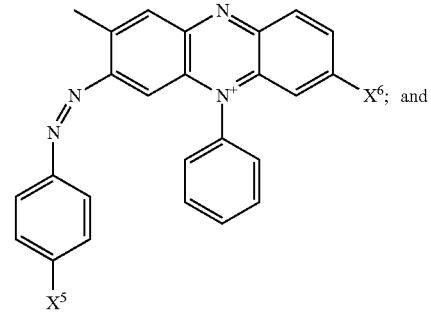

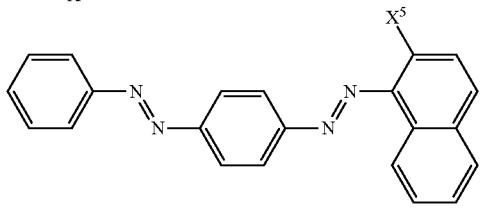

wherein $X^5$ and $X^6$ are members independently selected from H, a reactive functional group and a linkage fragment covalently binding said quencher to $L^3$, with the proviso that at least one of $X^5$ and $X^6$ is said linkage fragment.

A compound according any preceding paragraph, having a structure according to Formula VII:

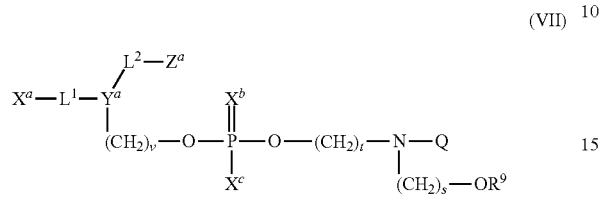

$X^b$ is a member selected from O and S. $X^c$ is a member selected from $OR^8$, $SR^8$ and $NR^8R^{8a}$. $R^8$ and $R^{8a}$ are members independently selected from H, and substituted or unsubstituted alkyl, or $OR^8$ and $SR^8$ are selected from $O^-M^+$ and $S^-M^+$, respectively. M+ is a metal ion. $R^9$ is a member selected from H, substituted or unsubstituted alkyl, substituted or unsubstituted heteroalkyl, substituted or unsubstituted aryl and substituted or unsubstituted heteroaryl and a nucleic acid optionally connected through a phosphorus-containing linker.

A compound according to any preceding paragraph, having a structure according to Formula VIII:

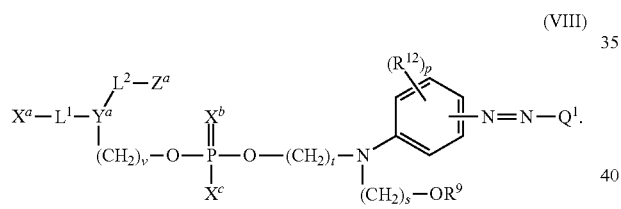

wherein $Q^1$ is a fragment of said quencher, said fragment comprising a member selected from:
(c) two moieties selected from substituted or unsubstituted aryl and substituted or unsubstituted heteroaryl, said two moieties being linked through an exocyclic diazo bond; and
(d) a moiety selected from substituted or unsubstituted polycyclic aryl and substituted or unsubstituted polycyclic heteroaryl groups; and each $R^{12}$ is a member selected from the group of aryl substituents.

A compound according to any preceding paragraph, wherein $Z^a$ is a solid support and $L^2$-$Z^a$ comprises a structure according to Formula IX:

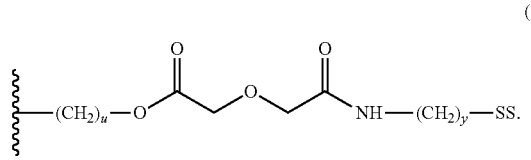

SS is said solid support.

A compound according to any preceding paragraph, wherein $X^a$ is selected from intercalating agents and minor groove binders.

A compound according to any preceding paragraph, wherein said nucleic acid comprises a base having a formula selected from:

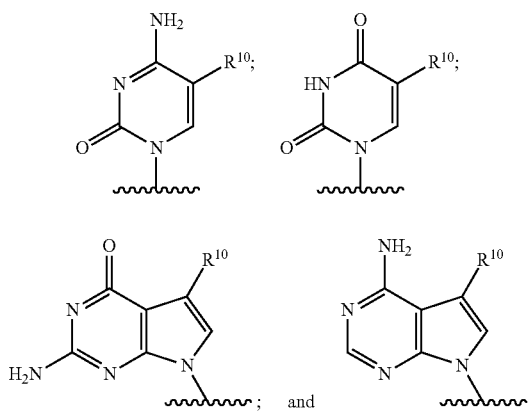

wherein $R^{10}$ is a member selected from an alkynyl and a fluoroalkyl moiety.

A nucleic acid comprising at least one base, having a formula selected from:

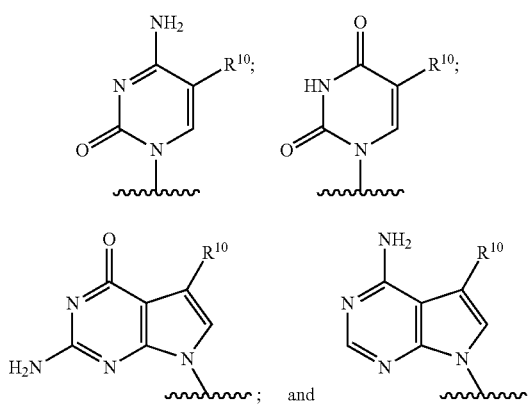

wherein $R^{10}$ is a member selected from an alkynyl and a fluoroalkyl moiety; and a quencher of fluorescence energy comprising at least three residues, each independently selected from substituted or unsubstituted aryl, substituted or unsubstituted heteroaryl and combinations thereof, wherein at least two of said residues are covalently linked via an exocyclic diazo bond.

The materials and methods of the present invention are further illustrated by the examples which follow. These examples are offered to illustrate, but not to limit the claimed invention.

EXAMPLES

Example 1

Synthesis of BHQ1-Plus CPG

1-O-DMT-2-(N-Fmoc-4-aminobutyryl-1,3-propane diol 1 (FIG. 1) was prepared according to Nelson, et al., U.S. Pat. No. 5,942,610 (1999), except that a mixture of THF, water and $Na_2CO_3$ was used (instead of DMF) during the Fmoc addition step leading to 1. After purification by column chromatography, the Fmoc group of 1 was removed with methylamine in ethanol, and after rigorous removal of the methylamine by co-evaporation with pyridine, BOP activated 9-acridinecarboxylic acid was added in DMF. The resulting 1-O-DMT-2-(N-carboxyacridine-4-aminobutyryl)-1,3-propane diol, 2, was isolated by removal of solvents and column chromatography. After further drying by co-evaporation from dry pyridine, diglycolic acid anhydride was added to produce 1-O-DMT-2-(N-carboxyacridine-4-aminobutyryl)-3-O-diglycolate-1,3-propane diol, 3, isolated as its triethylamine salt after column chromatography. 3 was added to aminopropyl CPG, after activation with BOP and NMM, to give DMT acridine CPG 4. Unreacted amine groups on the CPG were capped (acetylated) with a mixture of acetic anhydride and n-methylimidazole in acetonitrile. The DMT loading of CPG 4 was determined to be from 45 to 80 micromoles per gram, found by detritylation (3% DCA/DCM) of a quantity of the dried support and colorometric analysis.

According to FIG. 2, CPG 4 was detritylated (3% DCA/DCM), washed and dried by co-evaporation with pyridine (Scheme 2). BHQ1 DMT amidite (Cook, et al. U.S. Pat. No. 7,109,312 (2006)) was added to the detritylated CPG and activated with 0.5 M ethylthiotetrazole. After 2 minutes, the CPG was washed with MeCN and oxidized with a solution of iodine, pyridine and water in THF. Support 5 was washed, acetylated as above, then well washed and dried. The final DMT loading was 30-50 micromoles/g.

Example 2

Synthesis of 5'-DMTdU-5-Alkynyl(BHQ1)3'-diisopropyl cyanoethyl phosphoramidite

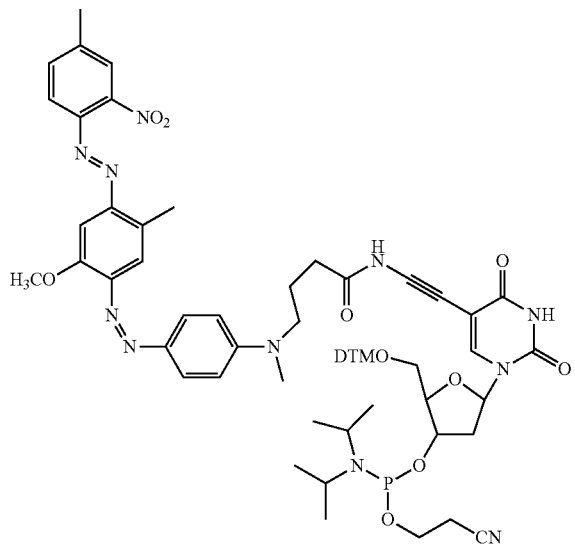

12

Starting with 5-iodouridine 6 the compound 9 was made in a 5 step synthesis. First, Sonogashira coupling (JACS 2005, 127, 15071) with propargylamine trifluoroacetamide, copper iodide and tetrakistriphenylphosphine palladium (0) in DMF with triethylamine gave 5-propargyl(trifluoroacetamide) nucleotide 7 in 37% yield after silica chromatography. The nucleoside was dried well and the 5'DMT group was added by using DMT chloride in dry pyridine to give 8 in 87% yield after chromatography. The TFA amine protecting group was removed with methylamine in ethanol, to give 5-propargylamine nucleoside. Next, BHQ1 C3 carboxylic acid was added to the amine nucleoside with BOP and N-methylmorpholine to produce 5'-DMTdU-5-alkynyl(BHQ1) nucleoside 11.

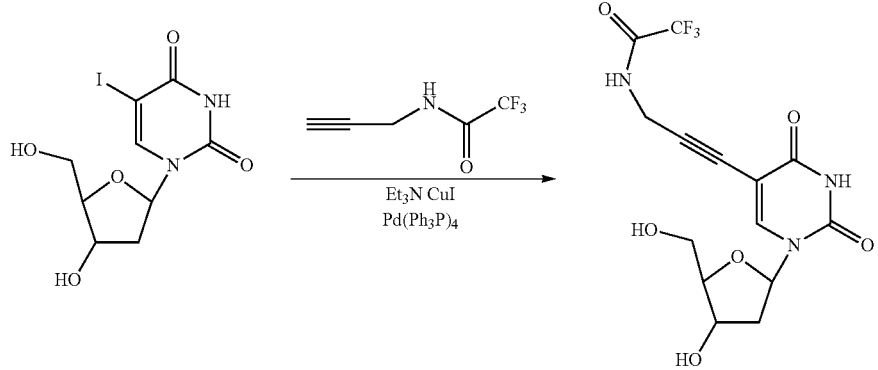

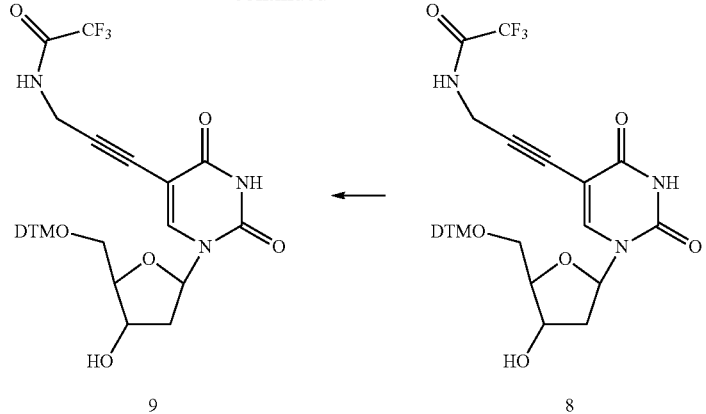

After drying by evaporation from pyridine, the nucleoside 11 was converted into 5'-DMTdU-5-alkynyl(BHQ1)3'-diisopropyl cyanoethyl phosphoramidite 12 with tetraisopropyl cyanoethyl phosphoramidite and tetrazole in a mixture of dry acetonitrile and dichloromethane. After purification on a silica column with a gradient of methanol in dichloromethane with 2% pyridine, 700 mg of 12 were obtained. The phosphoramidite was coupled to 5'-TTTTTTTTTT-3' (SEQ ID NO:1) immobilized on CPG with standard phosphoramidite chemistry. Analysis of the product by ESMS showed a mass of 3809. 5 AMU (Calc'd 3808.5).

It is understood that the examples and embodiments described herein are for illustrative purposes only and that various modification or changes in light thereof will be suggested to persons skilled in the art and are to included within the spirit and purview of this application and are considered within the scope of the appended claims. All publications, patents, and patent applications cited herein are hereby incorporated by reference in their entirety for all purposes.

What is claimed is:

1. A nucleic acid oligomer, wherein said nucleic acid oligomer is prepared by a method comprising:
coupling a monomeric nucleic acid to an acceptor nucleomonomer or an acceptor oligomer,
wherein said monomeric nucleic acid is of the formula:

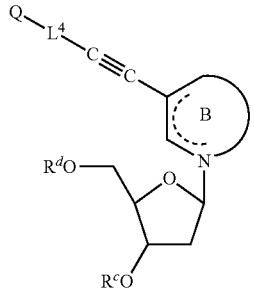

wherein,
Q is a quencher, wherein said quencher is of a structure according to Formula (II)

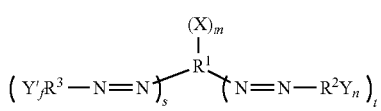

(II)

wherein
$R^1$, $R^2$ and $R^3$ are members independently selected from substituted or unsubstituted aryl, and substituted or unsubstituted heteroaryl;
wherein a member selected from $R^1$, $R^2$ and $R^3$ includes a structure according to Formula IV:

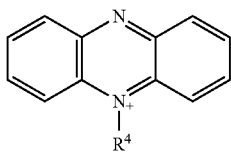

(IV)

wherein $R^4$ is a member selected from alkyl, substituted alkyl, aryl, substituted aryl, heteroaryl and substituted heteroaryl;
X, Y and Y' are members independently selected from a reactive functional group and a linkage fragment covalently binding said quencher to $L^4$, with the proviso that at least one of X, Y and Y' is said linkage fragment;

f is an integer from 0 to 4, such that when (f×s) is greater than 1, the Y' groups are the same or different;

m is an integer from 0 to 5, such that when m is greater than 1, the X groups are the same or different;

n is an integer from 0 to 6, such that when (n×t) is greater than 1, the Y groups are the same or different;

s is an integer from 0 to 6, such that when s is greater than 1 the $R^3$ groups are the same or different; and t is an integer from 1 to 6, such that when t is greater than 1 the $R^2$ groups are the same or different, and when t is 1 and s is 0, a member selected from $R^1$, $R^2$ and combinations thereof is a member selected from substituted or unsubstituted polycyclic aryl and substituted or unsubstituted polycyclic heteroaryl groups;

$L^4$ is a linker;

$R^d$ is a member selected from H, substituted or unsubstituted alkyl, and substituted or unsubstituted heteroalkyl;

$R^c$ is H or a component of a phosphoramidite; and

B is a base.

2. The nucleic acid oligomer according to claim 1, wherein said linker is a member selected from a single covalent bond, substituted or unsubstituted alkyl and substituted or unsubstituted heteroalkyl.

3. The nucleic acid oligomer according to claim 1, wherein $R^d$ is a nucleic acid protecting group.

4. The nucleic acid oligomer according to claim 3, wherein said nucleic acid protecting group is dimethoxytrityl.

5. The nucleic acid oligomer according to claim 1, wherein $R^c$ is

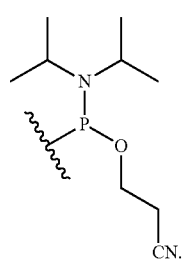 [SMILES: *P(OCCC#N)N(C(C)C)C(C)C]

6. The nucleic acid oligomer according to claim 1, wherein said monomeric nucleic acid is of a formula selected from:

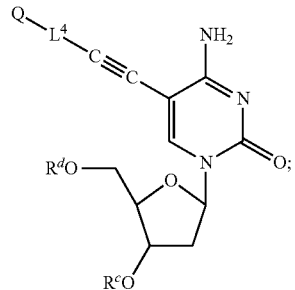

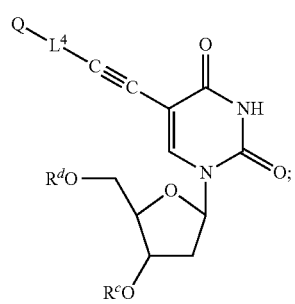

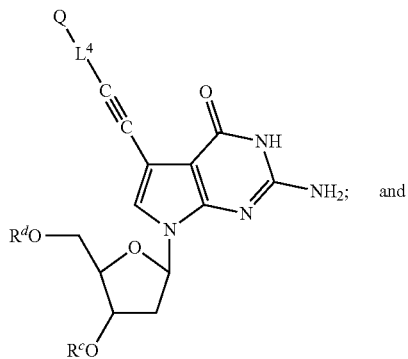

and

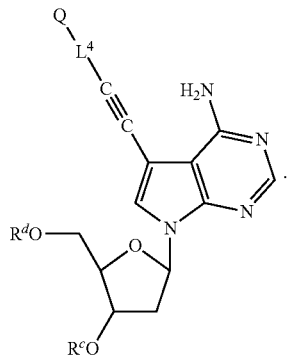

7. The nucleic acid oligomer according to claim 1, wherein

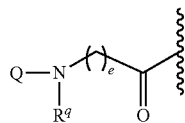

wherein
$R^q$ is a member selected from H, substituted or unsubstituted alkyl and substituted or unsubstituted heteroalkyl; and
e is an integer selected from 1, 2, 3, 4, 5, 6, 7, 8, 9, 10, 11, 12, 13, 14, 15, 16, 17, 18, 19, and 20.

8. The nucleic acid oligomer according to claim 1, wherein said quencher is of a structure according to Formula (III):

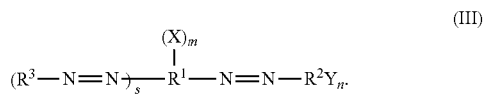

(III)

9. A nucleic acid oligomer, wherein said nucleic acid oligomer is prepared by a method comprising:
coupling a monomeric nucleic acid to an acceptor nucleomonomer or an acceptor oligomer,
wherein said monomeric nucleic acid is of the formula:

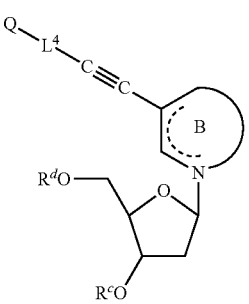

wherein,
Q is a quencher, wherein said quencher is of a structure according to Formula V:

(V)

wherein
$R^1$, $R^2$ and $R^3$ are members independently selected from substituted or unsubstituted aryl, and substituted or unsubstituted heteroaryl;
X and Y are members independently selected from a reactive functional group and a linkage fragment covalently binding said quencher to $L^4$, with the proviso that at least one of X and Y is said linkage fragment;
m is an integer from 0 to 5, such that when m is greater than 1, the X groups are the same or different; and
v is an integer from 1 to 10;
$L^4$ is a linker;
$R^d$ is a member selected from H, substituted or unsubstituted alkyl, and substituted or unsubstituted heteroalkyl;

R$^c$ is H or a component of a phosphoramidite; and
B is a base.

10. A nucleic acid oligomer, wherein said nucleic acid oligomer is prepared by a method comprising:
coupling a monomeric nucleic acid to an acceptor nucleomonomer or an acceptor oligomer,
wherein said monomeric nucleic acid is of the formula:

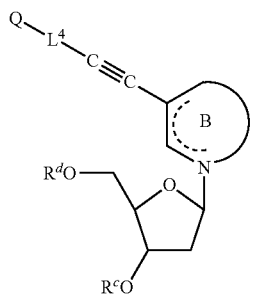

wherein,
Q is a quencher, wherein said quencher is of a structure according to Formula VI:

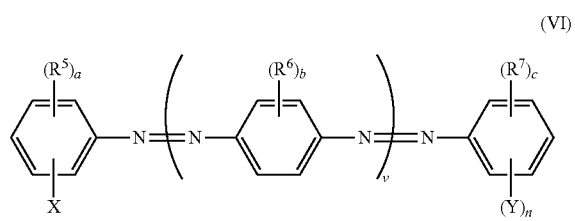

(VI)

wherein
R$^5$, R$^6$ and R$^7$ are members independently selected from —NR'R", substituted or unsubstituted aryl, nitro, substituted or unsubstituted $C_1$-$C_6$ alkyl, and substituted or unsubstituted $C_1$-$C_6$ alkoxy,
wherein R' and R" are independently selected from H and substituted or unsubstituted $C_1$-$C_6$ alkyl;
X and Y are members independently selected from a reactive functional group and a linkage fragment covalently binding said quencher to L$^4$, with the proviso that at least one of X and Y is said linkage fragment;
n is an integer from 0 to 1;
a is an integer from 0 to 4, such that when a is greater than 1, the R$^5$ groups are the same or different;
b is an integer from 0 to 4, such that when (v×b) is greater than 1, the R$^6$ groups are the same or different;
c is an integer from 0 to 5, such that when c is greater than 1, the R$^7$ groups are the same or different; and
v is an integer from 1 to 10, such that when v is greater than 1, the value of b on each of the v phenyl rings is the same or different;
L$^4$ is a linker;
R$^d$ is a member selected from H, substituted or unsubstituted alkyl, and substituted or unsubstituted heteroalkyl;
R$^c$ is H or a component of a phosphoramidite; and
B is a base.

11. A nucleic acid oligomer, wherein said nucleic acid oligomer is prepared by a method comprising:
coupling a monomeric nucleic acid to an acceptor nucleomonomer or an acceptor oligomer,
wherein said monomeric nucleic acid is of the formula:

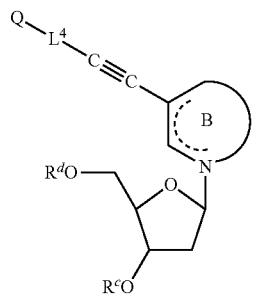

wherein,
Q is a quencher, wherein said quencher is of a structure which is a member selected from:

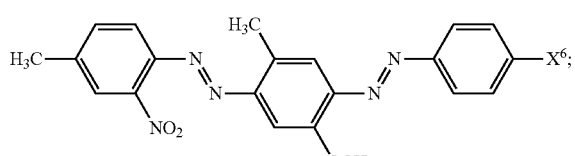

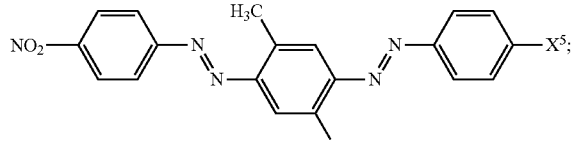

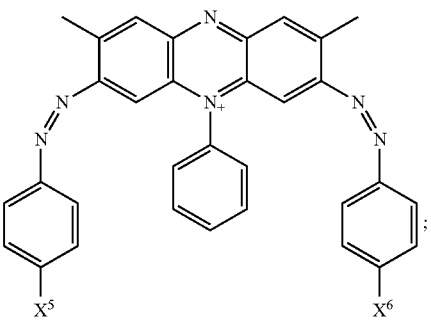

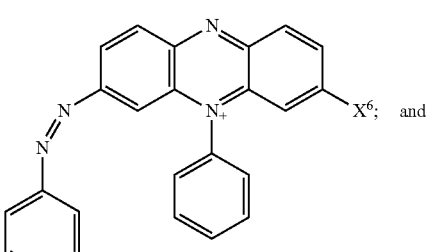

-continued

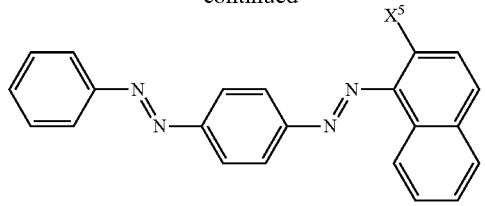

wherein
X⁵ and X⁶ are members independently selected from H, a reactive functional group and a linkage fragment covalently binding said quencher to L⁴, with the proviso that at least one of X⁵ and X⁶ is said linkage fragment;
L⁴ is a linker;
$R^d$ is a member selected from H, substituted or unsubstituted alkyl, and substituted or unsubstituted heteroalkyl;
$R^c$ is H or a component of a phosphoramidite; and
B is a base.

12. The nucleic acid oligomer according to claim 11, wherein said monomeric nucleic acid is of the formula:

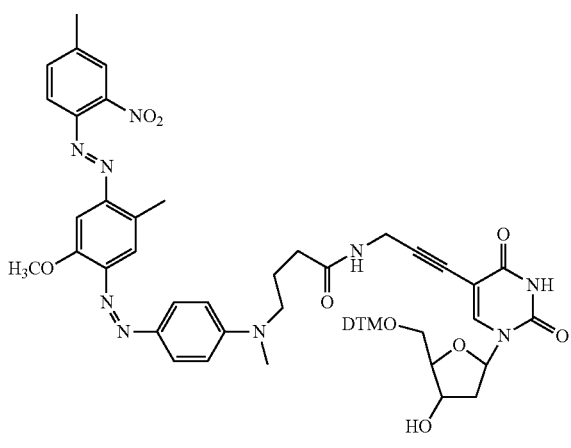

wherein DMT is dimethoxytrityl.

13. The nucleic acid oligomer according to claim 11, wherein said monomeric nucleic acid is of the formula:

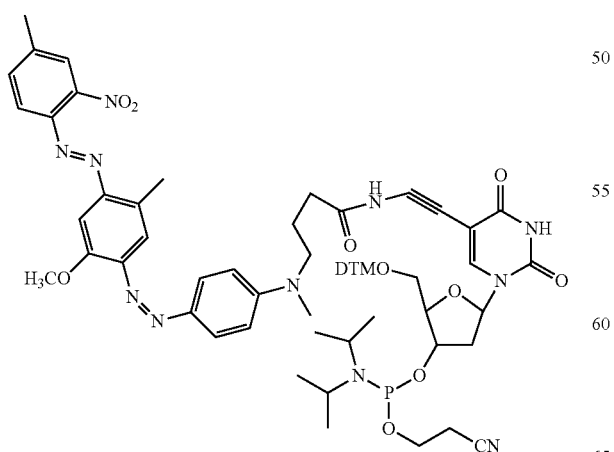

wherein DMT is dimethoxytrityl.

14. The nucleic acid oligomer according to claim 1, wherein said nucleic acid oligomer is a probe.

15. The nucleic acid oligomer according to claim 14, wherein said probe is selected from molecular beacons, scorpion probes, sunrise probes, conformationally assisted probes, light up probes, invader detection probes, and taqman probes.

16. The nucleic acid oligomer according to claim 10, wherein v is 1.

17. The nucleic acid oligomer according to claim 11, wherein said quencher is of the structure:

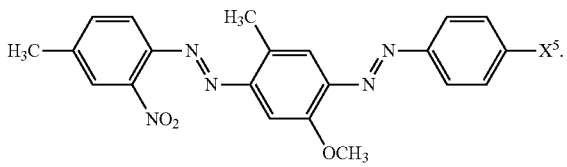

18. The nucleic acid oligomer according to claim 11, wherein said quencher is of the structure:

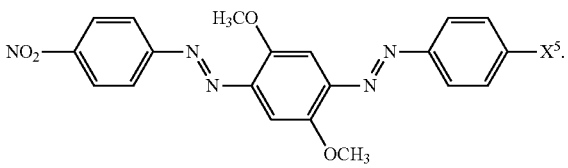

19. The nucleic acid oligomer according to claim 11, wherein said quencher is of the structure:

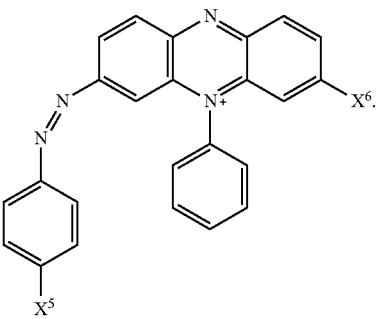

20. A nucleic acid oligomer, wherein said nucleic acid oligomer is prepared by a method comprising:
coupling a monomeric nucleic acid to an acceptor nucleomonomer or an acceptor oligomer,
wherein said monomeric nucleic acid is of the formula:

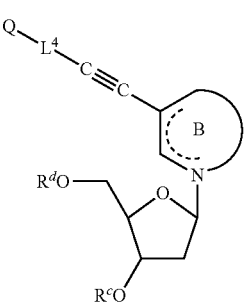

wherein,
Q is a quencher, wherein said quencher is of a structure according to Formula VI:

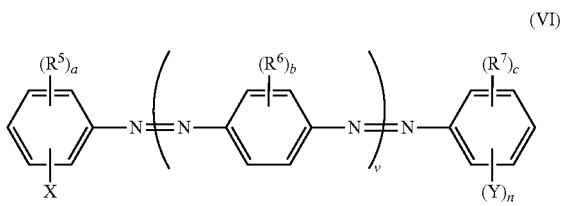

wherein
- R⁵, R⁶ and R⁷ are members independently selected from —NR'R", substituted or unsubstituted aryl, nitro, substituted or unsubstituted $C_1$-$C_6$ alkyl, and substituted or unsubstituted $C_1$-$C_6$ alkoxy, wherein R' and R" are independently selected from H and substituted or unsubstituted $C_1$-$C_6$ alkyl;
- X and Y are members independently selected from a reactive functional group and a linkage fragment covalently binding said quencher to $L^4$, with the proviso that at least one of X and Y is said linkage fragment,
- wherein said linkage fragment is NR', wherein R' is selected from substituted or unsubstituted alkyl and substituted or unsubstituted heteroalkyl;
- n is an integer from 0 to 1;
- a is an integer from 0 to 4, such that when a is greater than 1, the $R^5$ groups are the same or different;
- b is an integer from 0 to 4, such that when (v×b) is greater than 1, the $R^6$ groups are the same or different;
- c is an integer from 0 to 5, such that when c is greater than 1, the $R^7$ groups are the same or different; and
- v is an integer from 1 to 10, such that when v is greater than 1, the value of b on each of the v phenyl rings is the same or different;
- $L^4$ is a linker;
- $R^d$ is a member selected from H, substituted or unsubstituted alkyl, and substituted or unsubstituted heteroalkyl;
- $R^c$ is H or a component of a phosphoramidite; and
- B is a base.

21. The nucleic acid oligomer according to claim 9, wherein said linker is a member selected from a single covalent bond, substituted or unsubstituted alkyl and substituted or unsubstituted heteroalkyl.

22. The nucleic acid oligomer according to claim 9, wherein $R^d$ is a nucleic acid protecting group.

23. The nucleic acid oligomer according to claim 22, wherein said nucleic acid protecting group is dimethoxytrityl.

24. The nucleic acid oligomer according to claim 9, wherein $R^c$ is

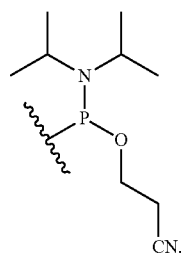 [SMILES: *P(OCCC#N)N(C(C)C)C(C)C]

25. The nucleic acid oligomer according to claim 9, wherein said monomeric nucleic acid is of a formula selected from:

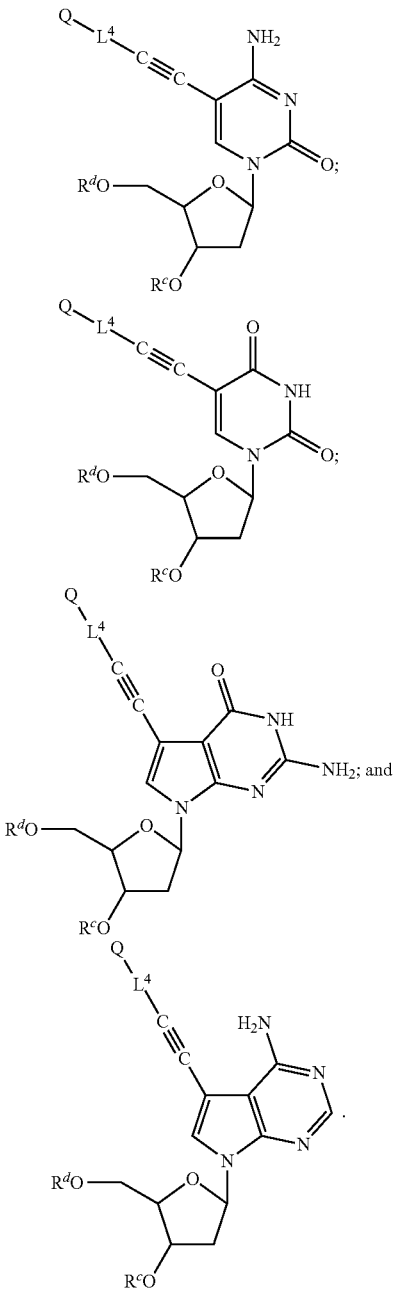

26. The nucleic acid oligomer according to claim 9, wherein Q-$L^4$ is:

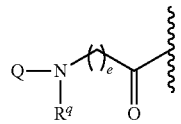

wherein
- $R^q$ is a member selected from H, substituted or unsubstituted alkyl and substituted or unsubstituted heteroalkyl; and
- e is an integer selected from 1, 2, 3, 4, 5, 6, 7, 8, 9, 10, 11, 12, 13, 14, 15, 16, 17, 18, 19, and 20.

27. The nucleic acid oligomer according to claim 9, wherein said nucleic acid oligomer is a probe.

28. The nucleic acid oligomer according to claim 27, wherein said probe is selected from molecular beacons, scorpion probes, sunrise probes, conformationally assisted probes, light up probes, invader detection probes, and taqman probes.

29. The nucleic acid oligomer according to claim 10, wherein said linker is a member selected from a single covalent bond, substituted or unsubstituted alkyl and substituted or unsubstituted heteroalkyl.

30. The nucleic acid oligomer according to claim 10, wherein $R^d$ is a nucleic acid protecting group.

31. The nucleic acid oligomer according to claim 30, wherein said nucleic acid protecting group is dimethoxytrityl.

32. The nucleic acid oligomer according to claim 10, wherein $R^c$ is

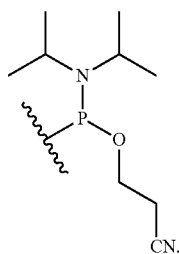 [SMILES: *P(OCCC#N)N(C(C)C)C(C)C]

33. The nucleic acid oligomer according to claim 10, wherein said monomeric nucleic acid is of a formula selected from:

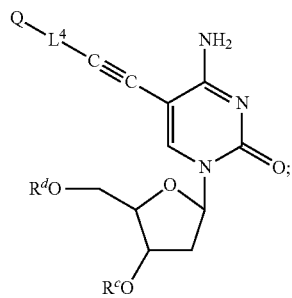

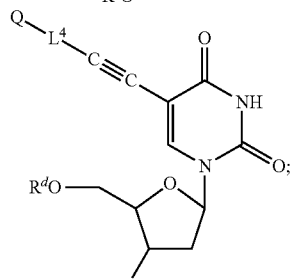

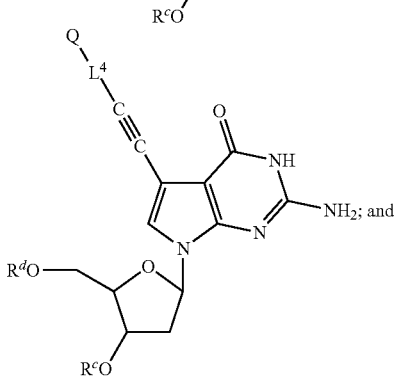

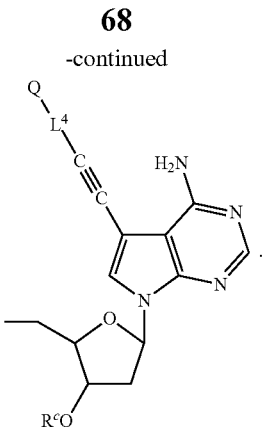

34. The nucleic acid oligomer according to claim 10, wherein Q-$L^4$ is:

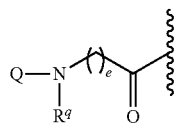

wherein $R^q$ is a member selected from H, substituted or unsubstituted alkyl and substituted or unsubstituted heteroalkyl; and e is an integer selected from 1, 2, 3, 4, 5, 6, 7, 8, 9, 10, 11, 12, 13, 14, 15, 16, 17, 18, 19, and 20.

35. The nucleic acid oligomer according to claim 10, wherein said nucleic acid oligomer is a probe.

36. The nucleic acid oligomer according to claim 35, wherein said probe is selected from molecular beacons, scorpion probes, sunrise probes, conformationally assisted probes, light up probes, invader detection probes, and taqman probes.

37. The nucleic acid oligomer according to claim 11, wherein said linker is a member selected from a single covalent bond, substituted or unsubstituted alkyl and substituted or unsubstituted heteroalkyl.

38. The nucleic acid oligomer according to claim 11, wherein $R^d$ is a nucleic acid protecting group.

39. The nucleic acid oligomer according to claim 38, wherein said nucleic acid protecting group is dimethoxytrityl.

40. The nucleic acid oligomer according to claim 11, wherein $R^c$ is

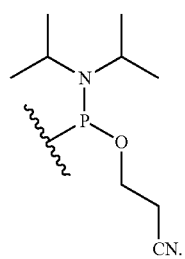 [SMILES: *P(OCCC#N)N(C(C)C)C(C)C]

41. The nucleic acid oligomer according to claim 11, wherein said monomeric nucleic acid is of a formula selected from:

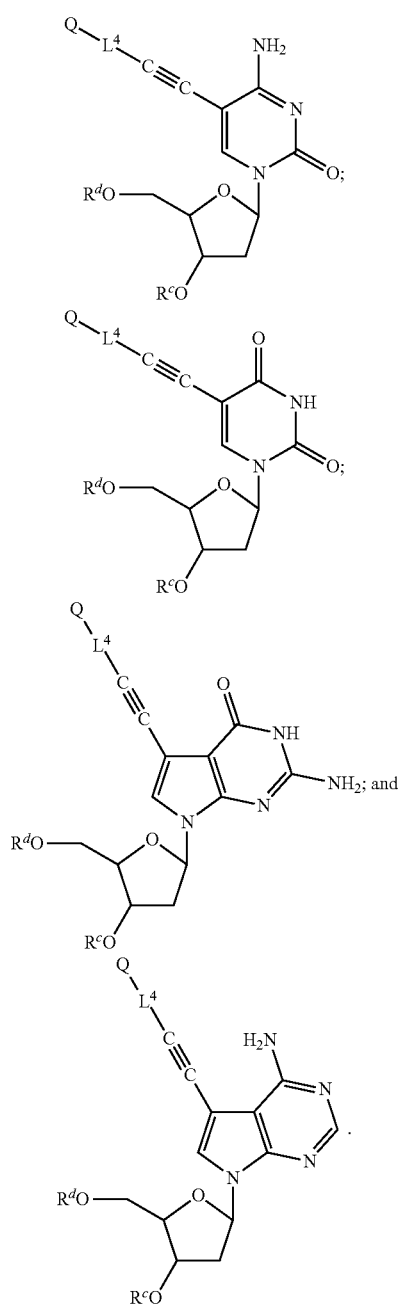

42. The nucleic acid oligomer according to claim 11, wherein Q-L⁴ is:

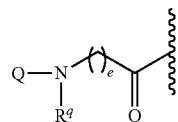

wherein $R^q$ is a member selected from H, substituted or unsubstituted alkyl and substituted or unsubstituted heteroalkyl; and e is an integer selected from 1, 2, 3, 4, 5, 6, 7, 8, 9, 10, 11, 12, 13, 14, 15, 16, 17, 18, 19, and 20.

43. The nucleic acid oligomer according to claim 11, wherein said nucleic acid oligomer is a probe.

44. The nucleic acid oligomer according to claim 43, wherein said probe is selected from molecular beacons, scorpion probes, sunrise probes, conformationally assisted probes, light up probes, invader detection probes, and taqman probes.

45. The nucleic acid oligomer according to claim 20, wherein said linker is a member selected from a single covalent bond, substituted or unsubstituted alkyl and substituted or unsubstituted heteroalkyl.

46. The nucleic acid oligomer according to claim 20, wherein $R^d$ is a nucleic acid protecting group.

47. The nucleic acid oligomer according to claim 46, wherein said nucleic acid protecting group is dimethoxytrityl.

48. The nucleic acid oligomer according to claim 20, wherein $R^c$ is

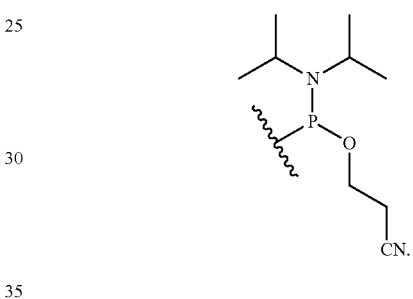

49. The nucleic acid oligomer according to claim 20, wherein said monomeric nucleic acid is of a formula selected from:

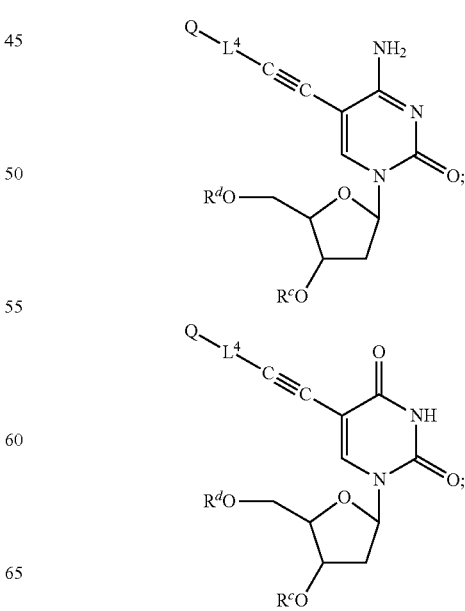

-continued

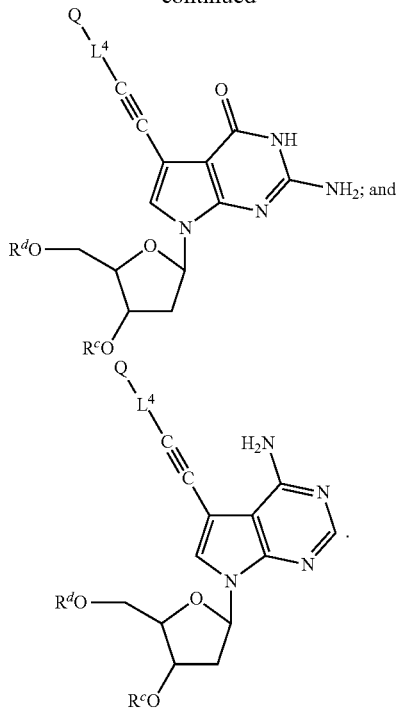

50. The nucleic acid oligomer according to claim 20, wherein Q-L$^4$ is:

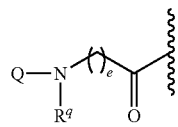

wherein

R$^q$ is a member selected from H, substituted or unsubstituted alkyl and substituted or unsubstituted heteroalkyl; and e is an integer selected from 1, 2, 3, 4, 5, 6, 7, 8, 9, 10, 11, 12, 13, 14, 15, 16, 17, 18, 19, and 20.

51. The nucleic acid oligomer according to claim 20, wherein said nucleic acid oligomer is a probe.

52. The nucleic acid oligomer according to claim 51, wherein said probe is selected from molecular beacons, scorpion probes, sunrise probes, conformationally assisted probes, light up probes, invader detection probes, and taqman probes.

* * * * *